(12) United States Patent
Brennan et al.

(10) Patent No.: US 6,632,641 B1
(45) Date of Patent: *Oct. 14, 2003

(54) METHOD AND APPARATUS FOR PERFORMING LARGE NUMBERS OF REACTIONS USING ARRAY ASSEMBLY WITH RELEASABLE PRIMERS

(75) Inventors: Thomas M. Brennan, San Francisco, CA (US); Francois Chatelain, San Francisco, CA (US); Mark Berninger, North Potomac, MD (US)

(73) Assignee: Metrigen, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/686,597

(22) Filed: Oct. 10, 2000

Related U.S. Application Data

(63) Continuation of application No. 09/684,736, filed on Oct. 6, 2000.
(60) Provisional application No. 60/158,315, filed on Oct. 8, 1999.

(51) Int. Cl.[7] .................... C12Q 1/68; C12P 19/34; C12M 1/34; C07H 21/02; C07H 21/04
(52) U.S. Cl. .................... 435/91.2; 435/6; 435/7.1; 435/91.1; 435/287.2; 530/22.1; 530/23.1; 530/24.3; 530/24.31; 530/24.32; 530/24.33
(58) Field of Search ................. 435/6, 7.1, 91.1, 435/91.2; 536/22.1, 23.1, 24.3–24.33

(56) References Cited

U.S. PATENT DOCUMENTS

| | | | |
|---|---|---|---|
| 4,683,202 A | 7/1987 | Mullis | 435/91 |
| 4,834,946 A | 5/1989 | Levin | 422/101 |
| 5,143,854 A | 9/1992 | Pirrung et al. | 436/518 |
| 5,202,231 A | 4/1993 | Dramanac et al. | 435/6 |
| 5,412,087 A | 5/1995 | McGall et al. | 536/24.3 |
| 5,445,934 A | 8/1995 | Fodor et al. | 435/6 |
| 5,445,943 A | 8/1995 | Hoenes | 435/26 |
| 5,474,796 A | 12/1995 | Brennan | 427/2.13 |
| 5,489,678 A | 2/1996 | Fodor et al. | 536/22.1 |
| 5,492,806 A | 2/1996 | Drmanac et al. | 435/5 |
| 5,525,464 A | 6/1996 | Drmanac | 435/6 |

(List continued on next page.)

FOREIGN PATENT DOCUMENTS

| | | |
|---|---|---|
| EP | 717113 A2 | 6/1996 |
| WO | WO 92/15712 | 9/1992 |

(List continued on next page.)

OTHER PUBLICATIONS

Abramson et al., "Nucleic acid amplification technologies," *Curr. Opin. Biotechnol.* 4:41–47 (1993).

Abravaya et al., "Detection of point mutations with a modified ligase chain reaction", *Nucleic Acids Res.* 23:675–682 (1995).

Adinolfi et al., "Solid Phase Synthesis of Oligosaccharides," *Tetrahedron Lett.* 37(28):5007–5010 (1996).

(List continued on next page.)

*Primary Examiner*—Jeffrey Siew
(74) *Attorney, Agent, or Firm*—Howrey, Simon, Arnold & White, LLP; Albert P. Halluin

(57) ABSTRACT

The present invention relates to a method and apparatus for performing a large number of reactions using array assembly. In particular, the present invention features a method and apparatus for performing a large number of chemical and biological reactions by bringing two arrays into close apposition and allowing reactants on the surfaces of two arrays to come into contact. The present invention is exemplified by performing a large number of polynucleotide amplification reactions using array assembly. In addition, the present invention features a method and apparatus for coupling the amplification of polynucleotides and the detection of sequence variations, expression levels, and functions thereof.

25 Claims, 30 Drawing Sheets

U.S. PATENT DOCUMENTS

| | | | |
|---|---|---|---|
| 5,545,531 A | * 8/1996 | Rava et al. | |
| 5,545,568 A | 8/1996 | Ellman | 436/518 |
| 5,556,749 A | 9/1996 | Mitsuhashi et al. | 435/6 |
| 5,571,639 A | 11/1996 | Hubbell et al. | 430/5 |
| 5,614,608 A | 3/1997 | Krchnak et al. | 530/334 |
| 5,650,277 A | 7/1997 | Navot et al. | 435/6 |
| 5,667,972 A | 9/1997 | Drmanac et al. | 435/6 |
| 5,679,773 A | 10/1997 | Holmes | 530/334 |
| 5,691,141 A | 11/1997 | Köster | 435/6 |
| 5,695,940 A | 12/1997 | Drmanac et al. | 435/6 |
| 5,700,637 A | 12/1997 | Southern | 435/6 |
| 5,700,642 A | 12/1997 | Monforte et al. | 435/6 |
| 5,710,028 A | 1/1998 | Eyal et al. | 435/91.1 |
| 5,739,386 A | 4/1998 | Holmes | 562/437 |
| 5,744,305 A | 4/1998 | Fodor et al. | 435/6 |
| 5,800,992 A | 9/1998 | Fodor et al. | 435/6 |
| 5,830,655 A | 11/1998 | Monforte et al. | 435/6 |
| 5,837,832 A | 11/1998 | Chee et al. | 536/22.1 |
| 5,846,943 A | 12/1998 | Hindsgaul et al. | 514/25 |
| 5,858,653 A | 1/1999 | Duran et al. | 435/6 |
| 5,858,659 A | 1/1999 | Sapolsky et al. | 435/6 |
| 5,871,928 A | 2/1999 | Fodor et al. | 435/6 |
| 5,888,819 A | 3/1999 | Goelet et al. | 435/5 |
| 5,889,165 A | 3/1999 | Fodor et al. | 536/22.1 |
| 5,917,016 A | 6/1999 | Holmes | 530/334 |
| 5,919,626 A | 7/1999 | Shi et al. | 435/6 |
| 5,922,534 A | 7/1999 | Lichtenwalter | 435/6 |
| 5,927,547 A | 7/1999 | Papen et al. | 222/57 |
| 5,929,208 A | 7/1999 | Heller et al. | 530/333 |
| 5,972,619 A | 10/1999 | Drmanac et al. | 435/6 |
| 5,985,551 A | 11/1999 | Brennan | 435/6 |
| 5,985,557 A | 11/1999 | Prudent et al. | 435/6 |
| 5,985,761 A | 11/1999 | Saprks et al. | 438/669 |
| 6,001,567 A | 12/1999 | Brow et al. | 435/6 |
| 6,017,696 A | * 1/2000 | Heller | |
| 6,018,041 A | 1/2000 | Drmanac et al. | 536/24.3 |
| 6,025,136 A | 2/2000 | Drmanac | 435/6 |
| 6,028,189 A | 2/2000 | Blanchard | 536/25.3 |
| 6,030,782 A | 2/2000 | Anderson et al. | 435/6 |
| 6,040,138 A | 3/2000 | Lockhart et al. | 435/6 |
| 6,043,031 A | 3/2000 | Köster et al. | 435/6 |
| 6,054,270 A | 4/2000 | Southern | 435/6 |
| 6,074,823 A | 6/2000 | Köster | 435/6 |
| 6,083,763 A | 7/2000 | Balch | 436/518 |
| 6,090,995 A | 7/2000 | Reich et al. | 623/11 |
| 6,103,479 A | 8/2000 | Taylor | 435/7.2 |
| 6,197,506 B1 | 3/2001 | Fodor et al. | 435/6 |
| 6,210,894 B1 | 4/2001 | Brennan | 435/6 |
| 6,218,118 B1 | * 4/2001 | Sampson et al. | |
| 6,238,869 B1 | * 5/2001 | Kris et al. | 435/6 |
| 6,288,220 B1 | * 9/2001 | Kambara et al. | |
| 6,291,183 B1 | 9/2001 | Pirrung et al. | 435/6 |
| 6,300,066 B1 | * 10/2001 | Gray et al. | |
| 6,300,070 B1 | * 10/2001 | Boles et al. | |
| 6,309,822 B1 | 10/2001 | Fodor et al. | 435/6 |
| 6,309,823 B1 | 10/2001 | Cronin et al. | 435/6 |
| 6,309,831 B1 | 10/2001 | Goldberg et al. | 435/6 |
| 6,310,189 B1 | 10/2001 | Fodor et al. | 435/6 |
| 6,322,968 B1 | * 11/2001 | Head et al. | |

FOREIGN PATENT DOCUMENTS

| | | |
|---|---|---|
| WO | WO 93/09250 | 5/1993 |
| WO | WO 93/17126 | 9/1993 |
| WO | WO 93/17136 | 9/1993 |
| WO | WO 94/11530 | 5/1994 |
| WO | WO 95/11995 | 5/1995 |
| WO | WO 97/28282 | 8/1997 |
| WO | WO 97/35198 | 9/1997 |
| WO | WO 97/43447 | 11/1997 |
| WO | WO 97/45730 | 12/1997 |
| WO | WO 98/09735 | 3/1998 |
| WO | WO 98/21221 | 5/1998 |
| WO | WO 98/22487 | 5/1998 |
| WO | WO 98/28438 | 7/1998 |
| WO | WO 98/30883 | 7/1998 |
| WO | WO 98/33586 | 8/1998 |
| WO | WO 98/38490 | 9/1998 |
| WO | WO 98/38846 | 9/1998 |
| WO | WO 98/41531 | 9/1998 |
| WO | WO 98/46247 | 10/1998 |
| WO | WO 98 47003 | 10/1998 |
| WO | WO 98/50403 | 11/1998 |
| WO | WO 98/54362 | 12/1998 |
| WO | WO 98/56954 | 12/1998 |
| WO | WO 99/05308 | 2/1999 |
| WO | WO 99/06593 | 2/1999 |
| WO | WO 99/06834 | 2/1999 |
| WO | WO 99/07888 | 2/1999 |
| WO | WO 99/09073 | 2/1999 |
| WO | WO 99/14228 | 3/1999 |
| WO | WO 99/21957 | 5/1999 |
| WO | WO 99/27137 | 6/1999 |
| WO | WO 99/37812 | 7/1999 |
| WO | WO 99/39004 | 8/1999 |
| WO | WO 99/47701 | 9/1999 |
| WO | WO 99/54509 | 10/1999 |
| WO | WO 99/58708 | 11/1999 |
| WO | WO 00/03246 | 1/2000 |
| WO | WO 00/17624 | 3/2000 |
| WO | WO 00/17643 | 3/2000 |
| WO | WO 00/50872 | 8/2000 |

OTHER PUBLICATIONS

Albericio et al., "Convergent Solid–Phase Peptide Synthesis," *Methods Enzymol.* 289:313–316 (1997).

Andres, et al., "Transition–metal–mediated reactions in combinatorial synthesis," *Curr. Opin. Chem. Biol.* 2:353–362 (1998).

Atherton et al., *Solid Phase Peptide Synthesis: A practical approach*, IRL press, London (1989).

Ausubel, et al., *Current Protocols in Molecular Biology*, vol. *1–2*, John Wiley & Sons (*1989*).

Beier et al., "Versatile Derivatisation of solid support media for covalent bonding on DNA–microchips," *Nucleic Acids Res.* 27(9):1970–1977 (1999).

Blanchard, et al., "Synthetic DNA Arrays", *Biosensors and Bioelectronics* 11:687–690 (1996).

Blixt et al., "Solid–Phase Enzymatic Synthesis of a Sialyl Lewis X Tetrasaccharide on a Sepharose Matrix," *J. Org. Chem.* 63:2705–2710 (1998).

Brzoska, et al., "Evidence of a transition temperature for the optimum deposition of grafted monolayer coatings," *Nature* *360*:719–721 (1992).

Buhr, et al. "Oligodeoxynucleotides containing C–7 propyne analogs of 7–deaza–2'–deoxyguanosine and 7–deaza–2'–deoxyadenosine," *Nucleic Acids Res.* 24(15):2974–2980 (1996).

Bulyk et al. "Quantifying DNA–protein interations by double–stranded DNA arrays," *Nature Biotechnology,* *17*:573–577 (1999).

Burg et al., "Real–Time Fluorescense Detection of RNA Amplified by Qβ Replicase," *Anal. Biochem.* 230:263–272 (1995).

Cantor and Schimmel, "Part 1: The conformation of Biological macromolecules," Biophycical Chemistry, San Francisco, W.H. Freeman (1980).

Cantor and Smith, *Genomics: the science and technology behind the human genome project*, John Wiley & Sons (1999).
Case–Green, et al. "Analyzing genetic information with DNA arrays," *Cur. Opin. In Chem. Biol.* 2:404–410 (1998).
Czarnik, et al., "Guest Editorial," *Accounts Chem. Rev.* 29:112–170 (1996).
Danishefsky et al., "A Strategy for the Solid–Phase Synthesis of Oligosaccharides," *Science* 260:1307–1309 (1993).
DeRisi, et al., "Exploring the Metabolic and Genetic Control of Gene Expression on A Genomic Scale," *Science* 278:680–686 (1997).
de Wildt, et al., "Antibody arrays for high–throughtput screening of antibody–antigen interactions," *Nature Biotechnol.* 18:989 (2000).
Drmanac et al., "Sequencing of Megabase Plus DNA by Hybridization: Theory of the Method," *Genomics* 4:114–28 (1989).
Drmanac et al., "Accurate sequencing by hybridization for DNA diagnostics and individual genomics," *Nature Biotechnology* 16:54–58 (1998).
Duggan, et al., "Expression profiling using cDNA microarrays," *Nature Genetics Supplement* 21:10–14 (1999).
Eckert et al., "DNA Polymerase Fidelity and the Polymerase Chain Reaction," *PCR Methods and Applications* 1:17 (1991).
Edman, et al., "Electric field directed nucleic acid hybridization on microchips," *Nucleic Acids Research,* 25(24):4907–4914 (1997).
Eisenberg, et al., "Protein function in the post–genomic era," *Nature* 405:823–826 (2000).
Fodor, et al. "Light–Directed, Spatially Addressable Parallel Chemical Synthesis," *Science* 251:767–773 (1991).
Fruchtel, "Organic Chemistry and Solid Supports," *Angew. Chem. Int. Ed. Engl.* 35:17–42 (1996).
Gelfand, et al., "ASDB: database of alternatively spliced genes," *Nucleic Acids Res.* 27(1):301–302 (1999).
Gerhold, et al., "DNA chips: promising toys have become powerful tools," TIBS, 24:168–173 (1999).
Gibson, et al. "A Novel Method for Real Time Quantitative RT–PCR," *Genome Res.* 6:995–1001 (1996).
Giesen, et al., "A formula for thermal stability ($T_m$) prediction of PNA/DNA duplexes," *Nucleic Acids Research* 26(21):5004–5006 (1998).
Good, et al., "Antisense inhibition of gene expression in bacteria by PNA targeted to mRNA," *Nature Biotechnology* 16:355–358 (1998).
Gordon et al. (eds.) Combinatorial Chemistry and Molecular Diversity in Drug Discovery, John Wiley & Son, New York (1997).
Gordon et al., "Applications of Combinatorial Technologies to Drug Discovery. 2. Combinatorial Organic Synthesis, Library Screening Strategies, and Future Directions," *J. Med. Chem.* 37:1385–1401 (1994).
Grant, et al., "Human acetyltransferase polymorphisms," *Mut. Res.* 376:61–70 (1997).
Greenberg et al., "Cleavage of Oligonucleotides from Solid–Phase Supports Using o–Nitrobenzyl Photochemistry," *J. of Org. Chem.* 59:746–753 (1994).
Greenberg, "Photochemical Release of Protected Oliucleotides Containing 3'–Glycolate Termini," *Tetrahedron* 51:29–38 (1995).
Greenberg, "Photochemical Cleavage of Oligonucleotides From Solid Phase Supports," *Tetrahedron Lett.* 34:251–254 (1993).
Gururaja et al., "Solid–Phase Synthesis of Human Salivary Mucin–Derived O–linked Glycopeptide," *Lett Pept. Sci.* 3:79–88 (1996).
Guschin, et al., "Manual Manufacturing of Oligonucleotide, DNA, and Protein Microchips," *Anal. Biochem.* 250:203–211 (1997).
Hammer, et al., "Practical Approach to Solid–Phase Synthesis of C–terminal Peptide Amides under Mild Conditions Based on a Photolysable Anchoring Linkage," *J. Peptide Protein Res.* 36:31–45 (1990).
Heckel, et al., "Oligosaccharide Synthesis on Controlled–Pore Glass as Solid Phase Material," *Synlett* 171–173 (1998).
Heid, et al., "Real Time Quantitative PCR," *Genome Res.* 6:986–994 (1996).
Hermkens, et al., "Solid–Phase Organic Reactions: A review of the Recent Literature," *Tetrahedron* 52:4527–4554 (1996).
Higuchi, et al. Simultaneous Amplification and Detection of Specific DNA Sequences, *Bio/Technology* 10:413–417 (1992).
Higuchi, et al., "Kinetic PCR Analysis: Real–time Monitoring of DNA Amplification Reaction," *Bio/Technology* 11:1026–1030 (1993).
Holmes et al., "Reagents for Combinatorial Organic Synthesis: Development of a New o–Nitrobenzyl Photoabile Linker for Solid Phase Synthesis," *J. of Org. Chem.* 60:2318–2319 (1995).
Holmes, et al., "Model Studies for New o–Nitrobenzyl Photolabile Linkers: Substituent Effects on the Rates of Photochemical Cleavage," *J. of Org. Chem.* 62:2370–2380 (1997).
Hughes, et al., "Functional Discovery via a Compendium of Expression Profiles," *Cell* 102:109–126 (2000).
Hyndman, et al., "Software to Determine Optimal Oligonucleotide Sequnces Based on Hybridization Simulation Data," *BioTechniques* 20(6):1090–1097 (1996).
Ishiguro, et al. "Homogeneous Quantitative Assay of Hepatitis C Virus RNA by Polymerase Chain Reaction in the Presence of a Fluorescent Intercalater," *Anal Biochem.* 229:207–213 (1995).
Isaksson and Landegren, "Accessing genomic information: alternatives to PCR," *Curr. Opin. Biotechnol.* 10:11–15 (1999).
Ito et al., "Solid–phase oligosaccharide synthesis and related technologies," *Curr. Opin. Chem. Biol.* 2:701–708 (1998).
Joos et al., "Covalent Attachment of Hybridizable Oligonucleotides to Glass Supports," *Anal. Chem.* 247:96–101 (1997).
Kahl, et al., "High–Yielding method for On–Column Derivatization of Protected Oligodeoxy–nucleotides and Its Application to the Convergent Synthesis of 5',3'–Bis–conjugates," *J. of Org. Chem.* 63:4870–4871 (1998).
Kahl and Greensberg, "Solution–Phase Bioconjugate Synthesis Using Protected Oligonucleotides Containing 3'–Alky Carboxylic Acids," *J. of Org. Chem.,* 64:507–510 (1999).
Kahn, et al., *Modern Methods in Carbohydrate Synthesis*, Harwood Academic, Amsterdam (1996).
Kierzek, et al., "Association of 2'–5'oligoribonucleotides," *Nucleic Acids Research* 20(7): 1865–1690 (1992).

Kihlberg, et al., "Direct Synthesis of Glycosylated Amino Acids from Carbohydrate Peracetates and Fmoc Amino Acids: Solid–Phase Synthesis of Biomedicinally Interesting Glycopeptides," *Methods Enzymol.* 289:221–245 (1997).

Krokan, et al., "DNA glycosylases in the base excision repair of DNA," *Biochem. J.* 325:1–16 (1997).

Kuppuswami, et al., "Single nucleotide primer extension to detect genetic diseases: Experimental application to hemophilia B (factor IX) and cystic fibrosis genes," *Proc. Natl. Acad. Sci. USA* 88:1143–1147 (1991).

Landegren, "The Challengers to PCR: a proliferation of chain reactions," *Curre. Opin. Biotechnol.* 7:95–97 (1996).

Landegren, et al, "Reading Bits of Genetic Inforation: Methods for Single–Nucleotide Polymorphism Analysis," *Genome Research* 8:769–776 (1998).

Lie, et al., "Advances in quantitative PCR technology 5'nuclease assays," *Curr. Opin. In Biotech.* 9:43–48 (1998).

Lin et al., "Ethnic distribution of slow acetylator mutations in the polymorphic N–acetyltransferase (NAT2) gene," *Pharmacogenetics* 4:124–134 (1994).

Lipshutz, et al., "High density synthetic oligonucleotide arrays," *Nature Genetics Supplement* 21:20–24 (1999).

Livak, et al. "Oligonucleotides with Fluorescent Dyes at Opposite Ends Provide a Quenched Probe System Useful for Detecting PCR Product and Nucleic Acid Hybridization," *PCR Methods and Applications* 4:357–362 (1995).

Lloyd–Williams, et al., "Convergent Solid–phase peptide synthesis," *Tetrahedron* 49:11065–11133 (1993).

Lockhart, et al., "Genomics, gene expression and DNA arrays," *Nature* 405:827–836 (2000).

Malek et al., "Nucleic Acid Sequence–Based Amplication (NASBA)," *Methods Mol. Biol.* 28:253–260 (1994).

Masko, et al., "Oligonucleotide hydridisations on glass supports: a novel linker for oligonucleotide synthesis and hydridisation properties of oligonucleotides synthesised in situ," *Nucleic Acids Research* 20(7):1679–1684 (1992).

Mattila et al., "Fidelity of DNA Synthesis by the *Thermococcus litoralis* DNA polymerase–an extremely heat stable enzyme with proofreading activity," *Nucleic Acids Res.* 19(18):4967–4973 (1991).

Mcdevitt et al. "Glycosamino Acids: New Building Blocks for Cominatorial Synthesis," *J. Am. Chem. Soc.* 118:3818–3828 (1996).

McKenzie, et al., "Parallel molecular genetic analysis," *European Journal of Human Genetics* 6:417–429 (1998).

McMinn et al., "Efficient Solution Phase synthesis of Oligonucleotide Conjugates Using Protected Biopolymers Containing 3'–Terminal Alkyl amines," *J. of Org. Chem.* 62:7074–7075 (1997).

McMinn et al., "Novel Solid Phase Synthesis Supports for the Preparation of Oligonucleotides Containing 3'–Alkyl Amines," *Tetrahedron* 52:3827–3840 (1996).

Meldal et al. "Synthetic methods for glycopeptide assembly, and biological analysis of glycopeptide products," *Curr. Opin. Chem. Biol.* 1:552–563 (1997).

Merrifield, "Solid–Phase Synthesis," *Science* 232:342–347 (1986).

Methods Mol. Biol. "Protocols for Oligonucleotides and Analogs" (ed. Sudhir Agrawal) vol. 20 (1984).

Mitsuhashi, "Technical Report: Part 1. Basic Requirements for Designing Optimal Oligonucleotide Probe Sequences," *J. Clinical Laboratory Analysis* 10:277–284 (1996).

Mrksich, et al., "Controlling cell attachment on contoured surfaces with self–assembeld monlayers of alkanethiolates on gold," *Proc. Natl. Acad. Sci. USA* 93:10775–8 (1996).

Mrksich, et al., "Using Self–Assembled Monolayers to understand the interactions of man–made surfaces with proteins and cells," *Ann. Rev. Biophys. Biomol. Struct.* 25:55–78 (1996).

Muller et al., "Self–sustained sequence replication (3SR): An alternative to PCR," *Histochem. Cell Biol.* 108:431–437 (1997).

Nelson, "Rapid Detection of Genetic Mutations Using the Chemiluminescent Hybridization Protection Assay (HPA): Overview Comparision with Other Methods," *Crit. Rev. Clin. Lab. Sci.* 35:369–414 (1998).

Nicolaou et al., "A General and Highly Efficient Solid Phase Synthesis of Oligosaccharides. Total Synthesis of a Heptasaccharide Phytoalexin Elicitor (HPE)," *J. Am. Chem. Soc.* 119:449–450 (1998).

Nielsen, "Applications of peptide nucleic acids," *Current Opinion in Biotechnology* 10:71–75 (1999).

Nguyen, et al., "Modification of DNA duplexes to smooth their thermal stability independently oft heir base content for DNA sequencing by hybridization," *Nucleic Acids Research* 25(15):3059–3065 (1997).

Nguyen, et al., "The stability of duplexes involving AT and/or $G^{4Et}C$ base pairs is not dependent on their AT/$G^{4Et}C$ ratio content. Implication for DNA sequencing by hybridization," *Nucleic Acids Research* 26(18):4249–4258 (1998).

Pandey, et al., "Proteomics to study genes and genomes," *Nature* 405:837–846 (2000).

Paulsen et al., "New solid–phase oligosaccharide synthesis on glycopeptides bound to a solid phase," *J. Chem. Perkin Trans* 1:281–293 (1997).

*PCR A Practical Approach* (eds. McPherson et al., IRL Press, Oxford, 1991).

*PCR2 A Practical Approach* (eds. McPherson et al., IRL Press, Oxford, 1995).

*PCR Protocols: A Guide to Methods and Applications* (eds. Innis, et al.), Academic Press, San Diego, CA, 1990.

*PCR Technology: Principles and Applifications for DNA Amplication* (ed. H.A. Erlich, Freeman Press, NY, NY, 1992.

Pontius, et al., "Rapid renaturation of complementary DNA strands mediated by cationic detergents: A role for high–probability binding domains in enhancing the dinetics of molecular assembly processes," *Proc. Natl. Acad. Sci. USA* 88:8237–8241 (1991).

Rademann et al., "Repetitive SolidPhase Glycosylation ona an Alkyl Thiol Polymer Leading to Sugar Oligomers Containing 1,2–trans– and 1,2–cis–Glycosidic Linckages," *J. Org. Chem.* 62:3650–3653 (1997).

Rees, et al., "Betaine Can Eliminate the Base Pair Composition Dependence of DNA Melting," *Biochemistry* 3:137–144 (1993).

Rich, et al., "Preparation of a New o–Nitrobenzyl Resin for Solid–Phase Synthesis of tert–Butyloxycarbonyl–Protected Peptide Acids," *J. Am. Chem. Soc.* 97:1575–1579 (1975).

Rich, et al., "Removal of Protected Peptides from an ortho–nitrobenzyl resin by photolysis," *J.C.S. Chem. Comm.* 610–611 (1973).

Roberts, et al., "Signalingand Circuitryof Multiple MAPK Pathways Revealed by a Matrix of Global Gene Expression Profiles," *Science* 287:878–880 (2000).

Rodebaugh et al., "Polymer–Supported Oligosaccharides via n–Pentenyl Glycosides: Methodology for a Carbonhydrate Library," *J. Org. Chem.* 62:5660–5661 (1997).

Rychlik, et al., "A computer program for choosing optimal oligonucleotides for filter hybridization, sequencing and in vitro amplification of DNA," *Nucleic Acids Res.* 17:8543–8551 (1989).

Rychlik, et al., "Optimization of the annealing temperature for DNA amplification in vitro," *Nucleic Acids Res.* 18(21):6409–6412 (1989).

Sambrook et al., *Molecular Cloning: A Laboratory Manual*, 2nd Ed., Cold Spring Harbor Laboratory Press, Cold Spring Harbor, NY, 1989.

Schena et al., "Microarrays: biotechnology's discovery platform for functional geneomics," *TIBTECH* 16:301–306 (1998).

Schullek et al., "A High–density Screening format for Encoded Combinatiorial Libraries: Asssay Miniaturization and its Application to Enzymatic Reactions," *Anal. Biochem.* 246:20–29 (1997).

Shuster et al., "Solid–Phase Chemical–Enzymatic Synthesis of Glycopeptides and Oligosaccharides," *J. Am. Chem. Soc.* 116:1135–1136 (1994).

Silveira and Orgel, "PCR with detachable primers," *Nucleic Acids Research* 23(6):1083–1084.

Singh–Gasson, et al. "Maskless fabrication of light–directed oligonucleotide microarrays using a digital micromirror array," *Nature Biotechnol.* 17:974–978 (1999).

Singhvi, et al., "Engineering Cell Shapte and Function," *Science*, 264:696–698 (1994).

Sokolov, "Primer extension technique for the detection of single nucleotide in genomic DNA," *Nucleic Acids Res.* 18(12):3671 (1990).

Sosnowski et al., "Rapid determination of singel base mismatch mutations in DAN hybrids by direct electric field control," *Proc. Natl. Acad. Sci.* 94:1119–1123 (1997).

Spielberg, et al., "N–Acetyltransferases: Pharmacogenetics and Clinical Consequences of Polymorphic Drug Metabolism," *J. Pharmacokint. Bipharm.* 24(5):509–519 (1996).

Steward, "Cleavage Methods Following Boc–Based Solid–Phase Peptide Synthesis," *Methods in Enzymol.* 289:29–44 (1997).

Syvänen et al., "A Primer–Guilded Nucleotide Incorporation Assay in the Genetyping of Apolipoprotein E," *Genomics* 8:684–692 (1990).

Syvänen, "From Gels to Chips: 'Minisequencing' Primer Extension for Analysis of Point Mutations and Single Nucleotide Polymorphisms", *Human Mutation* 13:1–10 (1999).

Thompson, et al., "Synthesis and Applications of Small Molecule Libraries," *Chem. Rev.* 96:555–600 (1996).

Toshima et al., "Recent Progess in O–glycosylation Methods and Its application to Natural Products Synthesis," *Chem. Rev.* 93:1503–1531 (1993).

Tyagi, et al., "Multicolor Molecular Beacons for allele discrimination," *Nature Biotechnol.* 16:49–53 (1998).

Uetz, et al. "A comprehensive analysis of protein–protein interactions in Saccharomyces," Nature 403:623 (2000).

Van Ness, et al., "The use of oligodeoxynucleotide probes in chaotrope–based hybridization solutions," *Nucleic Acids Research* 19(19):5143–5151 (1991).

Venkatesan and Greenberg, "Improved Utility of Photolabile Sold Phase Synthesis Supports for the Synthesis of Oligonucleotides Containing 3'–Hydroxyl Termini," *J. of Org. Chem.*, 61:525–529 (1996).

Verma and Eckstein, "Modified Oligonucleotides: Synthesis and Strategy for Users," *Annu. Rev. Biochem.* 67:99–134 (1998).

Wagner, et al., "Antisense Gene inhibition by oligonucleotides containing C–5 propyne pyrimidines," *Science* 260:1510–1513 (1993).

Walker, "Empirical Aspects of Strand Displacement Amplication," *PCR Methods Appl.* 3:1–6 (1993).

Wang, "Solid Phase Synthesis of Protected Peptide via Photolytic Clevage of the α–methylphenacyl Ester Anchoring Linkage," *J. Org. Chem.* 41:3258 (1976).

Wang et al., "A New Base–Labile Anchoring Group for Polymer–Supported Oligosaccharide Synthesis," *Chem. Lett.* 273–274 (1995).

Wang, D., et al., "Large–Scale Identification Mapping, and Genotyping of Single–Nucleotide Polymorphisms in the Human Genome," *Science* 280:1077–1082 (1998).

Wetmur, "DNA Probes: Applicationis of the Principles of Nucleic Acid Hybridization," *Critical Reviews in Biochemistry and Molecular Biology* 26:227–259 (1991).

Wiedmann, et al., Ligase Chain Reaction (LCR)—Overview and Applications, *PCR Methods Appl.* 3:S51–64 (1994).

White, "High–Throughput Screening in Drug Metabolism and Pharmacokinetic Support of Drug Discovery," *Annu. Rev. Pharmacol. Toxicol.* 40:133–157 (2000).

Wu, et al., "The Ligation Amplification Reaction (LAR)—Amplification of Specific DNA Sequences Using Sequential Rounds of Template–Dependent Ligation," *Genomics* 4:560–569 (1989).

Yamada, et al., An Efficient Synthesis of Sialoglycoconjugtes on a Peptidase–Sensitive Polymer Support, *Tetrahedron Lett.* 36:9493–9496 (1995).

Yan et al., "Glycosylation on the Merrified Resin Using Anomerica Sulfoxides," *J. Am. Chem. Soc.* 116:6953–6954 (1994).

Yoo et al., "Synthesis of Oligonucleotides Containing 3'Alkyl Carboxylic Acids Using Universal, Photolabile Solid Phase Synthesis Supports," *J. of Org. Chem.* 60:3358–3364 (1995).

Young, "Biomedical Discovery with DNA Arrays," *Cell* 102:9–15 (2000).

Zheng et al., "Solid Support Oligosaccharide Synthesis: Construction of β–Linked Oligosaccharides by Coupling by Glycal Derived Thioethyl Glycosyl Donors," *J. Org. Chem.* 63:1126–1130 (1998).

* cited by examiner

A/G pair interrogates (+) strand
T/C pair interrogates (−) strand

| Probe | Description | ID | Name | 3-5 Sequence |
|---|---|---|---|---|
| F | Forward primer | FPC | F191RevCmp | ctcaaccgaatctccgataaaa |
| R | Reverse primer | RPRC | R191RevCmp | cgggtcatgtcttcaactaactg |
| PC1 | Probe coding 1 | A | 191C_A | CTTTGGACCCACCCA |
| PC2 | Probe coding 2 | G | 191C_G | CTTTGGGCCCACC |
| PN1 | Probe non-coding 1 | T | 191NC_T | TGGGTGGGTCCAAAGAA |
| PN2 | Probe non-coding 2 | C | 191NC_C | TGGGTGGGCCCAAAGAA |
| C+ | Positive Control | + | F191Rev | TTTTATCGGAGATTCGGGTTGAG |
| C− | Negative Control | − | F481Rev | GGAGAGAGAGACAGTTCGTCTT |

Fig. 13

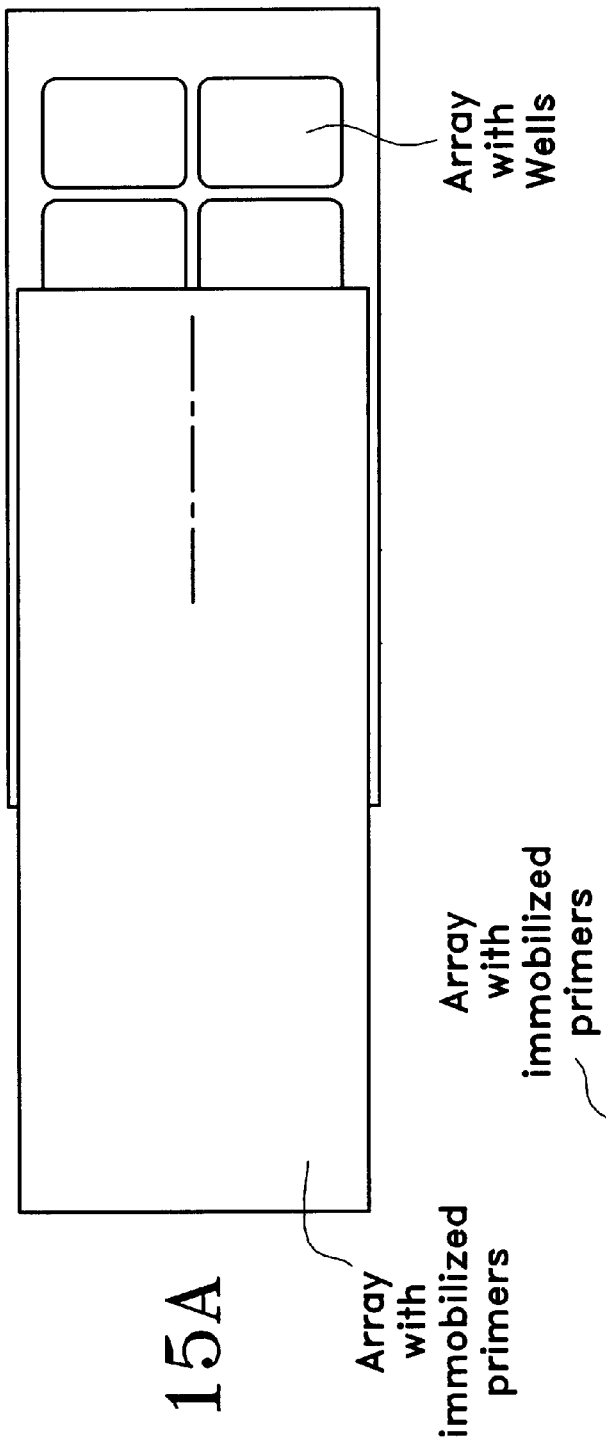
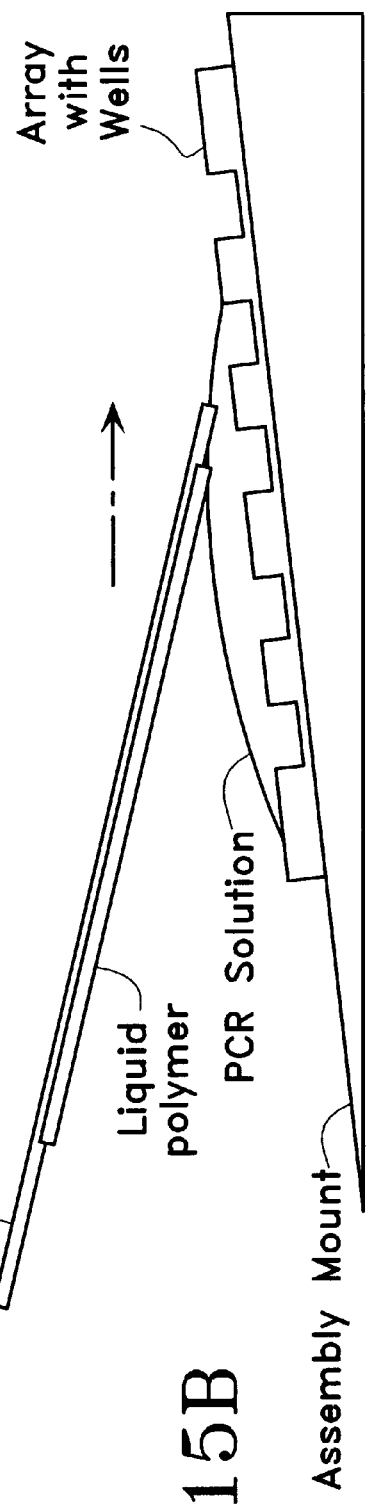
Fig. 15A
Fig. 15B

| Probe | Description | ID | Name | 3-5 Sequence |
|---|---|---|---|---|
| F | Forward primer | + | CompF | AAATAGCCTCTAAGCCCAACTC |
| R | Reverse primer | + | CompR | GTCAATCAACTTCTGTACTGGGC |
| PC(n)A | Probe coding (n) A | A | | TCACATTGTAAGAAGAAACCA |
| PC(n)C | Probe coding (n) C | C | | TCACATTGTAAGAAGAAACCC |
| PC(n)G | Probe coding (n) G | G | | TCACATTGTAAGAAGAAACCG |
| PC(n)T | Probe coding (n) T | T | | TCACATTGTAAGAAGAAACCT |
| PN(n)A | Probe non-coding (n) A | A | | GAGACACCACCCACCCA |
| PN(n)C | Probe non-coding (n) C | C | | GAGACACCACCCACCCC |
| PN(n)G | Probe non-coding (n) G | G | | GAGACACCACCCACCCG |
| PN(n)T | Probe non-coding (n) T | T | | GAGACACCACCCACCCT |
| PC(n-1)A | Probe coding (n-1) A | A | | TGATCACATTGTAAGAAGAAACA |
| PC(n-1)C | Probe coding (n-1) C | C | | TGATCACATTGTAAGAAGAAACC |
| PC(n-1)G | Probe coding (n-1) G | G | | TGATCACATTGTAAGAAGAAACG |
| PC(n-1)T | Probe coding (n-1) T | T | | TGATCACATTGTAAGAAGAAACT |
| PN(n-1)A | Probe non-coding (n-1) A | A | | GGAGACACCACCCACCA |
| PN(n-1)C | Probe non-coding (n-1) C | C | | GGAGACACCACCCACCC |
| PN(n-1)G | Probe non-coding (n-1) G | G | | GGAGACACCACCCACCG |
| PN(n-1)T | Probe non-coding (n-1) T | T | | GGAGACACCACCCACCT |
| C- | negative control | - | (ACTG) | ACTGACTGACTGACTG |

Fig. 18B

METHOD AND APPARATUS FOR PERFORMING LARGE NUMBERS OF REACTIONS USING ARRAY ASSEMBLY WITH RELEASABLE PRIMERS

This application claims priority to U.S. Provisional Application Ser. No. 60/158,315, filed Oct. 8, 1999 (Attorney Docket No. 05871.0010.00US00) and is a continuation U.S. Non-Provisional Application Ser. No. 09/684,736, filed Oct. 6, 2000 .

FIELD OF THE INVENTION

The present invention relates to a method and apparatus for performing a large number of reactions using array assembly. In particular, the present invention features a method and apparatus for performing a large number of chemical and biological reactions by bringing two arrays into close apposition and allowing reactants on the surfaces of two arrays to come into contact. The present invention is exemplified by performing a large number of polynucleotide amplification reactions using array assembly. In addition, the present invention features a method and apparatus for coupling the amplification of polynucleotides and the detection of sequence variations, expression levels, and functions thereof.

BACKGROUND OF THE INVENTION

Intense efforts are under way to map and sequence the human genome and the genomes of many other species. In June 2000, the Human Genome Project and Celera Genomics announced that a rough draft of the human genome had been completed. This information, however, represents only a reference sequence of the 3-billion-base human genome. The remaining task lies in the determination of sequence variations (e.g., mutations, polymorphisms, haplotypes) and sequence functions, which are important for the study, diagnosis, and treatment of human genetic diseases.

In addition to the human genome, the mouse genome is being sequenced. Genbank provides about 1.2% of the 3-billion-base mouse genome and a rough draft of the mouse genome is expected to be available by 2003 and a finished genome by 2005. The Drosophila Genome Project has also been completed recently. Thus far, genomes of more than 30 organisms have been sequenced.

Traditional nucleic acid sequencing methods include the chemical cleavage method (or the Maxam-Gilbert method) and the chain termination method (or the Sanger method) (Sambrook et al., *Molecular Cloning: A Laboratory Manual*, 2$^{nd}$ Ed., Cold Spring Harbor Laboratory Press, Cold Spring Harbor, N.Y., 1989). The basic strategy for the chemical cleavage method is to specifically cleave the end-labeled DNA at only one type of nucleotide, which produces a set of labeled fragments. These labeled fragments are then separated according to their size by electrophoresis. The DNA sequence can be directly read off an autoradiogram. The chain termination method utilizes a DNA polymerase to make complementary copies of the single-stranded DNA being sequenced in the presence of a suitable primer and four deoxynucleoside triphosphates (dNTPs), of which at least one is labeled. In addition, a small amount of the 2', 3'-dideoxynucleoside triphosphate of one of the bases is added to the sequencing reaction, which generates a series of truncated chains. Each truncated chain is terminated by the dideoxy analog at positions occupied by the corresponding base, because of the absence of a 3'-OH group. Electrophoresis separates these truncated chains according to their sizes, thus indicating the positions at which dideoxy incorporation occurs and in turn the corresponding normal nucleotide. Although the efficiency of the traditional sequencing methods has been improved by automation, the use of gel electrophoresis in both methods presents a limitation on the rate of sequencing.

While the traditional chemical cleavage and chain termination sequencing methods are capable of identifying the sequence of all nucleotides in a target nucleic acid, it is quite sufficient in many cases to know the sequence identity of a single nucleotide (or a few nucleotides) at a predetermined site, i.e., the detection of known sequence variations. During the past decade, the development of array-based hybridization technology has received great attention. This high throughput method, in which hundreds to thousands of polynucleotide probes immobilized on a solid surface are hybridized to target nucleic acids to gain sequence and function information, has brought economical incentives to many applications. See, e.g., McKenzie, S., et al., *European Journal of Human Genetics* 416–429 (1998), Green et al., *Curr. Opin. in Chem. Biol.* 2:404–410 (1998), Gerhold et al., *TIBS,* 24:168–173 (1999), Young, *Cell* 102:9–15 (2000), and U.S. Pat. Nos. 5,700,637, 6,054,270, 5,837,832, 5,744,305, and 5,445,943.

DNA array-based sequencing technology generally falls into two categories. The first category is sequencing by polynucleotide hybridization. Sets of polynucleotide probes, that differ by having A, T, C, or G substituted at or near the central position, are immobilized on a solid support by in situ synthesis or by deposition of pre-synthesized polynucleotide probes. Labeled target nucleic acids containing the sequences of interest will hybridize best to perfectly matched polynucleotide probes, whereas sequence variations will alter the hybridization pattern, thereby allowing the determination of mutations and polymorphic sites (Wang, D., et al., *Science* 280:1077–1082 (1998), Lipshutz, R., et al., *Nature Genetics Supplement* 21:20–24 (1999), and Drmanac et al., *Nature Biotechnology* 16:5–58 (1998)).

Alternatively, the de novo sequencing of target nucleic acids by polynucleotide hybridization may also be accomplished. For example, an array of all possible 8-mer polynucleotide probes may be hybridized with fluorescently labeled target nucleic acids, generating large amounts of overlapping hybridization data. The reassembling of this data by computer algorithm can determine the sequence of target nucleic acids. See, e.g., Drmanac, S. et al., *Nature Biotechnology* 116:54–58 (1998), Drmanac, S. et al. *Genomics* 4:114–28 (1989), and U.S. Pat. Nos. 5,202,231, 5,492,806, 5,525,464, 5,667,972, 5,695,940, 5,972,619, 6,018,041, and 6,025,136.

The second category is sequencing by primer extension reactions (also known as minisequencing). Typically, a DNA polymerase is used specifically to extend an interrogation primer, which anneals to the nucleic acids immediately 3' of the single base substitution of interest, with a single labeled nucleoside triphosphate complementary to the single base substitution (Syvänen, *Human Mutation* 13:1–10 (1999), Syvänen et al., *Genomics* 8:684–692 (1990), Sokolov, *Nucleic Acids Res.* 18:3671 (1990), and Kuppuswami et al., *Proc. Natl. Acad. Sci. USA* 88:1143–1147 (1991)).

While methods of hybridization and primer extension-based nucleic acid sequencing have gained widespread acceptance in commercial areas, there are many limitations to the existing methods. The current methods for determining polynucleotide variations in a target nucleic acid employ discrete amplification steps and sequencing steps (Landegren et al., *Genome Res.* 8:769–776 (1998)). Thus, additional amount of time and labor is required to separate amplification products from the amplification primers and dNTPs before the sequencing reaction. Further, it is estimated that at least about 3,000,000 single nucleotide polymorphisms (SNPs) exist in an individual's genome. As SNPs are dispersed throughout the genome, it is necessary to amplify a large number of discrete regions in the genome so that each SNP can be analyzed. Accordingly, the genetic analysis of a single individual's SNPs can require more than 3,000,000 amplification reactions be carried out and the product of each amplification reaction be analyzed. In addition, genetic analysis of a disease may require extensive genotyping of hundreds of thousands of individuals. Therefore, the number of separate amplification and sequencing reactions can be in the millions. The cost in terms of time, labor, equipment, laboratory space and reagents for carrying out discrete amplification and sequencing reactions on a large-scale is prohibitively high. Finally, the designing, optimizing and manufacturing of probe-immobilized arrays can be costly as well. For example, photolithographic synthesis of an array with N-mer polynucleotides typically requires 4×N different chrome photolithographic masks (i.e., 100 different chrome masks for a 25-mer synthesis) (Singh-Gasson et al., *Nature Biotechnol.* 17:974–978 (1999)). This leads to high cost and long synthesis time. In addition, changing probe length and base composition in photolithographic DNA synthesis means changing masks, which again leads to high redesigning cost and long turnaround time for custom arrays. There is a need in micro array field to develop rapid and inexpensive methods for large-scale sequence variation and function analysis.

The present invention features novel applications of the array technology, in which large numbers of non-unimolecular reactions are initiated and performed by array assembly. This method is capable of generating large amounts of data or products per unit time by carrying out large numbers of reactions in parallel. Furthermore, the present invention is amendable to full automation.

SUMMARY OF THE INVENTION

The present invention relates to a method and apparatus for performing a large number of reactions using array assembly. In particular, the present invention features a method and apparatus for performing a large number of chemical and biological reactions by bringing two arrays into close apposition and allowing reactants on the surfaces of two arrays to come into contact. The present invention is exemplified by performing a large number of polynucleotide amplification reactions using array assembly. In addition, the present invention features a method and apparatus for coupling the amplification of polynucleotides and the detection of sequence variations, expression levels, and functions thereof.

Any suitable solid supports (also known as arrays, chips, etc.) may be used in the present invention. These materials include glass, silicon, quartz, nylon, polystyrene, polyethylene, polypropylene, polytetrafluorethylene, metal, among others. These materials typically have a rigid or semi-rigid surface. In some embodiments, at least one surface of the material is substantially flat. Typically, at least one solid support in the assembly is derivatized to provide covalent or noncovalent attachment to chemical or biological entities. Typically, the density of derivatized sites on an array is between about 10–10,000 per $cm^2$, preferably below about 5,000, 1,000, 400, 200, 100, or 60 per $cm^2$. The area of each site may be about $1\times10^{-3}$ to 5 $mm^2$, preferably less than about 2, 1, 0.5, 0.2, or 0.1 $mm^2$. Typically, the total number of derivatized sites on an array is between about 20–1,000,000, preferably, between about 20–500,000, 20–100,000, 20–50,000, 20–10,000, 20–5,000, 20–1,000, or 20–500. In some embodiments, an array may contain raised or depressed regions, e.g., features such as wells, raised regions, etched trenches, etc. The dimensions of these features are flexible, depending on factors, such as desirable reaction concentration, avoidance of air bubbles upon assembly, mechanical convenience and feasibility, etc. For example, the area of a well on an array is in general larger than one derivatized site on another array. The depth of a well may be less than about 1000 microns, preferably less than about 500, 200 or 100 microns. In preferred embodiments, surface tension arrays may be used. Certain reactants such as biopolymers (polynucleotides, polypeptides, etc.) are synthesized in situ to provide better yield and great flexibility.

The array assembly method provides an environment for simultaneously carrying out between about 10–500,000 reactions, preferably, above about 20, 50, 100, 200, 500, 1,000, 5,000, 10,000, 50,000, or 100,000 reactions. A myriad of chemical and biological reactions may be carried out using the instant method and apparatus. These reactions may involve cells, viruses, nucleic acids, proteins, carbohydrates, lipids, and small molecules, among others. In particular, a large number of polynucleotide amplification reactions or molecular binding reactions may be performed using array assembly. In some embodiments of the instant invention, one or more reactants may be immobilized on an array prior to array assembly. The immobilization may be covalent or non-covalent. For example, one or more reactants may be tethered to an immobilized moiety on the array. In certain embodiments of the instant invention, one or more reactants may be immobilized on an array via a releasable site, for example by tethering to an immobilized molecule with a releasable site. The immobilized reactants may be released from an array upon reacting with cleaving reagents prior to, during or after the array assembly. The release methods may include a variety of enzymatic, or non-enzymatic means, such as chemical, thermal, or photolytic treatment. In certain embodiments, detection of sequence variations or quantitation of polynucleotides may be coupled to the amplification reactions.

In one embodiment, the instant invention provides a system for performing a plurality of reactions comprising: a first solid support having a first reactant of each reaction confined to an area on the surface of said first solid support; and a second solid support having a second reactant of each reaction confined to an area on the surface of said second solid support; wherein said first and second solid supports are assembled to allow said first reactant of each reaction in contact with said second reactant of each reaction, thus providing an environment for performing said plurality of reactions in parallel.

The instant invention also provides a system for performing a plurality of reactions comprising: a first solid support having a reactant of each reaction immobilized on said first solid support; and a second solid support providing a chemical or mechanical separation of said plurality of reactions; wherein said first and second solid supports are assembled to provide an environment for performing said plurality of reactions in parallel.

The instant invention also provides a solid support for performing a plurality of polynucleotide amplification reactions wherein a releasable primer for each amplification reaction is immobilized on an area of the surface of said solid support.

The instant invention also provides a system for amplifying a plurality of target nucleic acids, comprising:
(a) a first solid support wherein
  (1) the surface of said first solid support comprises a plurality of derivatized areas;
  (2) a primer for each target nucleic acid or a sequence complementary to said primer is immobilized on a derivatized area of the first solid support; and
(b) a second solid support wherein said second solid support comprises a plurality of wells and each well corresponds to a primer for each target nucleic acid.

The instant invention also provides a system for amplifying a plurality of target nucleic acids, comprising:
(a) a first solid support wherein
  (1) the surface of said first solid support comprises a plurality of derivatized areas;
  (2) a forward primer for each target nucleic acid or a sequence complementary to said forward primer is immobilized on a derivatized area of the first solid support
  (3) a reverse primer for each region of said target nucleic acid or a sequence complementary to said reverse primer is immobilized on another derivatized area of the first solid support;
(b) a second solid support wherein said second solid support comprises a plurality of wells and each well corresponds to the forward and reverse primers for each target nucleic acid.

The instant invention also provides a system for amplifying a plurality of target nucleic acids and detecting amplified products, comprising:
(a) a first solid support wherein
  (1) the surface of said first solid support comprises a plurality of derivatized areas;
  (2) a primer for each target nucleic acid or a sequence complementary to said primer is immobilized on a derivatized area of the first solid support;
  (4) a probe comprising a subsequence, the same as or complementary to a subsequence of each target nucleic acid, is immobilized on another derivatized area of the first solid support;
(b) a second solid support wherein the surface of said second solid support comprises a plurality of reaction wells and each well corresponds the primer and the probe for each target nucleic acid.

In another embodiment, the instant invention provides a method for performing a plurality of reactions, comprising the steps of:
(a) obtaining a first solid support wherein a first reactant of each reaction is confined to an area on the surface of said first solid support;
(b) obtaining a second solid support wherein a second reactant of each reaction is confined to an area on the surface of said second solid support; and
(c) assembling said first and second solid support, wherein said first reactant on said first solid support is in contact with said second reactant on said second solid support, providing an environment for performing said plurality of reactions in parallel.

The instant invention also provides a method for performing a plurality of polynucleotide amplification reactions, comprising the steps of:
(a) obtaining a first solid support wherein a plurality of immobilized moieties are confined to a plurality of areas on the surface of said first solid support and each said immobilized moiety contains a releasable site and a primer;
(b) obtaining a second solid support wherein the surface of said second solid support contains a plurality of areas and reactants of said polynucleotide amplification reactions are confined on each area of said second solid support;
(c) assembling said first and second solid supports, wherein said reactants of said polynucleotide amplification reactions on said second solid support are in contact with said immobilized moieties on said first solid support; and
(d) releasing said primers.

The instant invention also provides a method for performing a plurality of polynucleotide amplification reactions and capturing amplification products, comprising the steps of:
(a) obtaining a first solid support wherein a plurality of immobilized moieties are confined to a plurality of areas on the surface of said first solid support and each said immobilized moiety contains a releasable site and a primer;
(b) obtaining a second solid support wherein the surface of said second solid support contains a plurality of areas and reactants of said polynucleotide amplification reactions are confined on each area of said second solid support;
(c) assembling said first and second solid supports, wherein said reactants of said polynucleotide aamplification reactions on said second solid support are in contact with said immobilized moieties on said first solid support;
(d) releasing said primers;
(e) generating amplification products of said polynucleotide amplification reactions; and
(f) capturing said amplified products by a plurality of immobilized polynucleotide probes on either said first or second solid support through hybridization.

The instant invention also provides a method for detecting a plurality of polynucleotide sequence variations, comprising the steps of:
(a) obtaining a first solid support wherein a plurality of immobilized moieties are confined to a plurality of areas on the surface of said first solid support and each said immobilized moiety contains a releasable site and a primer;
(b) obtaining a second solid support wherein the surface of said second solid support contains a plurality of areas and reactants of said polynucleotide amplification reactions are confined on each area of said second solid support;
(c) assembling said first and second solid support, wherein said reactants of said polynucleotide amplification reactions on said second solid support are in contact with said immobilized moieties on said first solid support;
(d) releasing said primers;
(e) generating amplification products of said polynucleotide amplification reactions;
(f) capturing said amplified products by a plurality of immobilized polynucleotide probes on either said first or second array through hybridization; and
(g) detecting polynucleotide sequence variations by hybridization complexes in step (f).

The instant invention also provides a method for quantitating polynucleotides in a target nucleic acid, comprising the steps of:

(a) obtaining a first solid support wherein a plurality of immobilized moieties are confined to a plurality of finite areas on the surface of said first solid support and each said immobilized moiety contains a releasable site and a primer;

(b) obtaining a second solid support wherein the surface of said second solid support contains a plurality of areas and reactants of said polynucleotide amplification reactions are confined on each area of said second solid support;

(c) assembling said first and second solid support, wherein said reactants of said polynucleotide amplification reactions on said second solid support are in contact with said immobilized moieties on said first solid support;

(d) releasing said primers;

(e) generating amplification products of said polynucleotide amplification reactions; and (f) quantitating amplified products.

The instant invention also provides a method for detecting polynucleotide sequence variations in a target nucleic acid, comprising the steps of:

(a) obtaining a first solid support wherein a plurality of immobilized moieties are confined to a plurality of areas on the surface of said first solid support and each said immobilized moiety contains a releasable site and a primer;

(b) obtaining a second solid support wherein the surface of said second solid support contains a plurality of areas and reactants of said polynucleotide amplification reactions are confined on each areas of said second solid support;

(c) assembling said first and second solid supports, wherein said reactants of said polynucleotide amplification reactions on said second solid support are in contact with said immobilized moieties on said first solid support;

(d) releasing said primers;

(e) generating amplification products of said polynucleotide amplification reactions; and (f) capturing said amplified products by a plurality of immobilized polynucleotide probes on either first or second array through hybridization; and (g) detecting polynucleotide sequence variations by a polynucleotide modifying enzyme.

The instant invention also provides a method for amplifying a target nucleic acid, capturing the amplified product, and detecting a polynucleotide sequence variation in the amplified product, comprising the steps of:

(a) obtaining a first solid support wherein:
  (1) the surface of said first solid support comprises a first, second, third, and fourth areas;
  (2) a first chemical moiety, comprising a releasable forward primer for said target nucleic acid, is immobilized on said first area;
  (3) a second chemical moiety, comprising a releasable reverse primer for said target nucleic acid, is immobilized on said second area;
  (4) a first polynucleotide probe, comprising a subsequence complementary to one variant of said polynucleotide variation, is immobilized on said third area, said subsequence containing at least one interrogation position complementary to a corresponding nucleotide in said variant; and
  (5) a second polynucleotide probe is immobilized to said fourth area, said second polynucleotide probe differing from said first polynucleotide probe by at least one nucleotide;

(b) obtaining a second solid support wherein the surface of said solid support comprises a reaction well and a mixture of reactants comprising a DNA polymerase, said target nucleic acid, and deoxynucleotides are placed within said reaction well;

(c) assembling said first and second solid support, wherein said mixture of reactants are in contact with said first, second, third, and fourth areas on said first solid support;

(d) releasing said releasable forward and reverse primers;

(e) generating the amplified product for said target nucleic acid;

(f) capturing the amplified product by said first or second polynucleotide probe through hybridization;

(g) disassembling said first and second solid supports;

(h) washing said first solid support;

(i) comparing the relative binding of two probes on said first solid support; and (j) identifying said polynucleotide variation in the amplified product.

The instant invention also provides a method for amplifying a target nucleic acid, capturing the amplified product, and detecting a polynucleotide sequence variation in the amplified product, comprising the steps of:

(a) obtaining a first solid support wherein:
  (1) the surface of said first array comprises a first, second, third, and fourth areas;
  (2) a first chemical moiety, comprising a releasable forward primer specific for said region of said target nucleic acid, is immobilized on said first area;
  (3) a second chemical moiety, comprising a releasable reverse primer specific for said region of said target nucleic acid, is immobilized on said second area;
  (4) a first polynucleotide probe, comprising a subsequence complementary to one variant of said polynucleotide variation, is immobilized on said third area, said subsequence containing at least one interrogation position complementary to a corresponding nucleotide in said variant; and
  (5) a second polynucleotide probe is immobilized to said fourth area, said second probe differing from said first probe by at least one nucleotide;

(b) obtaining a second solid support wherein the surface of said solid support comprises a reaction well and a mixture of reactants comprising a DNA polymerase, said target nucleic acid, and deoxynucleotides are placed within said reaction well;

(c) assembling said first and second solid support, wherein said mixture of reactants are in contact with said first, second, third, and fourth areas on said first solid support;

(d) releasing said releasable forward and reverse primers;

(e) generating the amplified product for said target nucleic acid;

(f) capturing the amplified product by said first or second polynucleotide probes through hybridization;

(g) extending said one or more hybridization complexes in step (f);

(h) disassembling said first and second solid support;

(i) washing said first solid support; and (j) identifying said polynucleotide variation using said one or more extended products in step (g).

BRIEF DESCRIPTION OF THE FIGURES

FIG. 13 illustrates a layout of two unit cells on a derivatized array used for detection by hybridization.

FIG. 15 illustrates an example of array assembly.

DETAILED DESCRIPTION OF THE INVENTION

Before the invention is described in detail, it is to be understood that this invention is not limited to the particular component parts or process steps of the method and apparatus described, as such parts and steps may vary. It is also to be understood that the terminology used herein is for purposes of describing particular embodiments only, and is not intended to be limiting. As used in the specification and the appended claims, the singular forms "a", "an", and "the" include plural references unless the context clearly indicates otherwise.

The present invention relates to a method and apparatus for performing a large number of reactions using array assembly. In particular, the present invention features a method and apparatus for performing a large number of chemical and biological reactions by bringing two arrays into close apposition and allowing reactants on the surfaces of two arrays to come into contact. In addition, selected reactants may be first immobilized on an array and subsequently released before, during or after the assembly with another array.

The present invention is exemplified by performing a large number of polynucleotide amplification reactions using array assembly. In particular, the present invention features a method and apparatus for coupling the amplification of polynucleotides and the detection of sequence variations, expression levels, and functions thereof.

I. Performing Large Numbers of Non-unimolecular Reactions by Array Assembly

Figure 1:
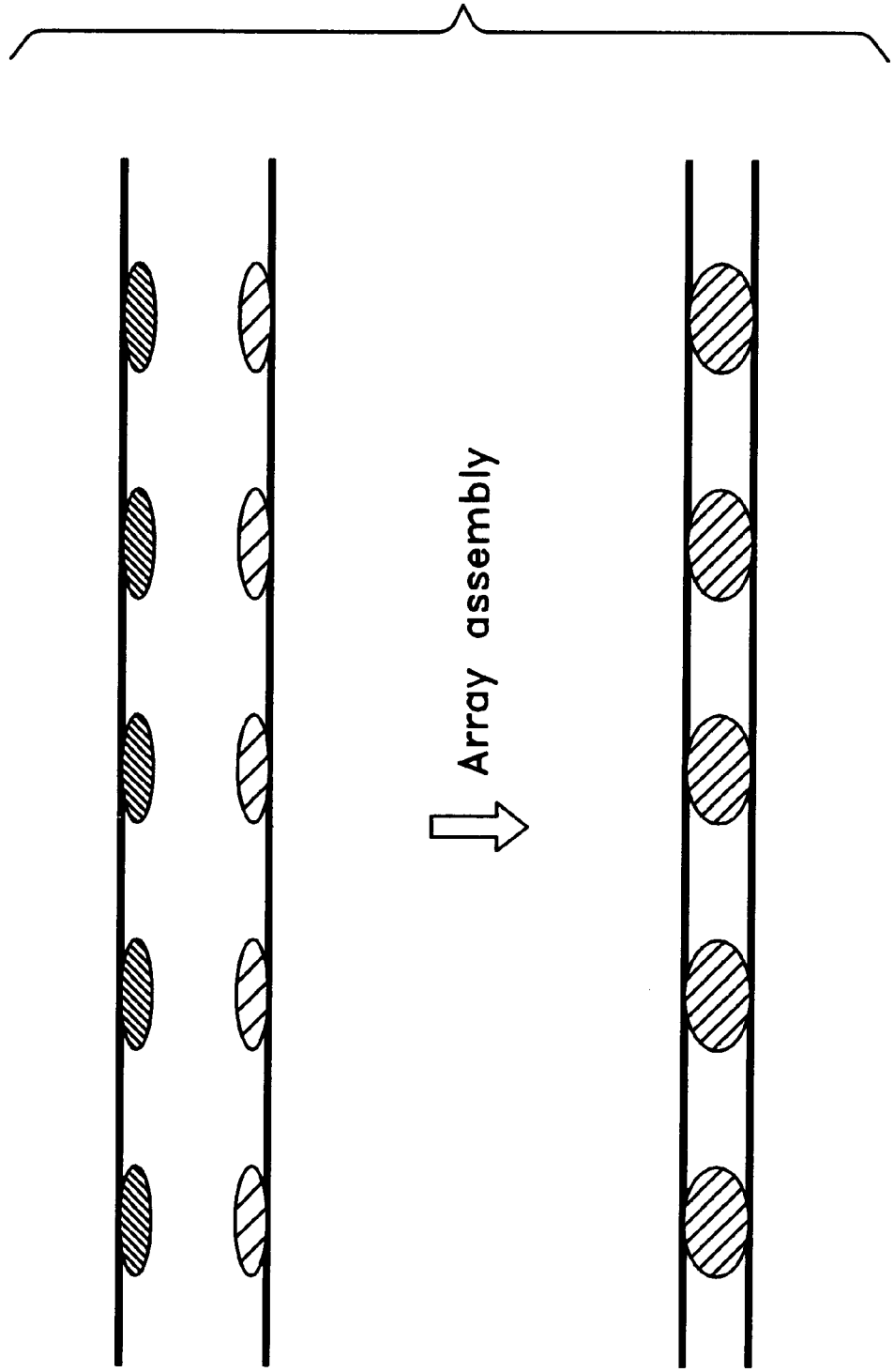
FIG. 1 illustrates the merging of large numbers of microdroplets by bringing two arrays into close apposition.

One of skill in the art will appreciate that reactions compatible with the present method and apparatus are very broad, encompassing all non-unimolecular reactions, i.e., reactions involving two or more reactants. A myriad of chemical and biological reactions may be carried out using the instant method and apparatus. These reactions may involve cells, viruses, nucleic acids, proteins, carbohydrates, lipids, and small molecules, among others. All reactants in a non-unimolecular reaction may be separated into two groups. Each group of reactants comprises one or more reactants, but not all reactants. Therefore, each group alone is not capable of initiating the reaction. Only when one group of reactants is combined with the second group of reactants can the reaction be initiated. One group of reactants may be confined to finite areas on an array, while the other group of reactants may also confined to finite areas on another array. The combination of two groups of reactants is achieved by bringing two arrays into close apposition and allowing the merge of reactants on two arrays (FIG. 1).

While it is convenient that reactants of a reaction is divided into two groups and the reaction is triggered by assembling two reactant-containing arrays, many variations of this method are entirely within the contemplation of the instant invention. For example, reactants may be divided into more than two groups. In a reaction that requires N reactants, up to N groups of reactants may be obtained with each group containing one or more reactants, but not all N reactants. The N groups of reactants may be confined on M arrays ($2 \leq M \leq N$). The reaction may be initiated by successively assembling one of the N groups of reactants on one array with another one of the N groups of reactants on another array until all N reactants are combined. The order of assembling arrays may be decided by factors, such as reactant stability, reaction yields, and convenience among others. It should be noted that arrays containing no reactants may also be assembled with those containing reactants. For example, a washing step may be achieved by assembling with an array containing only the washing solution and no reactant.

Any suitable solid supports (also known as arrays, chips, etc.) may be used in the present invention. These materials include glass, silicon, quartz, nylon, polystyrene, polyethylene, polypropylene, polytetrafluorethylene, metal, among others. These materials typically have a rigid or semi-rigid surface. In some embodiments, at least one surface of the material is substantially flat. Typically, at least one solid support in the assembly is derivatized to provide covalent or noncovalent attachment to chemical or biological entities. Typically, the density of derivatized sites on an array is between about 10–10,000 per $cm^2$, preferably below about 5,000, 1,000, 400, 200, 100, or 60 per $cm^2$. The area of each site may be about $1\times10^{-3}$ to 5 $mm^2$, preferably less than about 2, 1, 0.5, 0.2, or 0.1 $mm^2$. Typically, the total number of derivatized sites on an array is between about 20–1,000,000, preferably, between about 20–500,000, 20–100,000, 20–50,000, 20–10,000, 20–5,000, 20–1,000, or 20–500. In some embodiments, an array may contain raised or depressed regions, e.g., features such as wells, raised regions, etched trenches, etc. The dimensions of these features are flexible, depending on factors, such as desirable reaction concentration, avoidance of air bubbles upon assembly, mechanical convenience and feasibility, etc. For example, the area of a well on an array is in general larger than one derivatized site on another array. The depth of a well may be less than about 1000 microns, preferably less than about 500, 200 or 100 microns.

Figure 2:
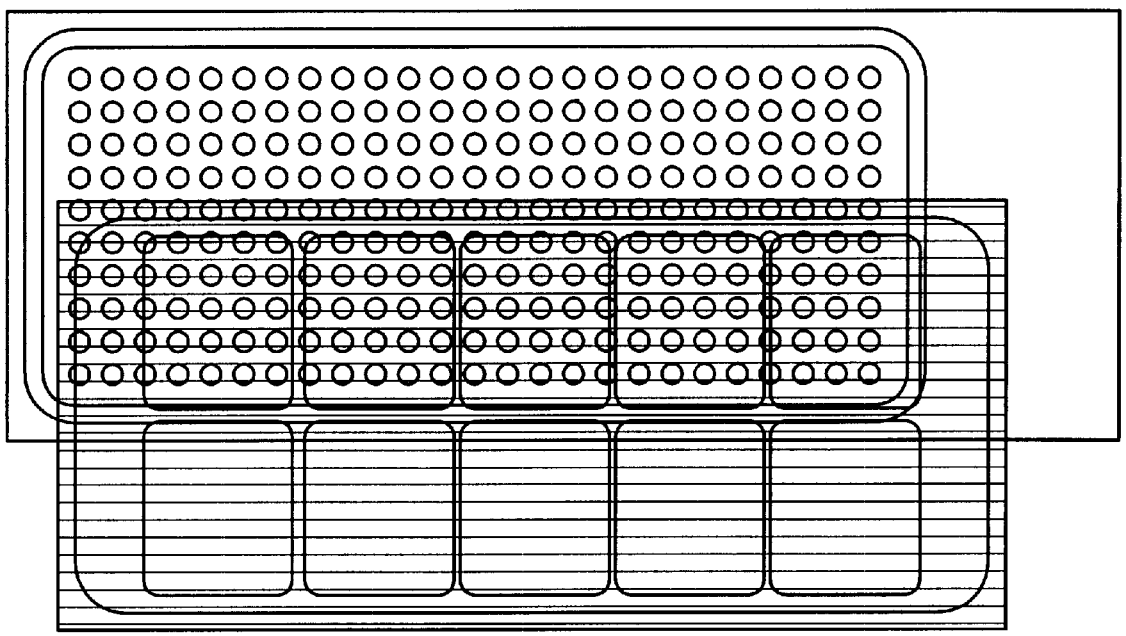
FIG. 2 illustrates array assembly using a first array and a second array (microfabricated with wells) wherein each well of the second array faces a unit cell comprised of two or more reactant-containing areas of the first array.

There are many methods to separate reactants of one reaction from those of another and to prevent reactants of one reaction from entering another reaction before, during, or after assembly. These methods may include mechanical methods, chemical methods, or combinations thereof. For example, large numbers of reaction wells may be microfabricated on the surface of a solid support with each well providing a reaction site (FIG. 2). In some embodiments, the raised regions of reaction wells may be hydrophobic, thus keeping aqueous solution in one reaction well from entering another reaction well upon array assembly. A liquid (such as mineral oil, Fomblin®, etc.) may also be employed to separate reactants of one reaction from those of another. In some embodiments, a liquid polymer (such as Self-Seal®, nail polish, rubber cement, etc.) may be employed as a seal between two arrays or between individual reactions to prevent excess solvent evaporation. Selected areas of a solid support surface may also be chemically or photolytically treated before, during or after assembly to provide separation of reactions. For example, selected areas may be converted from hydrophobic sites to hydrophilic sites upon chemical treatment or photolysis, thus providing separation of aqueous solution of one reaction from another via a hydrophobic matrix. In addition, reaction volumes are typically small. Microdroplets are not substantially affected by gravity and their local movements are limited. Array assembly may also be accomplished in the absence of microdroplets. For example, the reactant-containing solutions on arrays may be dried or frozen before or during the array assembly.

Figure 3:
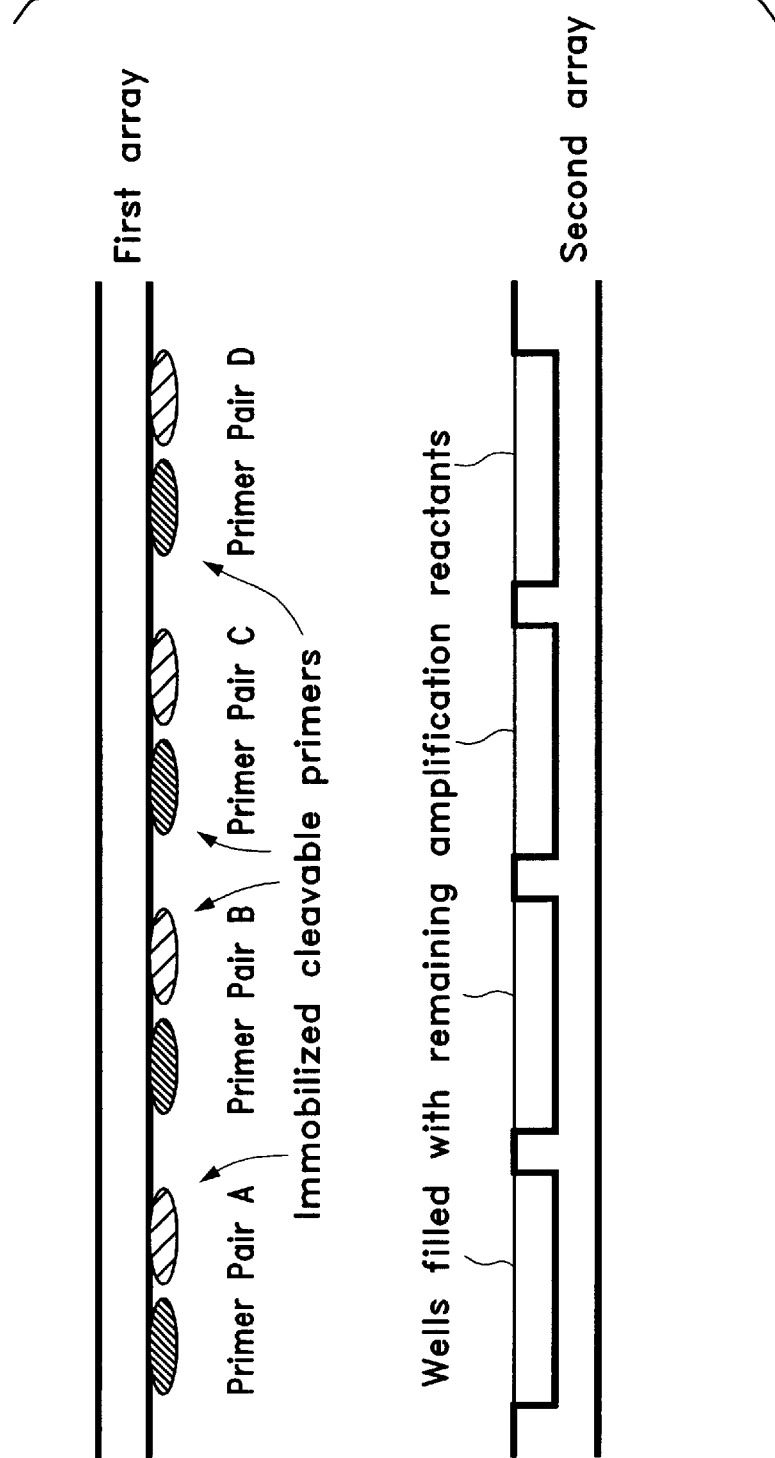
FIG. 3 illustrates two arrays each containing reactants of polynucleotide amplification reactions. Large numbers of polynucleotide amplification reactions may be initiated by bringing two arrays into close apposition and merging all reactants on two arrays. In this illustration, a cleavable primer pair with different sequences (e.g., a forward primer and a reverse primer) are immobilized on two areas of the first array. Upon array assembly, the forward and reverse amplification primers are released to merge with the remaining amplification reactants in a reaction well on the second array. Each reaction well represents a different amplification using either different primer pairs or different target nucleic acid sequence.

In one embodiment of the instant invention, polynucleotide amplification reactions may be performed by bring at least two arrays into close apposition and allowing reactants of polynucleotide amplification reactions on two arrays to come in contact. All reactants in a polynucleotide amplification reaction may be separated into at least two groups. Each group of reactants comprises one or more reactants, but not all reactants. Therefore, each group alone is not capable of initiating a polynucleotide amplification reaction. Only when one group of reactants is combined with the second group of reactants can the reaction be initiated. In preferred embodiments of the instant invention, one group of reactants may be located on one or more areas on an array, while the other group of reactants may be located on one or more areas on another array. The combination of two groups of reactants is achieved by bringing two arrays into close apposition and allowing the contact of reactants on two arrays. For example, a typical PCR amplification reaction involves several reactants, including a target nucleic acid, deoxynucleotide triphosphates, two primers, a DNA polymerase, and a buffer. One group of PCR reactants may comprise two primers. The second group of reactants may comprise the remaining reactants, including a target nucleic acid, deoxynucleotide triphosphates, a DNA polymerase, and a buffer. Neither the first nor the second group of reactants alone can start the PCR amplification reaction, because the requisite reactants are missing in each group. Only when the first group is combined with the second group, i.e. when all requisite reactants are present, can the PCR reaction be initiated and performed (FIG. 3). Of course, reactants may be grouped together in many different ways. For example, only one primer may be included in the first group and the second group of reactants may comprise the remaining reactants, including a target nucleic acid, deoxynucleotide triphosphates, the other primer, a DNA polymerase, and a buffer. It is also possible that selected reactants may be present in both groups of reactants. For instance, a buffer may be included in both the first group of reactants and the second group of reactants.

The large numbers of polynucleotide amplification reactions performed between two arrays may use similar or different target nucleic acid sequences. In some embodiments, the same target nucleic acid may be present in each reaction. But different primer sequences specific for different regions of the target sequence are immobilized on one array. Therefore, each polynucleotide amplification reaction represents the amplification of a different region of the target sequence. In other embodiments, different target nucleic acid sequence may be present in each reaction. But similar set of primers specific for the same region of the target sequence are immobilized on the first array. Each polynucleotide amplification reaction thus represents amplification of the same region of target sequences from different sources. Of course, a combination of both embodiments is applicable using the instant invention.

The array assembly method provides an environment for simultaneously carrying out between about 10–500,000 reactions, preferably, above about 20, 50, 100, 200, 500, 1,000, 5,000, 10,000, 50,000, or 100,000 reactions. The advantages of the present method and apparatus are many folds. First, multiplexing gives simultaneous results of many reactions and generates large amounts of information per unit time. Second, performing large numbers of similar reactions in parallel increases the accuracy of comparative analysis by eliminating factors such as array-to-array variations, differences in reaction conditions, among others.

II. Immobilization of Reactants on Arrays

In some embodiments of the instant invention, one or more reactants may be immobilized on an array prior to array assembly. The immobilization may be covalent or non-covalent. For example, one or more reactants may be tethered to an immobilized moiety on the array. In certain embodiments of the instant invention, one or more reactants may be immobilized on an array via a releasable site, for example by tethering to an immobilized molecule with a releasable site. The immobilized reactants may be released from an array upon reacting with cleaving reagents prior to, during or after the array assembly. The release methods may include a variety of enzymatic, or non-enzymatic means, such as chemical, thermal, or photolytic treatment.

For example, in performing large numbers of polynucleotide amplification reactions, at least one primer may be tethered to an immobilized moiety with a releasable site on the surface of a first array. The remaining reactants of a polynucleotide amplification reaction may be confined to finite areas on the surfaces of a second array, e.g., in reaction wells designed to house reactants of a polynucleotide amplification reaction. If two arrays with matched primer-containing regions and reaction wells are brought into close apposition, reactants on two arrays may merge. The primers may be released before, during or after the merging of reactants, thereby triggering reactions by mixing the requisite primers with the remaining reactants in the reaction well. Therefore, in a single physical operation, i.e., assembling two reactant-containing arrays, hundreds of thousands of separate reactions are initiated and performed.

As an example of primer release, primers may be initially hybridized to array-immobilized polynucleotides and subsequently released by strand separation from the array-immobilized polynucleotides upon array assembly. In another example of primer release, one or more primers of polynucleotide amplification reactions may be covalently immobilized on an array via a cleavable site and released before, during, or after array assembly. For example, an array-immobilized moiety may contain a cleavable site and a primer sequence. The primer sequence may be released via selective cleavage of the cleavable sites before, during, or after assembly. Typically, the immobilized moiety may itself be a polynucleotide which contains one or more cleavable sites and one or more primer polynucleotides. A cleavable site may be introduced in an immobilized moiety during in situ synthesis. Alternatively, the immobilized moieties containing releasable sites may be prepared before they are covalently or noncovalently immobilized on the solid support.

A. Array fabrication

Any suitable solid supports (also known as arrays, chips, etc.) may be used in the present invention. These materials include glass, silicon, quartz, nylon, polystyrene, polyethylene, polypropylene, polytetrafluorethylene, metal, among others. These materials typically have a rigid or semi-rigid surface. In some embodiments, at least one surface of the material is substantially flat. In some embodiments, these materials may contain raised or depressed region, e.g., features such as wells, raised regions, etched trenches, etc. Typically, at least one solid support in the assembly is derivatized to provide covalent or noncovalent attachment to chemical or biological entities. Typically, the density of derivatized sites on an array is between about 10–10,000 per $cm^2$, preferably below about 5,000, 1,000, 400, 200, 100, or 60 per $cm^2$. The area of each site may be about $1\times10^{-3}$ to 5 $mm^2$, preferably less than about 2, 1, 0.5, 0.2, or 0.1 $mm^2$. Typically, the total number of derivatized sites on an array is between about 20–1,000,000, preferably, between about 20–500,000, 20–100,000, 20–50,000, 20–10,000, 20–5,000, 20–1,000, or 20–500.

In preferred embodiments of the instant invention, surface tension arrays, which comprise patterned hydrophilic and hydrophobic sites, may be employed. A surface tension array may contain large numbers of hydrophilic sites against a hydrophobic matrix. A hydrophilic site typically includes free amino, hydroxyl, carboxyl, thiol, amido, halo, or sulfonate group, as well as modified forms thereof, such as activated or protected forms. A hydrophobic site is typically inert to conditions of in situ synthesis. For example, a hydrophobic site may include alkyl, fluoro group, as well as modified forms thereof, etc. In surface tension arrays, a hydrophilic site is spatially segregated from neighboring hydrophilic sites because of the hydrophobic sites between hydrophilic sites. This spatially addressable pattern enables the precise and reliable location of chemical or biological entities, such as molecules, cells, viruses, etc. The free amino, hydroxyl, carboxyl, thiol, amido, halo, or sulfonate group of the hydrophilic sites may then be covalently coupled with a linker moiety (e.g., polylysine, HEG, PEG, etc.) capable of supporting chemical and biological synthesis. The hydrophilic sites may also support non-covalent attachment to chemical or biological entities, such as molecules, cells, viruses, etc. Reagents delivered to the array are constrained by surface tension difference between hydrophilic and hydrophobic sites.

The surface tension array may also be appreciated from a thermodynamic perspective of wetting. Surface tension results from an imbalance of molecular forces in a liquid. At the surface of a liquid, the liquid molecules are attracted to each other and exert a net force pulling themselves together. High values of surface tension means that molecules tend to interact strongly. Lower values mean that molecules do not interact as strongly. Water has a very high value of surface tension because it has a high degree of hydrogen bonding. Organic molecules with polar groups such as hydroxyl, carboxyl or cyano have a slightly lower surface energy than water. Pure hydrocarbons are even lower, while fluorinated compounds are very low, because the fluorine atom does not share electrons very well so only dispersion interactions (entropy of mixing) occur.

Molecules in a liquid state experience strong intermolecular attractive forces. These cohesive forces between liquid molecules are responsible for the phenomenon known as surface tension. Molecules at the surface of a liquid droplet do not have other like molecules, and as a consequence cohere more strongly with adjacent molecules which are directly associated them.

When the attractive forces are between unlike molecules, they are described as adhesive forces. The adhesive force between a water molecule and the wall of a glass capillary (i.e., the SiOH group) is stronger than the cohesive force between two water molecules at the surface. The effect of this imbalance between adhesion and cohesion is that the meniscus will turn upward and contribute to capillary action. Conversely, for mercury, the cohesive force between two mercury atoms is stronger than the adhesive force between mercury and glass, and the meniscus turns down at the wall.

When a liquid is in contact with a solid surface, the contact angle θ may be used to quantitatively measure the extent of this interaction.

$$\gamma_{SV} - \gamma_{SL} = \gamma_{LV} \cos\theta$$

where $\gamma_{SV}$ is the surface free energy of the solid, $\gamma_{SL}$ is the interfacial free energy between the solid and the liquid, $\gamma_{LV}$ is the surface free energy of the liquid.

When a droplet of liquid is in contact with a surface which is patterned into two regions which have different surface energies, then there is a net attraction of the liquid into the region of higher surface energy. The droplet may move, as a result of the difference in surface tension between the two regions.

In other words, polar liquids wet polar surfaces in preference to nonpolar surfaces. For a patterned array where the polar synthesis regions (hydrophilic sites) are separated by nonpolar regions (hydrophobic sites), droplets of liquid are confined to a particular synthesis site, and will not migrate to an adjacent site because of the surface tension difference imposed by the nonpolar mask.

For surface tension arrays, hydrophilic sites are derivarized sites. Typically, the density of hydrophilic sites on an array is between about 10–10,000 per cm$^2$, preferably below about 5,000, 1,000, 400, 200, 100, or 60 per cm$^2$. The area of each hydrophilic site may be about $1 \times 10^{-3}$ to 5 mm$^2$, preferably less than about 2, 1, 0.5, 0.2, or 0.1 mm$^2$. Typically, the total number of hydrophilic sites on an array is between about 20–1,000,000, preferably, between about 20–500,000, 20–100,000, 20–50,000, 20–10,000, 20–5,000, 20–1,000, or 20–500.

A number of methods for fabricating surface tension arrays have been described in U.S. Pat. Nos. 5,985,551 and 5,474,796. One of such methods involves coating a solid surface with a photoresist substance and then using a generic photomask to define the array patterns by exposing them to light. The exposed surface may then be reacted with a suitable reagent to form a stable hydrophobic matrix. For example, fluoroalkylsilane or long chain alkylsilane, such as octadecylsilane, may be employed to form a hydrophobic matrix. The remaining photoresist substance may then be removed and the solid support may react with a suitable reagent, such as aminoalkyl silane or hydroxyalkyl silane, to form hydrophilic regions.

The solid support may also be first reacted with a suitable derivatizing reagent to form a hydrophobic surface. For example, the hydrophobic surface may be derivatized by vapor or liquid treatment of fluoroalkylsiloxane or alkylsilane. The hydrophobic surface may then be coated with a photoresist substance, photopatterned and developed. The exposed hydrophobic surface may be reacted with suitable derivatizing reagents to form hydrophilic sites. For example, the exposed hydrophobic surface may be removed by wet or dry etch such as oxygen plasma and then derivatized by aminoalkylsilane or hydroxylalkylsilane treatment to form hydrophilic sites. The photoresist coat may be removed to expose the underlying hydrophobic sites. The hydrophilic sites may be further functionalized, if necessary, for anchoring in situ synthesis or for depositing chemical or biological entities.

Alternatively, the solid support may be first reacted with a suitable derivatizing reagent to form a hydrophilic surface. For example, the hydrophilic surface may be derivatized by vapor or liquid treatment of aminoalkylsilane or hydroxylalkylsilane. The derivatized surface may then be coated with a photoresist substance, photopatterned, and developed. The exposed surface may be reacted with suitable derivatizing reagents to form hydrophobic sites. For example, the hydrophobic sites may be formed by fluoroalkylsiloxane or alkylsilane treatment. The photoresist coat may be removed to expose the underlying hydrophilic sites. The hydrophilic sites may be further functionalized, if necessary, for anchoring in situ synthesis or for depositing chemical or biological entities.

Variations of these procedures may also be used to fabricate a solid support surface such that solution of reactants at a derivatized site is spatially separated from solution of reactants at other derivatized sites by surface tension. Separate reactions may be carried out at each derivatized site.

Photoresist substances are readily known to those of skill in the art. For example, an optical positive photoresist substance (e.g., AZ 1350 (Novolac™ type-Hoechst Celanese™) (Novolac™ is a proprietary novolak resin, which is the reaction product of phenols with formaldehyde in an acid condensation medium)) or an E-beam positive photoresist substance (e.g., EB-9 (polymethacrylate by Hoya™)) can be used.

Suitable hydrophilic and hydrophobic derivatizing reagents are also well known in the art. Preferably, fluoroalkylsilane or alkylsilane may be employed to form a hydrophobic surface and aminoalkyl silane or hydroxyalkyl silane may be used to form hydrophilic sites. As an example, a number of siloxane derivatizing reagents are listed below:

1. Hydroxyalkyl siloxanes (Silylate surface, flnctionalize with diborane, and $H_2O_2$ to oxidize the alcohol)
   a. allyl trichlorochlorosilane→→3-hydroxypropyl
   b. 7-oct-1-enyl trichlorochlorosilane→→8-hydroxyoctyl
2. Diol (bis-hydroxyalkyl) siloxanes (silylate surface, and hydrolyze to diol)
   a. glycidyl trimethoxysilane→→(2,3-dihydroxypropyloxy)propyl
3. Aminoalkyl siloxanes (amines require no intermediate functionalizing step)
   a. 3-aminopropyl trimethoxysilane→3-aminopropyl
4. Dimeric secondary aminoalkyl siloxanes
   a. bis (3-trimethoxysilylpropyl) amine→bis (silyloxylpropyl)amine Glass (polytetrasiloxane) is particularly suitable for surface tension arrays, because of the numerous techniques developed by the semiconductor industry using thick films (1–5 microns) of photoresists to generate masked patterns of exposed glass surfaces. After sufficient cleaning, such as by treatment with $O_2$ radical (e.g., using an $O_2$ plasma etch, ozone plasma treatment, etc.) followed by acid wash, the glass surface may be derivatized with a suitable reagent to form a hydrophilic surface. Suitable reagents may include aminoalkyl silane, hydroxyalkyl silane, among others. In particular, glass surface may be uniformly aminosilylated with an aminosilane, such as aminobutyldimethylmethoxysilane (DMABS). The derivatized surface may then be coated with a photoresist substance, soft-baked, photopatterned using a generic photomask to define the array patterns by exposing them to light, and developed. The underlying hydrophilic sites are thus exposed in the mask area and ready to be derivatized again to form hydrophobic sites, while the photoresist covering region protects the underlying hydrophilic sites from further derivatization. Suitable reagents, such as fluoroalkylsilane or long chain alkylsilane, may be employed to form hydrophobic sites. For example, the exposed hydrophilic sites may be burned out with an $O_2$ plasma etch. The exposed regions may then be fluorosilylated. Following the hydrophobic derivatization, the remaining photoresist can be removed, for example by dissolution in warm organic solvents such as methyl isobutyl ketone or N-methyl pyrrolidone (NMP), to expose the hydrophilic sites of the glass surface. For example, the remaining photoresist may be dissolved off with sonication in acetone and then washed off in hot NMP.

A number of organic polymers also have desirable characteristics for surface tension arrays. For example, Teflon (polytetrafluoroethylene) may be used. Patterned derivatization of this type of material may be accomplished by reactive ion or plasma etching through a physical mask or using an electron beam, followed by reduction to surface hydroxymethyl groups. Polypropylene/polyethylene may be surface derivatized by gamma irradiation or chromic acid oxidation, and converted to hydroxy or aminomethylated surfaces. Highly crosslinked polystryene-divinylbenzene (ca. 50%) is non-swellable, and may be readily surface derivatized by chloromethlylation and subsequently converted to other functional groups. Nylon provides an initial surface of hexylamino groups, which are directly active. The hydrophobic patterning of these surfaces may be effected using the same type of solution based thin film masking techniques and gas phase derivatization as glass, or by direct photochemical patterning using o-nitrobenzylcarbonyl blocking groups. Perfluoroalkyl carboxylic and sulfonic acid derivatives are now used to provide the hydrophobic mask of the underlying surface. Subsequent to the patterning of these surfaces, suitable linker moieties may be coupled to the reactive group such as the hydroxy or amino group.

In addition to the use of photoresist in generating patterned hydrophilic and hydrophobic sites, surface tension arrays may be fabricated without the use of photoresist. For example, a solid support may be first reacted with a reagent to form hydrophilic sites. The hydrophilic sites may then be reacted in selected areas. The remaining hydrophilic sites may then be reacted with a reagent to form hydrophobic sites. The protected hydrophilic sites may then be deprotected to anchor in situ synthesis or to deposit chemical or biological entities. For example, a glass surface may be first reacted with a reagent to generate free hydroxyl or amino sites. These hydrophilic sites may be reacted with a protected nucleoside coupling reagent or a linker to protect selected hydroxyl or amino sites. A protected nucleotide coupling reagent includes, for example, a DMT-protected nucleoside phosphoramidite, DMT-protected H-phosphonate, etc. A linker may be of six or more atoms in length. The unprotected hydroxyl or amino sites may then be reacted with a reagent, for example, perfluoroalkanoyl halide, to form hydrophobic sites inert to in situ polynucleotide synthesis. The protected hydrophilic sites may be deprotected to anchor in situ polynucleotide synthesis. Variations of these procedures may also be used to fabricate a solid support surface such that solution of chemical or biological entities at a derivatized site is spatially separated from solutions of chemical or biological entities at other derivatized sites.

In addition to surface tension array, many other examples of arrays and fabrication methods are well known to those skilled in the art (e.g., Green et al., *Curr.Opin. in Chem. Biol* 2:404–410 (1998), Gerhold et al., *TIBS*, 24:168–173 (1999), U.S. Pat. Nos. 6,090,995, 6,030782, 5,700,637, 6,054,270, 5,919,626, 5,858,653, 5,837,832, 5,744,305, 5,445,934, WO099/8708 Singh-Gasson et al., *Nature Biotechnology* 17:974–978 (1999), all incorporated herein by reference). They include, for example, fiber optic arrays, microelectrode arrays, digital micromirror arrays, etc.

B. Covalent or noncovalent immobilization of reactants on arrays

One of skill in the art will appreciate that there are many ways of immobilizing chemical or biological moieties directly on an array (covalently or noncovalently), anchoring them to a linker moiety, or tethering them to an immobilized moiety. These methods are well taught in the field of solid phase synthesis and micro-arrays (Protocols for oligonucleotides and analogs; synthesis sand properties, *Methods Mol. Biol.* Vol. 20 (1993), Beier et al., *Nucleic Acids Res.* 27:1970–1–977 (1999), Joos et al., *Anal. Chem.* 247:96–101 (1997), Guschin et al., *Anal. Biochem.* 250:203–211 (1997), U.S. Pat. Nos. 5,700,642 and 5,830,655, Czarnik et al., *Accounts Chem. Rev.* 29:112–170 (1996), *Combinatorial Chemistry and Molecular Diversity in Drug Discovery*, Ed. Kerwin J. F. and Gordon, E. M., John Wiley & Son, New York (1997); Kahn et al., *Modern Methods in Carbohydrate Synthesis*, Harwood Academic, Amsterdam (1996), Green et al., *Curr.Opin. in Chem. Biol.* 2:404–410 (1998), Gerhold et al., *TIBS*, 24:168–173 (1999), U.S. Pat. Nos. 6,0901995, 6,083,763, 6,030,782, 5,700,637, 6,054,270, 5,919,626, 5,858,653, 5,837,832, 5,744,305, 5,445,934, WO99/58708, DeRisi, J., et al., *Science* 278:680–686 (1997), Lockhart et al., *Nature* 405:827–836 (2000), Roberts et al., *Science* 287:873–880 (2000), Hughes et al., *Nature Genetics* 25:333–337 (2000), Hughes et al., *Cell* 102:109–126 (2000), Duggan, et al., *Nature Genetics Supplement* 21:10–14 (1999), and Singh-Gasson et al., *Nature Biotechnology* 17:974–978 (1999), and all incorporated herein by reference). Exemplary chemical moieties for immobilization attachment to solid support include carbamate, ester, amide, thiolester, (N)-functionalized thiourea, functionalized maleimide, amino, disulfide, amide, hydrazone, streptavidin or avidin/biotin, and gold-sulfide, among others. The immobilization methods generally fall into one of the two categories: spotting of presynthesized reactants and in situ synthesis of reactants.

In the first category, preprepared reactants are deposited onto known finite areas on an array. For example, traditional solid phase polynucleotide synthesis on controlled-pore glass (CPG) may also be employed and then simply printing presynthesized polynucleotides onto the array using direct touch or fine micropipetting. Polynucleotides may be synthesized on an automated DNA synthesizer, for example, on an Applied Biosystems synthesizer using 5-dimethoxytritylnucleoside β-cyanoethyl phosphoramidites. Synthesis of relatively long polynucleotide sequences may be achieved by PCR-based and/or enzymatic methods for economical advantages. Polynucleotides may be purified by gel electrophoresis, HPLC, or other suitable methods known in the art before spotted or deposited on the solid support. Typical non-covalent linkages may include electrostatic interactions, ligand-protein interactions (e.g., biotin/streptavidin or avidin interaction), and base-specific hydrogen bonding (e.g., complementary base pairs), among others. Solid supports may be overlaid with a positively charges coating, such as amino silane or polylysine and presynthesized polynucleotides are then printed directly onto the solid surface.

In addition, presynthesized compounds, such as polypeptides, polynucleotides, polysaccharides, or small molecule libraries, may be obtained commercially, such as from Integrated DNA Technologies, ArQule Chembridge, and Combichem. These presynthesized compounds may be covalently or non-covalently attached to the array surface.

Methods are also available to immobilize cells or proteins on solid supports (Mrksich et al., *Ann. Rev. Biophys. Biomol. Struct.* 25:55–78 (1996), U.S. Pat. Nos. 5,989,835 and 6,103,479, WO 97/45730, WO98/38490, WO00/50872, WO00/26408, WO00/17643, WO00/17624, WO0003246). In particular, Mrkisch et al. (*Proc. Natl. Acad. Sci. USA* 93:10775–8 (1996), all incorporated herein by reference) describe a method for attaching cells on gold with self-assembled monolayers of alkanethiolates. Singhvi et al. (*Science* 264:696–698 (1994)) describe a method for placing cells on predetermined locations of an array and controlling cell shape.

Printing may be accomplished by direct surface contact between the printing reagents and a delivery mechanism.

The delivery mechanism may contain the use of tweezers, pins or capillaries, among others that serve to transfer reactants or reagents to the surface. A variation of this simple printing approach is the use of controlled electric fields to immobilize prefabricated charged reactants to microelectrodes on the array (e.g. U.S. Pat. No. 5,929,208 and WO 99/06593, both incorporated herein by reference). For example, biotinylated polynucleotide probes may be directed to individual spots by polarizing the charge at that spot and then anchored in place via a steptavidin-containing permeation layer that covers the surface (Sosnowski et al., *Proc. Natl. Acad. Sci.* 94:1119–1123 (1997) and Edman et al., *Nucleic Acid. Res.* 25:4907–4914 (1997), both incorporated herein by reference). Print may also be accomplished without the direct contact with the solid support, such as using the "drop-on-demand" method described below. Some of the advantages of spotting technologies include ease of prototyping and therefore rapid implementation, low cost and versatility.

In the second category, reactants are prepared by in situ synthesis on the array. In situ synthesis may be performed on derivatized sites. Derivatized sites thus become in situ synthesis sites. Typically, the density of in situ synthesis sites on an array is between about 10–10,000 per $cm^2$, preferably below about 5,000, 1,000, 400, 200, 100, or 60 per $cm^2$. The area of each in situ synthesis site may be about $1 \times 10^{-3}$ to 5 $mm^2$, preferably less than about 2, 1, 0.5, 0.2, or 0.1 $mm^2$. Typically, the total number of in situ synthesis sites on an array is between about 20–1,000,000, preferably, between about 20–500,000, 20–100,000, 20–50,000, 20–10,000, 20–5,000, 20–1,000, or 20–500.

Small molecules may be prepared on the array using standard solid phase organic synthesis methods. Biopolymers such as polynucleotides, polypeptides, and polysaccharides may be synthesized from biochemical building blocks such as nucleotides, amino acids, and monosaccharides in a step-wise fashion. With each round of synthesis, these building blocks are added to growing chains until the desired sequence and length are achieved in each spot. In general, in situ biopolymer synthesis on an array may be achieved by two general approaches. First, photolithography may be used to fabricate biopolymers on the array. In the case of polynucleotides, a mercury lamp may be shone through a photolithograhic mask onto the array surface, which removes a photoactive group, resulting in a 5' hydroxy group capable of reacting with another nucleoside. The mask therefore predetermines which nucleotides are activated. Successive rounds of deprotection and chemistry result in polynucleotides with increasing length. This method is disclosed in, e.g., U.S. Pat. Nos. 5,143,854, 5,489,678, 5,412,087, 5,744,305, 5,889,165, and 5,571,639, all incorporated herein by reference.

The second approach is the "drop-on-demand" method, which uses technology analogous to that employed in ink-jet printers (U.S. Pat. Nos. 5,985,551, 5,474,796, 5,700,637, 6,054,270, 6,028,189, 5,927,547, WO 98/41531, Blanchard et al., *Biosensors and Bioelectronics* 11:687–690 (1996), Schena et al., *TIBTECH* 16:301–306 (1998), Green et al., *Curr. Opin. Chem. Biol.* 2:404–410 (1998), and Singh-Gasson, et al., *Nat. Biotech.* 17:974–978 (1999), all incorporated herein by reference). This approach typically utilizes piezoelectric or other forms of propulsion to transfer reagents from miniature nozzles to solid surfaces. For example, the printer head travels across the array, and at each spot, electric field contracts, forcing a microdroplet of reagents onto the array surface. Following washing and deprotection, the next cycle of biopolymer synthesis is carried out. In the case of polynucleotides, the step yields in piezoelectric printing method typically equal to, and even exceed, traditional CPG polynucleotide synthesis. The drop-on-demand technology allows high-density gridding of virtually any reagents of interest. It is also easier using this method to take advantage of the extensive chemistries already developed for biopolymer and small molecule synthesis, for example, flexibility in sequence designs, synthesis of polynucleotide analogs, synthesis in the 5'–3' direction, etc. Because ink jet technology does not require direct surface contact, piezoelectric delivery is amendable to very high throughput. An average step yields near or above about 98% in in situ polynucleotide synthesis may be obtained. Similar methods of reagent delivery using a tip of a spring probe are described in WO 99/05308, incorporated herein by reference.

In preferred embodiments, a piezoelectric pump may be used to add reagents to the in situ synthesis of primer-containing moieties on arrays. The design, construction, and mechanism of a piezoelctric pump are described in U.S. Pat. No. 4,747,796. The piezoelectric pump may deliver minute droplets of liquid to a surface in a very precise manner. The pump design is similar to the pumps used in ink jet printing. The picopump is capable of producing 50 micron or 65 picoliter droplets at up to 10,000 Hz and can accurately hit a 250 micron target at a distance of 2 cm.

Methods for solid phase synthesis of large combinatorial peptide libraries have been described in the literature (Merrifield, *Science* 232:342–347 (1986), Atherton et al., *Solid Phase Peptide Synthesis*, IRL press, London (1989), Albericio et al., *Methods Enzymol.* 289:313–316 (1997), and U.S. Pat. Nos. 5,614,608 and 5,679,773, all incorporated herein by reference). Typically, a growing polypeptide chain is covalently anchored to a solid support and amino acids are added to the support-bound growing chain in a stepwise fashion. In order to prevent unwanted polymerization of the monomeric amino acid under the reaction conditions, protection of the N-terminus of the amino acid and α-amino group using blocking groups, such as tert-butyloxycarbonyl (Boc), fluorenylmethyloxycarbonyl (Fmoc) and the like, is necessary. After the monomer is coupled to the end of the polypeptide, the N-terminal protecting group is removed, and another amino acid is coupled to the chain. This cycle of coupling and deprotecting is continued for each amino acid until the desired length is reached. Photoremovable protecting group may be used to allow removal of selected portion of the solid support, via patterned irradiation, during the deprotection cycle of the solid phase synthesis (Fodor, et al., *Science* 251:767–773 (1991) and U.S. Pat. Nos. 5,143, 854, 5,489,678, and 5,744,305, all incorporated herein by reference.) This selectively allows spatial control of the synthesis and the next amino acid is coupled to the irradiated areas. In addition to standard solid phase peptide synthesis, PCT publication WO 99/06834, incorporated herein by reference, describes a method for immobilizing a diverse population of antibodies to a solid support.

Libraries of carbohydrate compounds may also be prepared on a solid support (Ito et al., *Curr. Opin. Chem. Biol.* 2:701–708 (1998), incorporated herein by reference). In solid-phase polysaccharide synthesis, elongation of a carbohydrate compounds generally consists of two steps: coupling of the glycosyl acceptor with the glycosyl donor, and selective deprotection of a temporary protecting group to liberate the free hydroxyl group that will be subjected to the next coupling with a glycosyl donor. At the final stage of polysaccharide synthesis, all protecting groups are removed. The first carbohydrate residue is typically attached to the solid support via a linker molecule and the residual hydroxyl groups are capped after each step. Stable nonclassical glycosyl donors may be utilized and they may be activated under specific conditions (Toshima et al., *Chem. Rev.* 93:1503–1531 (1993), incorporated herein by reference). Sulfoxide methods developed by Kahn et al. may be used for stereoselective glycosylation of alcohol group (Yan et al., *J. Am. Chem. Soc.* 116:6953–6954 (1994), incorporated herein by reference). Trichoroacetimidate, thioglycoside, n-pentenyl glycoside are also amendable to solid phase synthesis (Rademann et al., *J. Org. Chem.* 62:3650–3653 (1997), Heckel et al., *Synlett* 171–173 (1998), Nicolaou et al., *J. Am. Chem. Soc.* 119:449–450 (1998), Rodebaugh et al., *J. Org. Chem.* 62:5660–5661 (1997), Danishefsky et al., *Science* 260:1307–1309 (1993); and Zheng et al., *J. Org. Chem.* 63:1126–1130 (1998), all incorporated herein by reference). In addition, PCT publication 98/22487, incorporated herein by reference, describes methods for synthesizing very large collections of diverse thiosaccharide derivatives attached to a solid support. U.S. Pat. No. 5,846,943 and PCT publication WO 98/21221, incorporated herein by reference, describe novel solid support matrices having toxin-binding polysaccharide covalently attached to a solid support through a linker arm. In addition to chemical synthesis, enzymatic synthesis of polysaccharides, such as glycosyltransferase-catalyzed glycosylation, has also been proved feasible (Shuster et al., *J. Am. Chem. Soc.* 116:1135–1136 (1994), Yamada et al., *Tetrahedron Lett.* 36:9493–9496 (1995), and Blixt et al., *J. Org. Chem.* 63:2705–2710 (1998), all incorporated herein by reference).

Chemical synthesis of glycopeptide may also be carried out on a solid support (Meldal et al. *Curr. Opin. Chem. Biol.* 1:552–563 (1997) and Kihlberg et al., *Methods Enzymol.* 289:221–245 (1997), both incorporated herein by reference). Frequently, glycosylated amino acids are used as building blocks (Gururaja et al., *Lett Pept. Sci.* 3:79–88 (1996); Mcdevitt et al. *J. Am. Chem. Soc.* 118:3818–3828 (1996), and Paulsen et al., *J. Chem. Perkin Trans* 1:281–293 (1997), all incorporated herein by reference).

The synthesis of small organic compounds on a solid support is also well known in the art of solid phase organic synthesis (Gordon et al., *J. Med. Chem.* 37:1385–1401 (1994); Lowe, *Acc. Chem. Res.* 24:309–317 (1995), Fruchtel, *Angew. Chem. Int. Ed. Engl.* 35:17–42 (1996), Hermkens et al., *Tetrahedron* 52:4527–4554 (1996), Thompson et al., *Chem. Rev.* 96:555–600 (1996), and Andres, et al., *Curr. Opin. Chem. Biol.* 2:353–362 (1998), all incorporated herein by reference). In particular, PCT publication WO99/09073, incorporated by reference, describes methods of carrying out organic chemistry on solid supports comprising derivatized functionalities and methods for synthesizing compounds comprising amine group or N-containing heterocycles using functionalized solid support. U.S. Pat. No. 5,545,568, incorporated herein by reference, describes a general methodology for synthesizing combinatorial libraries of various nonpolymeric compounds on solid supports, such as benzodiazepine, prostaglandins, β-turn mimetics and glycerol-derived drugs. PCT publication WO 97/35198, incorporated herein by reference, describes methods for synthesizing spatially-dispersed and positionally-encoded combinatorial chemistry libraries of oligomers. The position of each solid support in each array determines the exact identity of the oligomers. This method is very useful for the synthesis of a peptide library and a non-peptide, low molecular weight organic compound libraries. PCT publication WO 98/46247, incorporated herein by reference, describes a method for immobilizing immunosupressive agent, such as cyclosporin analogs on a solid support. PCT publication WO 99/21957, incorporated herein by reference, discloses methods for generating libraries of organometallic catalysts on solid support.

C. Immobilization of reactants with releasable sites

In some embodiments of the instant invention, reactants may be first immobilized on an array and subsequently released prior to, during, or after array assembly. For example, reactants may be delivered via selective cleavage of a cleavable site on an array-immobilized moiety. A releasable site may be introduced in immobilized moieties using standard nucleic acid, peptide, carbohydrate, lipid, or organic chemistry known to one of skill in the art. The release methods may include a variety of enzymatic, or non-enzymatic means, such as chemical, thermal, or photolytic treatment.

In the case of polynucleotides, the synthesis of many modified polynucleotides containing cleavable sites is well known in the art of polynucleotide synthesis (Verma et al., *Annu. Rev. Biochem.* 67:99–134 (1998), Venkatesan et al. *J. of Org. Chem.,* 61:525–529 (1996), Kahl et al., *J. of Org. Chem.,* 64:507–510 (1999), and Kahl et al., *J. of Org. Chem.* 63:4870–4871 (1998), and U.S. Pat. Nos. 5,739,386, 5,700, 642 and 5,830,655, all incorporated herein by reference). The cleavage methods may include a variety of enzymatic, or non-enzymatic means, such as chemical, thermal, photolytic cleavage, or a combination thereof. The cleavable site may be cleaved prior to, during, or after assembling two arrays. The cleavable site may be located along the polynucleotide backbone, for example, a modified 3'-5' internucleotide linkage in place of one of the phosphodiester groups, such as ribose, dialkoxysilane, phosphorothioate, and phosphoramidate internucleotide linkage. The cleavable polynucleotide analogs may also include a substituent on or replacement of one of the bases or sugars, such as 7-deazaguanosine, 5-methylcytosine, inosine, uridine, and the like. Typically, primers cleaved from the immobilized moieties are capable of hydrogen bonding in a sequence-specific manner and are capable of extending polynucleotide synthesis in amplification reactions. Preferably, the primer polynucleotides cleaved from the immobilized moieties contain a free 3'-OH end. The free 3'-OH end may also be obtained by chemical or enzymatic treatment, following the release of primer polynucleotides.

In some instances, the single stranded immobilized polynucleotides may be converted to a double-stranded immobilized polynucleotides, e.g., to load releasable primers, to incorporate double-stranded enzyme recognition site. There are many ways to prepare double-stranded polynucleotide arrays. One method is simply adding polynuleotides containing complementary sequences or subsequences with respect to the array-immobilized polynucleotides. Another method of preparation is by incorporating hairpin domain in the single-stranded polynucleotides known to those skilled in the art. Another method of preparation is simply using primers, polymerase, and dNTPs to make double stranded polynucleotide array. Another method is by hybridizing the single-stranded immobilized polynucleotide with a double-stranded polynucleotide containing a complementary single-stranded end, followed by treatment with DNA ligase, which results in double-stranded polynucleotides. This method is described in DeRisi et al., *Science* 278:680–686 (1997) and Braun et al., *Nature* 391:775–778 (1998), both incorporated herein by reference. Another method of preparing double-stranded polynucleotide arrays by synthesizing a constant sequence at every position on an array and then annealing and enzymatically extending a complementary primer is described in PCT publication WO 99/07888 and Bulyk et al. *Nature Biotechnology*, 17:573–577 (1999), both incorporated herein by reference.

In one embodiment, cleavable sites contained within the modified polynucleotide may include chemically cleavable groups, such as dialkoxysilane, 3'-(S)-phosphorothioate, 5'-(S)-phosphorothioate, 3'-(N)-phosphoramidate, 5'-(N)-phosphoramidate, and ribose. Synthesis and cleavage conditions of chemically cleavable polynucleotides are described in U.S. Pat. Nos. 5,700,642 and 5,830,655, both incorporated herein by reference. For example, depending upon the choice of cleavable site to be introduced, either a functionalized nucleoside or a modified nucleoside dimer may be first prepared, and then selectively introduced into a growing polynucleotide fragment during the course of polynucleotide synthesis. Selective cleavage of the dialkoxysilane may be effected by treatment with fluoride ion. Phosphorothioate internucleotide linkage may be selectively cleaved under mild oxidative conditions. Selective cleavage of the phosphoramidate bond may be carried out under mild acid conditions, such as 80% acetic acid. Selective cleavage of ribose may be carried out by treatment with dilute ammonium hydroxide. Preferably, the primer polynucleotides cleaved from the immobilized moieties contain a free 3'-OH end. The free 3'-OH end may also be obtained by chemical or enzymatic treatment, following the release of primer polynucleotides.

In another embodiment, cleavable sites contained within the modified polynucleotide may include nucleotides cleavable by an enzyme such as nucleases, glycosylases, among others. A wide range of polynucleotide bases may be removed by DNA glycosylases, which cleaves the N-glycosylic bond between the base and deoxyribose, thus leaving an abasic site (for a recent review, see Krokan et. al., *Biochem. J.* 325:1–16 (1997), incorporated herein by reference). The abasic site in a polynucleotide may then be cleaved by Endonuclease IV, leaving a free 3'-OH end. Suitable DNA glycosylases may include uracil-DNA glycosylases, G/T(U) mismatch DNA glycosylases, alkylbase-DNA glycosylases, 5-methylcytosine DNA glycosylases, adenine-specific mismatch-DNA glycosylases, oxidized pyrimidine-specific DNA glycosylases, oxidized purine-specific DNA glycosylases, EndoVIII, EndoIX, hydroxymethyl DNA glycosylases, formyluracil-DNA glycosylases, pyrimidine-dimer DNA glycosylases, among others. Cleavable base analogs that are readily available synthetically are preferred and modified bases that do not preventing base pairing are also preferred. In preferred embodiments, a uracil may be synthetically incorporated in a polyncletide to replace a thymine, where the uracil is the cleavage site and site-specifically removed by treatment with uracil DNA glycosylase. The uracil DNA glycosylases may be from viral or plant sources. The abasic site on the polynucleotide strand may then be cleaved by *E. coli* Endonuclease IV.

In another embodiment, the cleavable site is a restriction endonuclease cleavable site, such as class IIs restriction enzymes. For example, BpmI, BsgI, BseRI, BsmFI, and FokI recognition sequence may be incorporated in the immobilized polynucleotides and subsequently cleaved to release primer polynucleotides. In another embodiment, the cleavable site may be a nucleotide or series of nucleotides capable of blocking or terminating 5' to 3' enzyme-promoted digestion by an enzyme having 5' to 3' exonuclease activity, such as T7 Gene 6 Exonuclease, Exo VIII, Rec J, and spleen phosphodiesterase II. Blocking nucleotides include peptide nucleic acids and nucleotides containing a phosphorothioate or borano-phosphate group (U.S. Pat. Nos. 5,700,642 and 5,830,655, both incorporated herein by reference).

In preferred embodiments, the cleavable site within an immobilized polynucleotide may include a photocleavable linker, such as ortho-nitrobenzyl class of photobleavable linkers. Synthesis and cleavage conditions of certain photolabile polynucleotides on solid support are described in Rich et al., *J.C.S. Chem. Comm.* 610–611 (1973), Venkatesan et al. *J. of Org. Chem.* 61:525–529 (1996), Kahl et al., *J. of Org. Chem.* 64:507–510 (1999), Kahl et al., *J. of Org. Chem.* 63:4870–4871 (1998), Greenberg et al., *J. of Org. Chem.* 59:746–753 (1994), McMinn et al., *Tetrahedron* 52:3827–3840 (1996), Greenberg, *Tetrahedron Lett.* 34:251–254 (1993), Yoo et al., *J. of Org. Chem.* 60:3358–3364 (1995), Greenberg, *Tetrahedron* 51:29–38 (1995), McMinn et al., *J. of Org. Chem.* 62:7074–7075 (1997), Holmes et al., *J. of Org. Chem.* 60:2318–2319 (1995), Holmes et al., *J. of Org. Chem.* 62:2370–2380 (1997), and U.S. Pat. No. 5,739,386 and 5,917,016, all incorporated by reference. Certain ortho-nitrobenzyl-based linkers may also be obtained commercially. For example, hydroxymethyl, hydroxyethyl, and Fmoc-aminoethyl carboxylic acid linkers are available from Novabiochem (http://www.nova.ch). The DMT-protected o-nitrobenzyl on a solid support may also be obtained commercially (e.g., from Glen Research). For coupling photolabile linkers to hydrophilic/hydrophobic arrays, reaction of the photolabile linker with a primary amine on the array surface may be achieved using standard peptide coupling reagents.

In general, a surface immobilized photocleavable linker may have the formula of S-B-L where S is a solid support, B is a bond or a derivatizing group, and L is a photocleavable linking group having the formula:

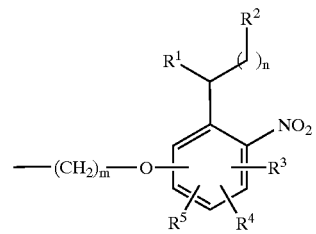

where, $R_1$ is hydrogen, $C_1$–$C_8$ alkyl, aryl or arylalkyl; $R_3$, $R_4$ and $R_5$ are each independently hydrogen, $C_1$–$C_8$ alkyl, or $C_1$–$C_8$ alkoxy; $R_2$ is halogen, —SH, —SP, —OH, —NH$_2$, —OP or —NHP, wherein P is a suitable protecting or activating group; and n is 0 or 1 and m is an integer of from 1 to 10. This class of photocleavable linkers may be coupled to the synthesis of a variety of biopolymers such as polynucleotides and polypeptides.

In some embodiments of the invention, nonphotolabile analogue of the photolabile group, such as veratryl alcohol, may be doped in the synthesis of photocleavable immobilized polynucleotide, thus creating a heterogeneous mixture of photocleavable and nonphotocleavable immobilized polynucleotides at a finite area on the surface of an array. By varying the ratio of the amount of cleavable and noncleavable linker, the relative molar quantities of the cleaved and surface bound polynucleotides may be optimized for capturing the amplification products of amplification reactions, and for polynucleotide elongation of the complexes between the surface bound noncleavable polynucleotides and the captured amplification products.

For immobilized polypeptide in solid phase synthesis, simultaneous deprotection of the side-chain groups and the cleavage of peptide from the solid support may be achieved by treatment with a hard acid, such as hydrogen fluoride (HF), trifluoromethanesulfonic acid (TFMSA), or trifluoromethanesulfonic acidtrimethylsilyl ester (TMSOTf) (Steward, *Methods in Enzymol.* 289:29–44 (1997), incorporated herein by referece). In addition to production of free polypeptides by acidolysis, a peptide amide may be produced by treatment with ammonia and amines. Polypeptide may also be reduced to alcohols by treating with $LiBH_4$ in THF. Sequence specific cleavage of polypeptides or modifications thereof may be carried out using suitable enzymes, such as proteases, known in the art. In addition, phenacyl based or ortho-nitrobenzyl based linking group may also be used as a photocleavable linker to couple peptides to solid support (Wang, *J. Org. Chem.* 41–3258 (1976), Rich et al., *J. Am. Chem. Soc.* 97:1575–1579 (1975), Hammer et al., *Int. J. Peptide Protein Res.* 36:31–45 (1990), U.S. Pat. Nos. 5,739,386 and 5,917,016). Photolysis offers a mild method of cleavage which complements traditional acidic or basic cleavage techniques (see, e.g., Lloyd-Williams et al., *Tetrahedron* 49:11065–11133 (1993)). Photocleavage of peptide ligands from solid supports for screening enzyme inhibitors has also been reported (Schullek et al., *Anal. Biochem.* 246:20–29 (1997)).

For immobilized polysaccharides, linker groups typically have enough stability to withstand glycosylation reaction conditions, while being able to undergo cleavage in mild conditions without affecting the polysaccharide backbone structure and protecting groups. Photolabile linkers, described in Nicolaou et al., supra and Rodebaugh et al., supra, may be used. A silyl ether may be removed by a fluoride ion (Danishefsky, et al., supra) and a thioglycoside-like linker may be cleaved under various thiophilic conditions (Yan et al., supra). In addition, base-labile linkers, such as 9-fluoroenylmethoxycarbonyl-type and succinate type may be cleavable with triethylamine and aqueous ammonia, respectively (Adinolfi et al., *Tetrahedron Lett.* 37:5007–5010 (1996) and Wang et al., *Chem. Lett.* 273–274 (1995), both incorporated herein by reference).

III. Carrying Out Large Numbers of Reactions Using Array Assembly

One of skill in the art will appreciate that all non-unimolecular reactions, which require two or more reactants are compatible with the present method and apparatus. In preferred embodiments of the instant invention, a myriad of chemical and biological reactions may be carried out using the instant method and apparatus. These reactions may involve cells, viruses, nucleic acids, proteins, carbohydrates, lipids, or small molecules. These reactions may be polynucleotide amplification reactions, or molecular binding interactions, such as, protein-DNA, nucleic acid hybridization, inhibitor-enzyme, receptor-antagonist, drug-DNA, antibody-antigen, toxin-carbohydrate, receptor-glycoprotein binding reactions, among others.

A. Polynucleotide amplification reactions

A large variety of polynucleotide amplification reactions known to those skilled in the art may be suitable for the instant invention. The most common form of polynucleotide amplification reaction, such as a PCR reaction, is typically carried out by placing a mixture of target nucleic acid sequence, deoxynucleotide triphosphates, buffer, two primers, and DNA polymerase in a thermocycler which cycles between temperatures for denaturation, annealing, and extension (*PCR Technology: Principles and Applications for DNA Amplification* (ed. H. A. Erlich, Freeman Press, NY, N.Y., 1992), *PCR Protocols: A Guide to Methods and Applications* (eds. Innis, et al., Academic Press, San Diego, Calif., 1990), Mattila et al., *Nucleic Acids Res.* 19:4967 (1991), Eckert et al., *PCR Methods and Applications* 1, 17 (1991), *PCR A Practical Approach and PCR2 A Practional Approach* (eds. McPherson et al., Oxford University Press, Oxford, 1991 and 1995), all incorporated by reference). The selection of primers defines the region to be amplified. The polymerase used to direct the nucleotide synthesis may include, for example, *E. coli* DNA polymerase I, Klenow fragment of *E. coli* DNA polymerase, polymerase muteins, heat-stable enzymes, such as Taq polymerase, Vent polymerase, and the like. For a reverse-transcriptase-PCR, enzyme such as reverse transcriptase may be used.

With the aid of arrays, large numbers of PCR reactions may be performed in parallel by confining selected PCR reactants to definite areas on two arrays, bringing two arrays into apposition, and allowing reactants on two arrays to merge and triggering PCR reactions. In preferred embodiments of the instant invention, One or more primers of the PCR reaction may also be first hybridized to immobilized moieties on defined areas of a first array surface and subsequently released by strand separation. One or more primers of the PCR reaction may be first immobilized on defined areas of an array surface via a cleavable site and subsequently released upon array assembly. The covalent array immobilization site may either be at the 5' end of the polynucleotide (or the 3' distal and 5' proximal orientation) or at the 3' end of the primer polynucleotide (or the 3' proximal and 5' distal orientation). In some instances, the array immobilization site may be within the polynucleotide (i.e. at a site other than the 5' or 3' end of the polynucleotide). The array-immobilized and primer-containing moieties typically have lengths ranging from about 5 to 100 nucleotides, preferably between about 10 to 50 nucleotides, more preferably between about 10 to 30 nucleotides.

The remaining reactants of the PCR reaction may be confined to defined areas or reaction wells on the surface of another array. The combination of two groups of reactants is achieved by bringing two arrays into close proximity and allowing the merge of reactants on two arrays. The primers of the PCR reaction may be released chemically, enzymatically, or photolytically before, during, or after assembling two arrays.

Following the primer release, the PCR reactions may be performed according to known protocols in the art. Typically, the temperature may be raised to separate the double-stranded target nucleic acid to form the single-stranded templates for amplification. The temperature may then be lowered to generate the primed templates for DNA polymerase. The temperature may again be raised to promote polynucleotide synthesis, and the cycle of strand separation, annealing of primers, and synthesis is repeated for about as many as 30–60 cycles.

One of skill in the art will appreciate that many other polynucleotide amplification reactions may also be carried out using the instant method and apparatus. For reviews, see Isaksson and Landegren, *Curr. Opin. Biotechnol.* 10:11 –15 (1999), Landegren, *Curr. Opin. Biotechnol.* 7:95–97 (1996), and Abramson et al., *Curr. Opin. Biotechnol.* 4:41–47 (1993), all incorporated herein by reference. Typically, amplification of either or both strand of the target nucleic acid comprises the use of one or more nucleic acid-modifying enzymes, such as a DNA polymerase, a ligase, an RNA polymerase, or an RNA-dependent reverse transcriptase. For example, polynucleotide amplification reactions may include self-sustained sequence replication (3SR) (Muller et al., *Histochem. Cell Biol.* 108:431–437 (1997), incorporated herein by reference), nucleic acid sequence-based amplification (NASBA) (Malek et al., *Methods Mol. Biol.* 28:253–260 (1994), incorporated herein by reference), strand displacement activation (SDA) (Walker, *PCR Methods Appl.* 3:1–6 (1993), incorporated herein by reference), ligase chain reaction (LCR) (Wu et al., *Genomics* 4:560 (1989), Landegren et al., *Science* 241:1077 (1988), Abravaya et al., *Nucleic Acids Res.* 23:675–682 (1995), and Wiedmann et al., *PCR Methods Appl.* 3:S51–64 (1994), all incorporated herein by reference), and Qβ replicase system (Burg et al., *Anal. Biochem.* 230:263–272 (1995), incorporated herein by reference), among others. Depending on the target nucleic acid and its concentration, polynucleotide amplification reactions may either exhibit solution or solid phase reaction profile.

B. Coupling of polynucleotide amplification reactions and sequence variation detections The present invention may be used to couple the amplification and detection procedures, thus providing an environment for simultaneously carrying out thousands of amplification reactions followed by simultaneous detection of thousands of amplified products on the array assembly. This coupling of amplification reactions and sequencing reactions simplifies the detection procedure and streamlines the methods of amplification and sequencing. Array assembly is a faster and cost-effective method for amplification and sequencing, which is amendable to high throughput applications.

In some embodiments of the instant invention, the amplification products generated in polynucleotide amplification reactions may be captured by immobilized polynucleotide interrogation probes or non-cleavable moieties on either the first or the second array. The capture may be accomplished by hybridizing amplification products with immobilized interrogation probes. For example, a fraction of immobilized polynucleotides may contain non-cleavable polynucleotides designed for capturing amplification products, while another fraction of immobilized polynucleotides confined in the same area of the array may contain cleavable polynucleotides designed for delivering amplification primers during the assembly of two arrays. It is also possible to immobilize non-cleavable moiety at a different area than the primer-containing cleavable immobilized moiety for capturing amplified products. Therefore, when amplification reactions are completed between two arrays and the arrays are pulled apart, each strand of the amplified products may be separated as each strand forms different hybridization complexes between non-cleavable polynucleotides remain immobilized on an array. It is also possible to carry out amplifications that result in an excess of one strand of the amplification products by varying primer concentrations. In this case, single stranded amplification products may also be captured by non-cleavable polynucleotides immobilized on an array.

After the amplified products of a target nucleic acid are captured, they may be directly or indirectly used in detecting polynucleotide sequence variations. Strategies for identification and detection of polynucleotide sequence variations are known in the art (Nelson, *Crit. Rev. Clin. Lab. Sci.* 35:369–414 (1998), Landegren et al., *Genome Res.* 8:769–776 (1998), Syvänen, *Human Mutation* 13:1–10 (1999), U.S. Pat. Nos. 6,001,567, 5,985,557, 5,888,819, 5,650,277, 5,710,028, 5,858,659, and 5,871,928, and PCT applications WO 99/27137, 98/54362, 98/56954, 98/38846, 99/14228, 98/30883, and 99/37812, all incorporated herein by reference).

In general, the identification of a sequence variation may be separated into two categories. In one category, the sequence variants may be distinguished by hybridization. This method employs immobilized sequence-specific polynucleotide probes. A single mismatch in a hybridization complex formed between amplification product and probes may cause a significant change in the signals detected. In a typical approach, a series of probes of known sequence and of similar length, each with one of the four different bases at a given location near the center position are affixed to the array surface.

In the second category, the sequence variants may be determined using polynucleotide modifying enzymes. The polynucleotide modifying enzymes include DNA polymerases, DNA ligase, nuclease, and restriction enzymes, among others. For example, in a minisequencing reaction, a DNA polymerase is used to extend an interrogation primer that anneals immediately adjacent to the nucleotide position of interest with a single labeled nucleoside triphosphate complementary to the nucleotide at the variant site.

1. Sequence variation detection by hybridization In one aspect, the present invention is suitable for determining precharacterized polynucleotide sequence variations. In other words, the genotyping is performed after the location and nature of polymorphic forms or mutations have already been determined. The sequences of known polymorphic forms and the wild-type/mutation sequences may be used to as reference sequences. For example, the two polymorphic forms of a biallelic single nucleotide polymorphism (SNP) may be used as two reference sequences. To analyze a deletion mutation, one can select the wild-type form and the deleted form as two reference sequences. In some instances, sequence variations of both the coding and noncoding strands of the target nucleic acid sequence may be determined. Therefore, both the coding and noncoding strands may be used as reference sequences for sequence variation determinations.

Although, in general, the reference sequences are from the same source as the target nucleic acid, in some instances, they may be from difference sources. For example, the sequences can be from a human or mouse. A substantial number of mutations and polymorphic forms have been reported in the published literature or may be accessible through publicly available web sites. See also, Gelfand et al., *Nucleic Acids Res.* 27:301–302 (1999) and Buetow et al., *Nat. Genet.* 21:323–325 (1999). The availability of reference sequence information allows an initial set of polynucleotide probes to be designed for the identification of the know sequence variations.

The determination of sequence variations using the present invention also includes de novo characterizing polynucleotide sequence variations. In other words, genotyping may be used to identify points of new variations and the nature of new variations. For example, by analyzing a group of individuals representing ethnic diversity among humans, the consensus or alternative alleles/haplotypes of the locus may be identified, and the frequencies in the population may be determined. Allelic variations and frequencies may also be determined for populations characterized by criteria such as geography, gender, among others. Such analysis may also be performed among different species in plants, animals, and other organisms.

A set of polynucleotide probes based on reference sequences for each sequence variation may be designed. The design of a probe set typically includes probes that are perfectly complementary to the reference sequences and span the location of each sequence variation. Perfect complementary means sequence-specific base pairing which includes e.g., Waston-Crick base pairing or other forms of base pairing such as Hoogstein base pairing. Leading or trailing sequences flanking the segment of complementarity can also be present. In the simplest form, a pair of polynucleotide probes perfectly complementary to the two polymorphic forms of a biallelic SNP (two reference sequences) may be employed. Of course, additional related polynucleotide probes may be added to improve the accuracy of the detection. For example, for each perfectly complementary probe, there may be three corresponding probes, each with a different nucleotide at the variation position. More complex design of polynucleotide probes known to those skilled in the art may also be employed. For example, various tiling methods (e.g., sequence tiling, block tiling, 4×3 tiling, and opt-tiling) are described in WO 95/11995, WO 98/30883, WO 98/56954, EP 717113A2, and WO/99/39004, all incorporated herein by reference.

Figure 4A:
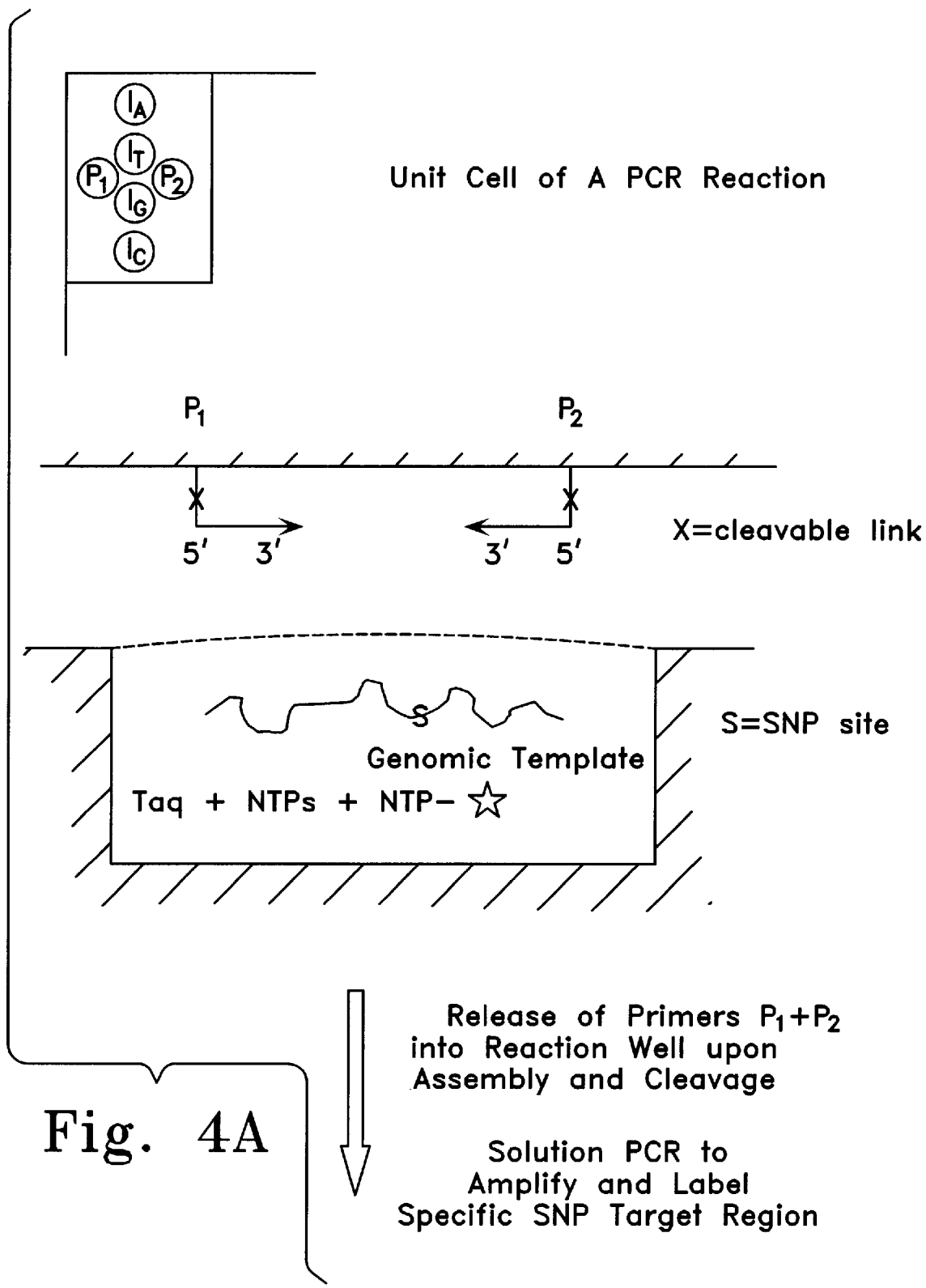
FIGS. 4A–4C illustrate a method of amplifying a target nucleic acid, capturing the amplified products and sequencing by hybridization with captured amplified products.
Figure 4B:
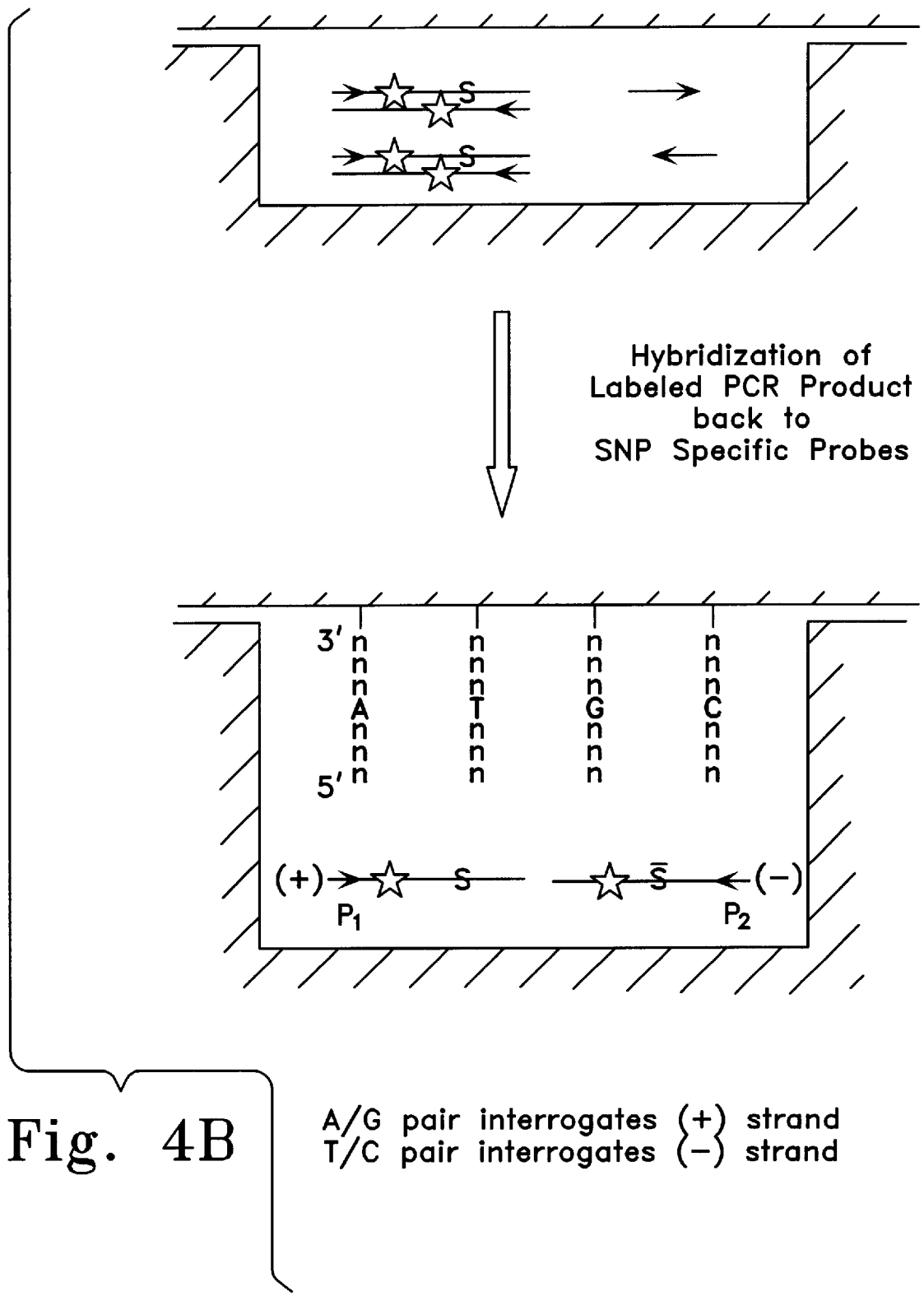
Figure 4C:
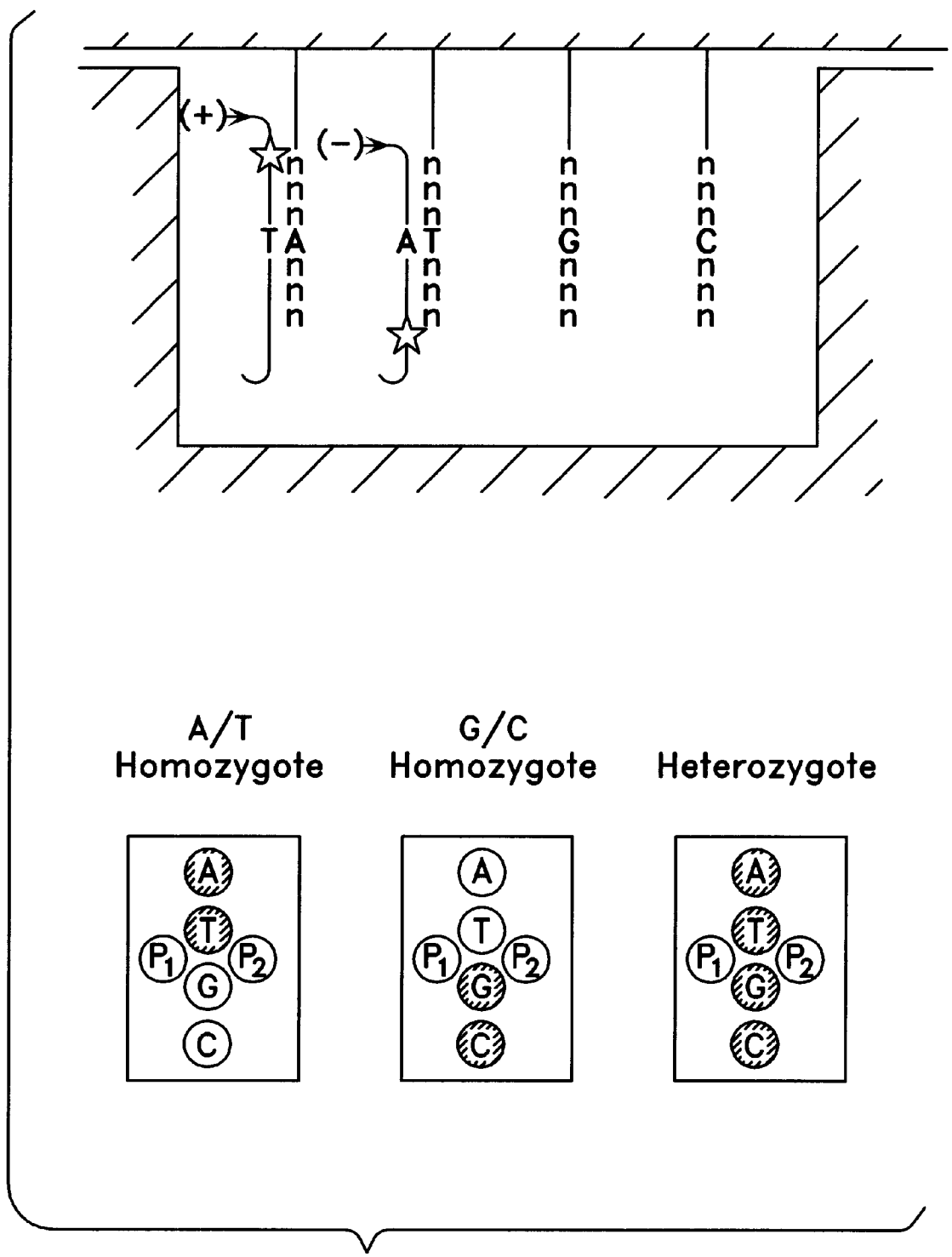
Figure 5A:
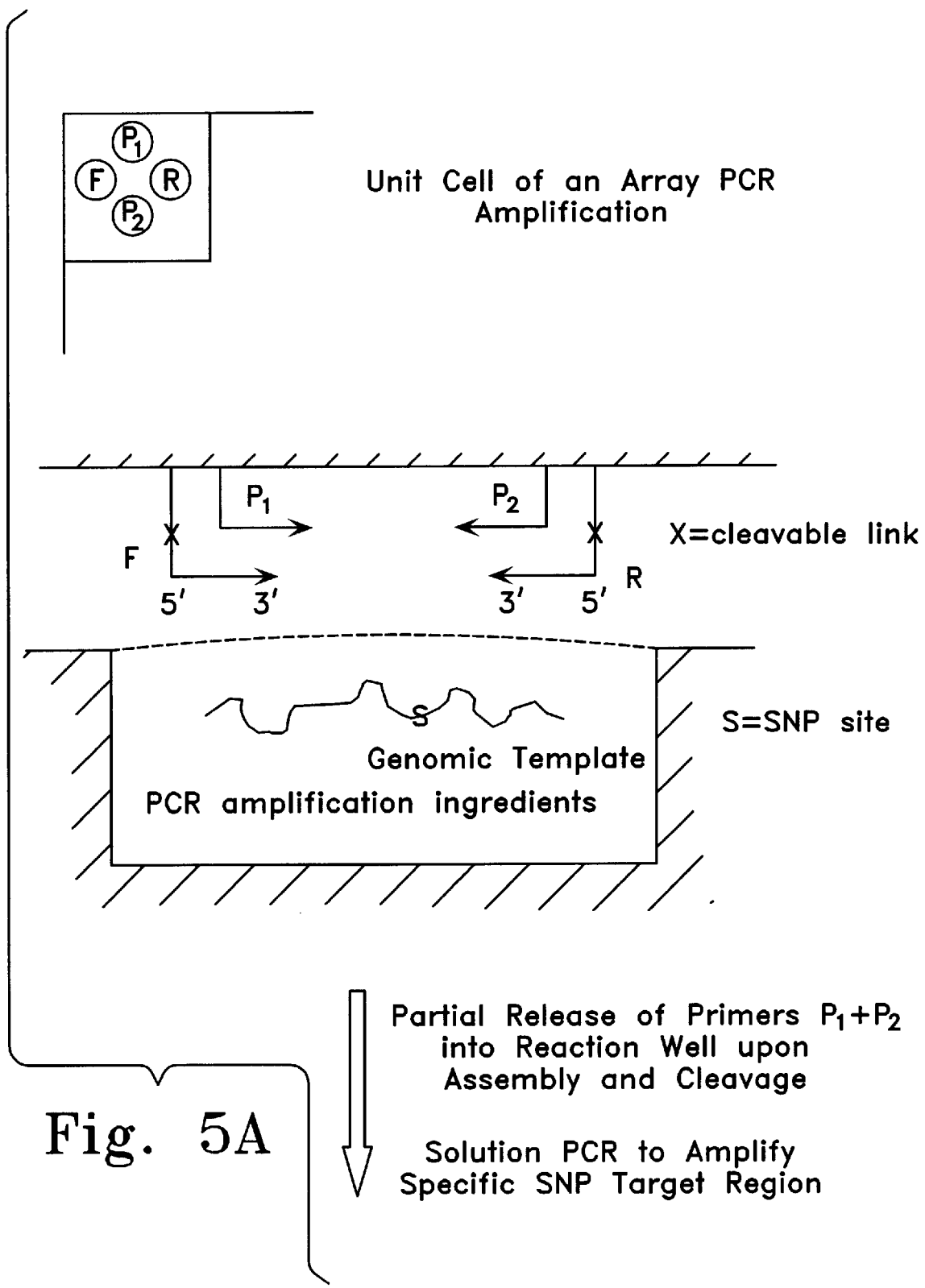
FIGS. 5A–5D illustrate a method of amplifying a target nucleic acid, capturing the amplified products, and sequencing by primer extension reactions using captured amplified products.
Figure 5B:
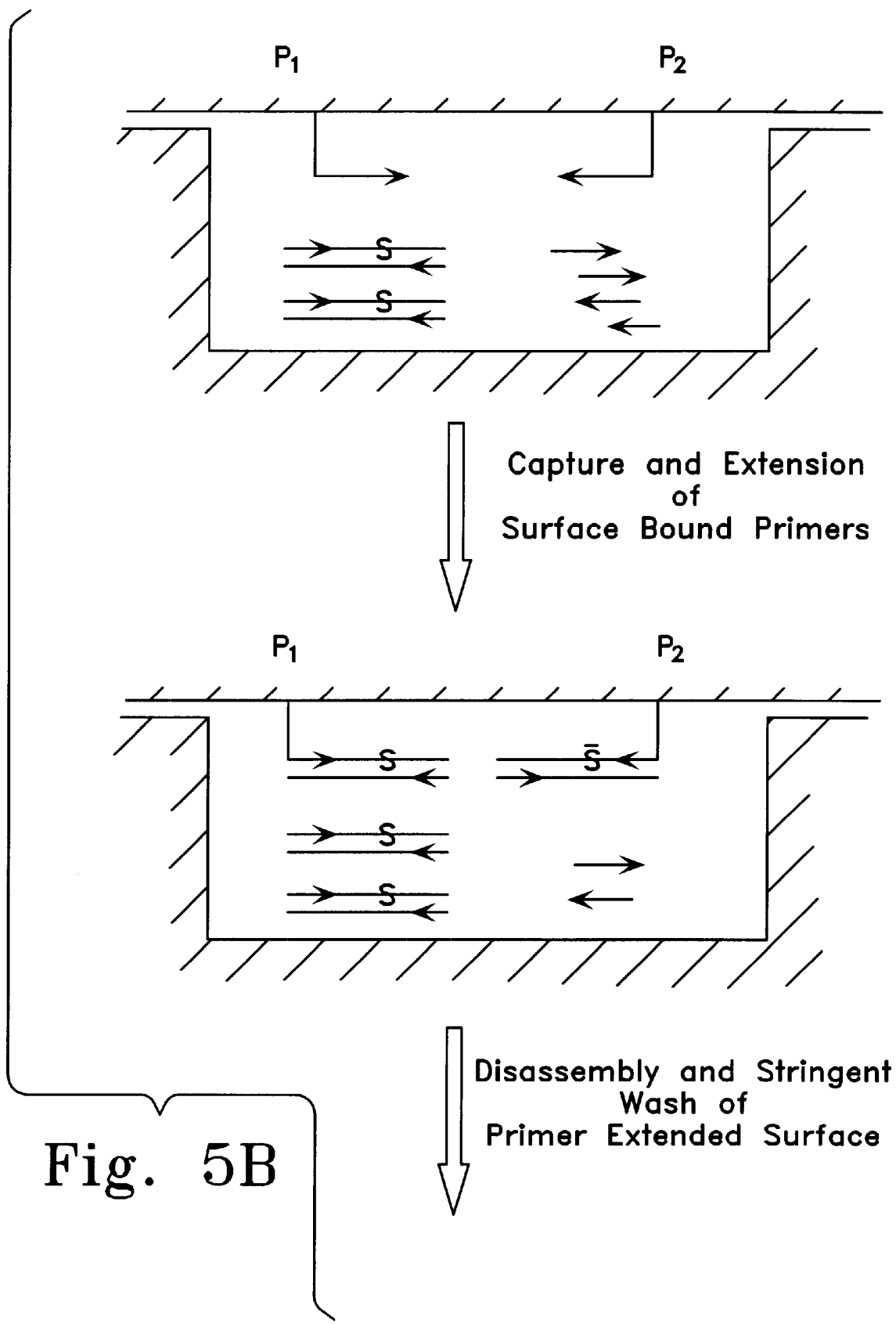
Figure 5C:
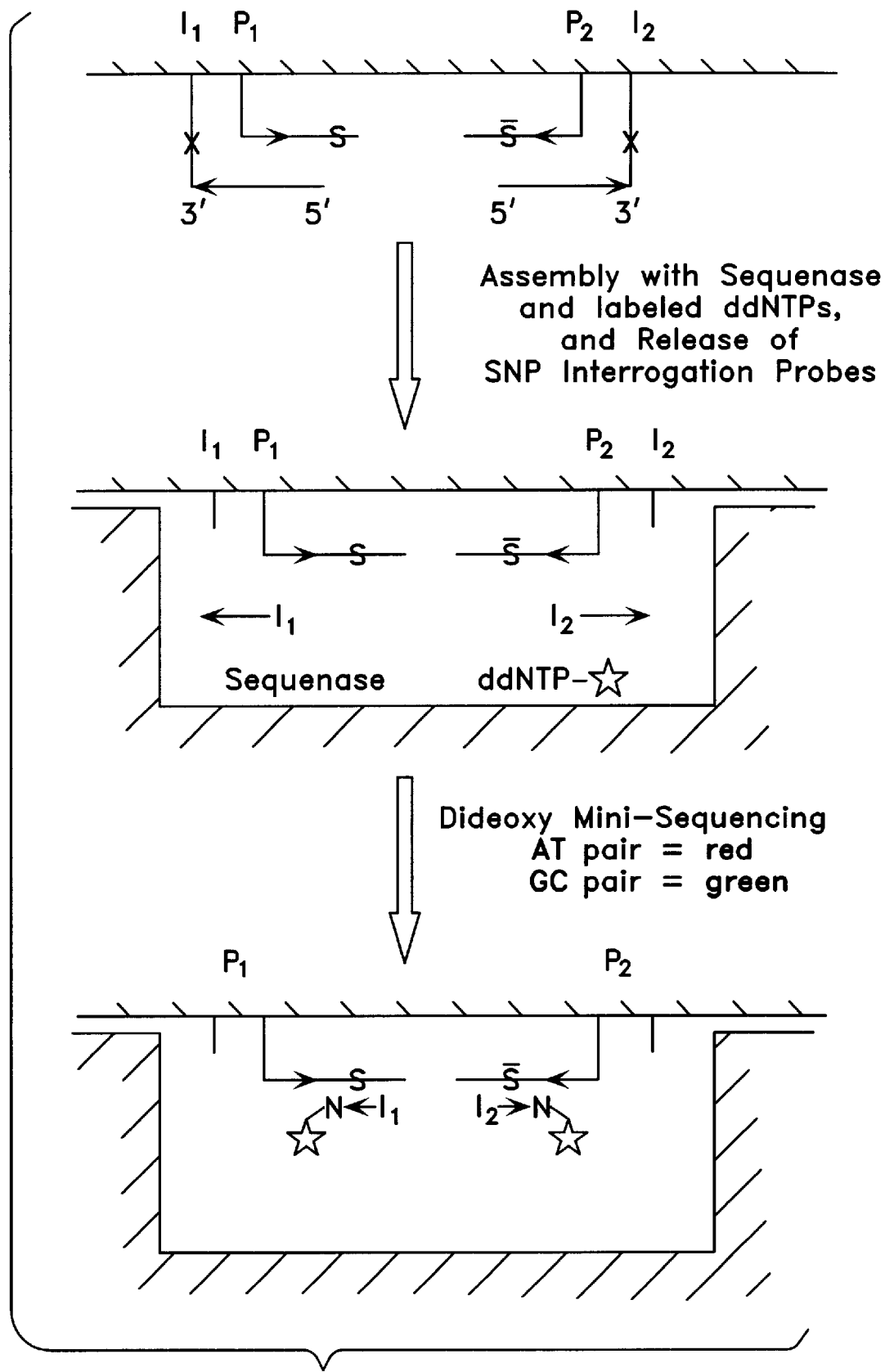
Figure 5D:
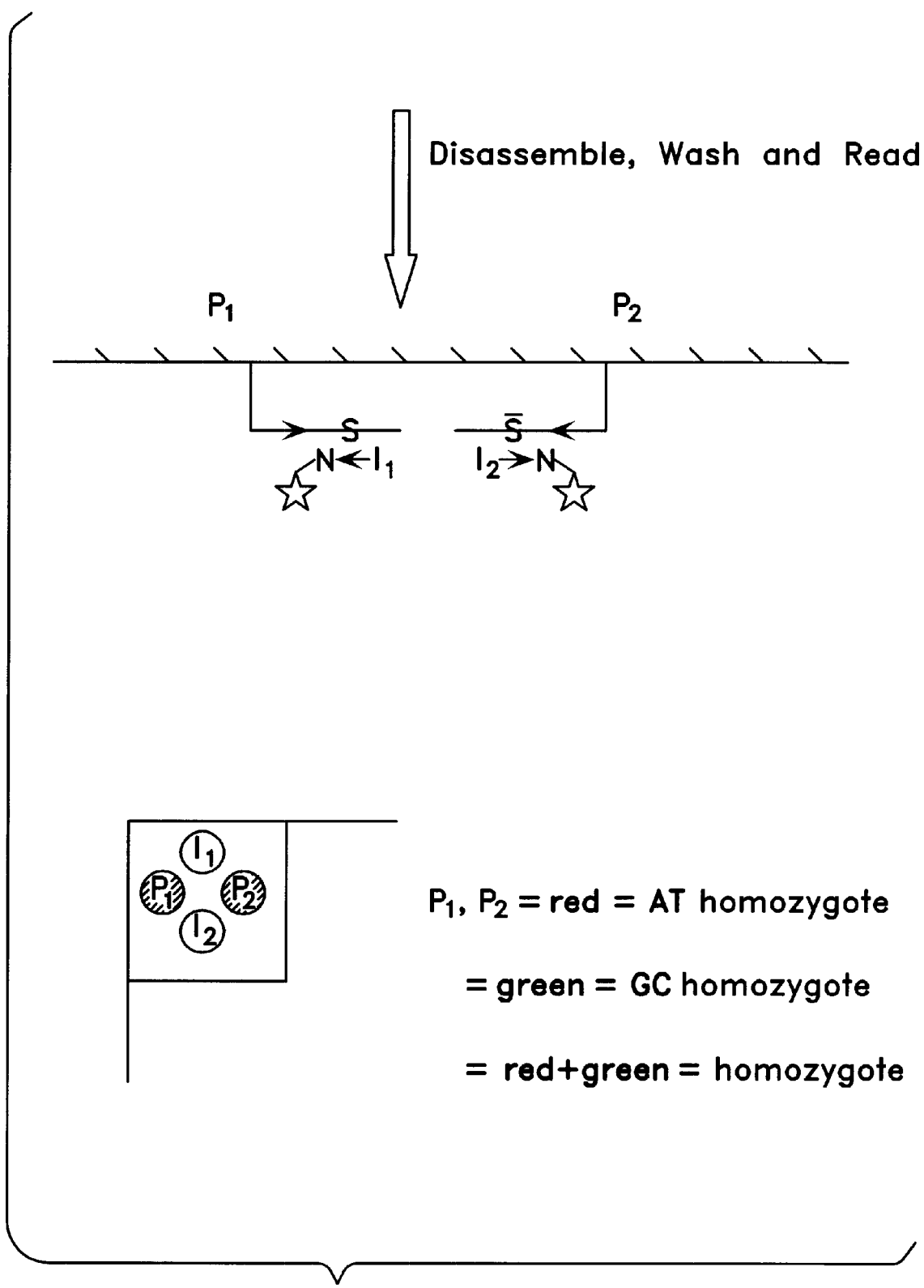
Figure 6A:
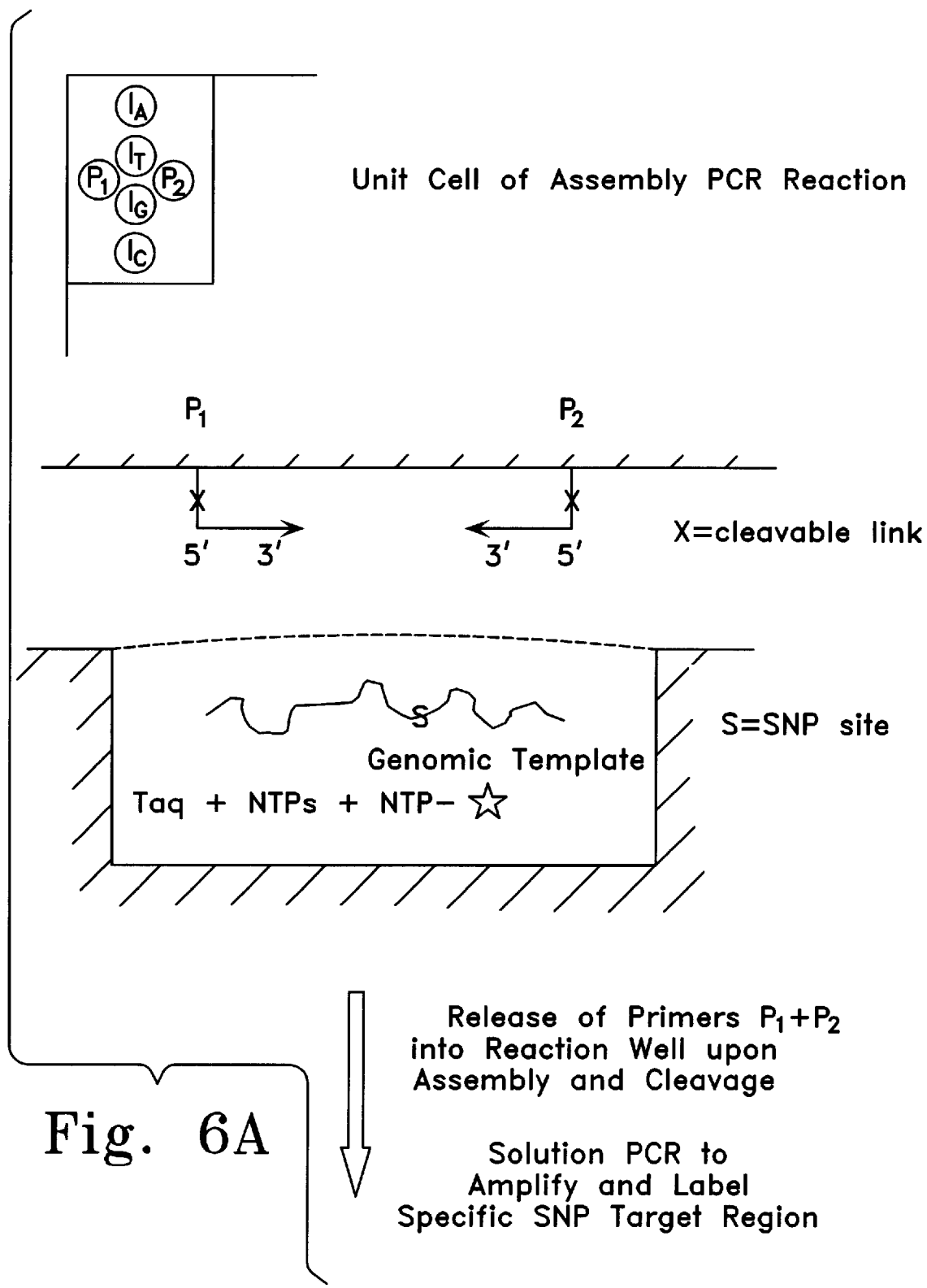
FIGS. 6A–6D illustrates a method of amplifying a target nucleic acid, capturing the amplified products, and sequencing by primer extension, in the absence of chain terminating nucleotides, using captured amplified products.
Figure 6B:
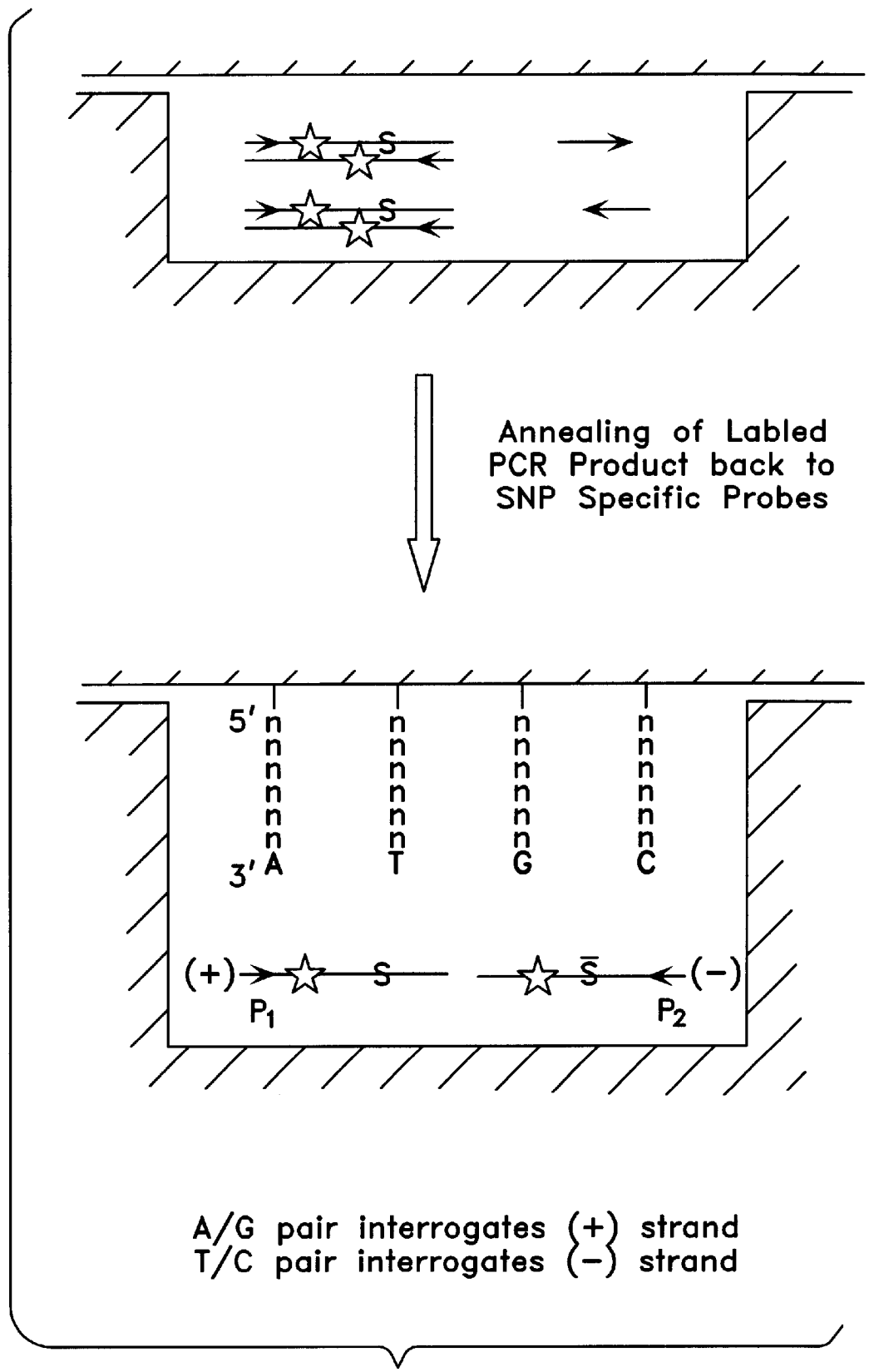
Figure 6C:
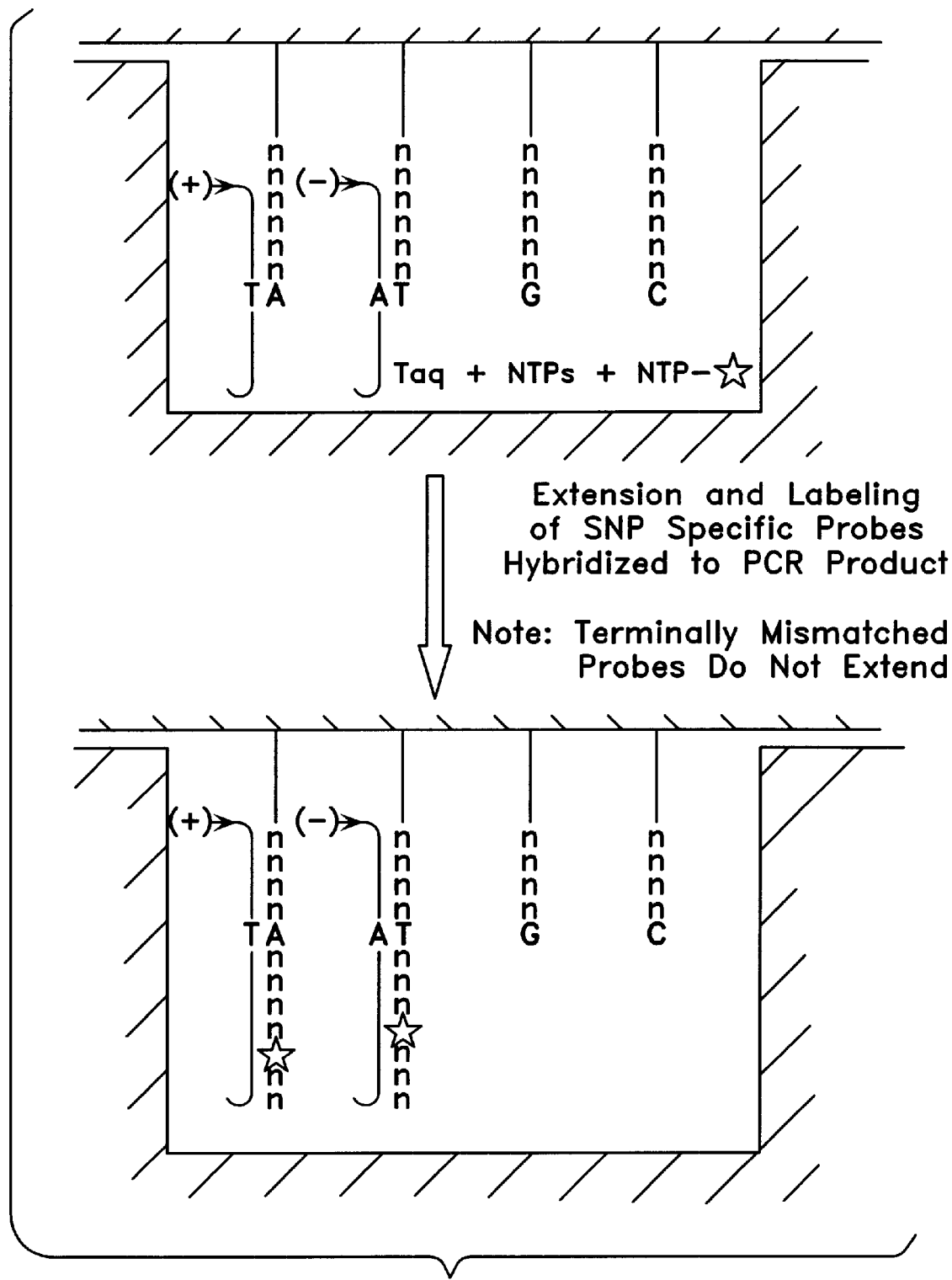
Figure 6D:
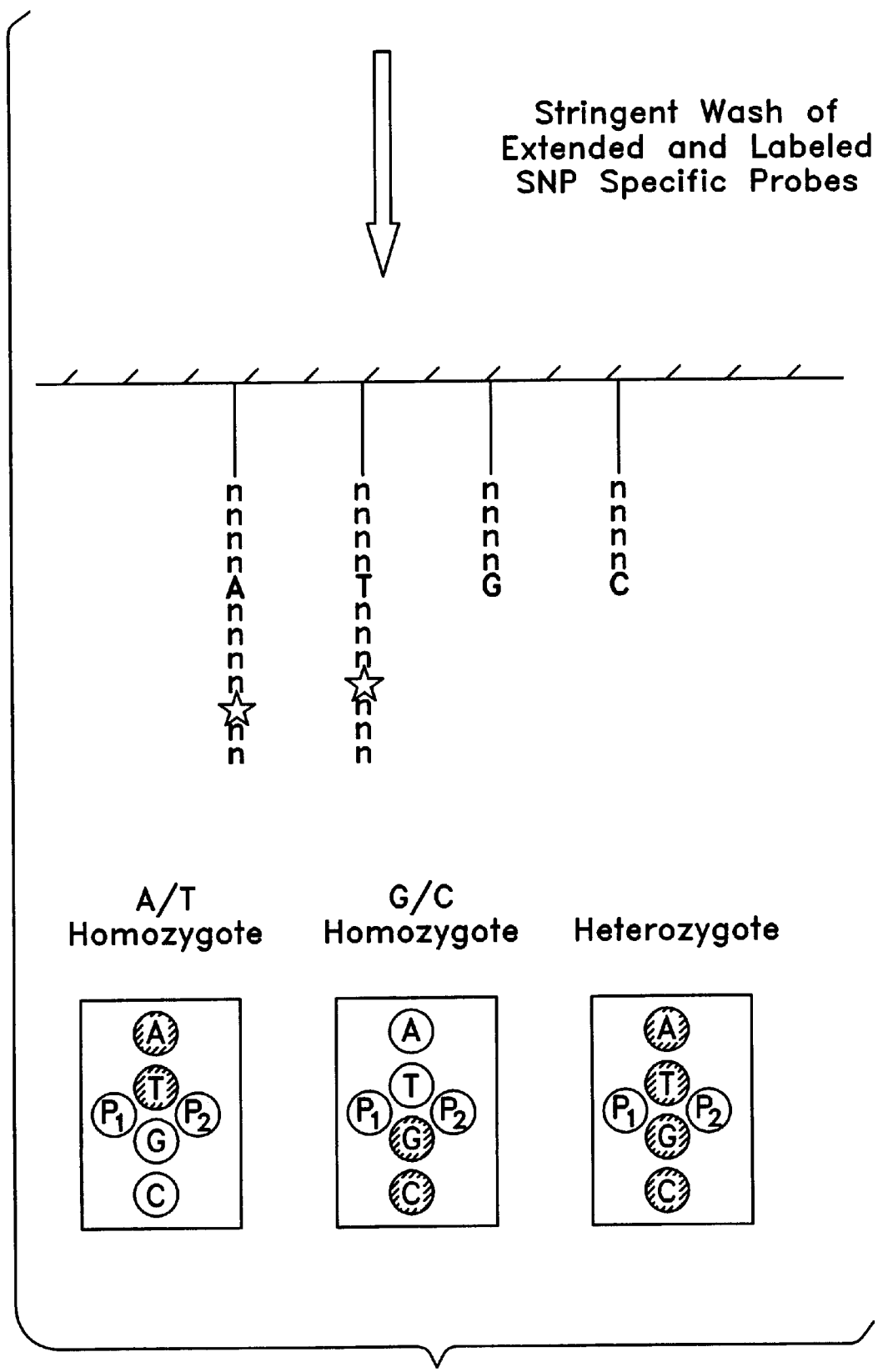

A diploid organism may be homozygous or heterozygous for a biallelic SNP. There are four possible SNP homozygotes (A/A, T/T, C/C, and G/G) and six possible heterozygotes (T/A, A/G, C/T, C/A, T/G, and C/G). When the polynucleotide probes are hybridized with a heterozygous sample in which both polymorphic forms are present, the patterns for the homozygous polymorphic forms are superimposed. Thus, the probes show distinct and characteristic hybridization patterns depending on which sequence variation is present and whether an individual is homozygous or heterozygous. FIG. 4 is an example of amplifying a target nucleic acid, capturing the amplified products and sequencing by hybridization with captured amplified products.

In addition to using array-immobilized polynucleoitdes for hybridization detection, many homogeneous hybridization detection methods may also be employed. For example, hybridization probe that form hairpin-loop structure in the absence of the correct target nucleic acid may be utilized (Tyagi et al., *Nature Biotechnol.* 16–49–53 (1998)). The formation of a hairpin-loop conformation brings the fluorophore and the quencher pair close together, thus extinguishing the donor fluorescence.

2. Sequence variation detection by a polynucleotide modifying enzyme

In some embodiments of the instant invention, the captured amplification products may be used indirectly in the subsequent sequencing reactions. For example, hybridization complexes between the captured amplification products and immobilized polynucleotides may be further extended using a suitable DNA modifying enzyme to determine the sequence of the amplified products.

In the primer extension method, nucleotide extension reaction catalyzed by the DNA polymerase is used to distinguish between the sequence variants. For example, a sequencing probe may be annealed to the amplified polynucleotides, e.g. immediately 3' of the sequence variation position. This primer may then be extended with one or more labeled nucleoside triphosphates that are complementary to the nucleotide to be detected using a DNA polymerase. The distinction between the sequence variants is based on the accuracy of the nucleotide incorporation reaction catalyzed by a DNA polymerase, not the differences in thermal stability between mismatched and perfectly matched hybridization complexes. This method allows discrimination between the homozygous and heterozygous genotypes. This method is robust and insensitive to small variations in the reaction conditions. The same reactions may be employed for detecting any nucleotide variable nucleotide irrespective of the nucleotide sequence flanking the variable site.

Typically, any DNA polymerase without proofreading activity may be used in this method in order to avoid 3'–5' degradation of the probe. DNA polymerase may include Klenow DNA polymerase, T7 DNA polymerase ("Sequenase"), thermostable polymerase, among others. Depending upon the polymerase, different conditions may be used, and different temperature ranges may be required be the hybridization and extension reactions. Any labeled nucleotide analogue that is incorporated sequence specifically by a DNA polymerase may serve as detectable group. In one embodiment, labeled extension terminators, such as dideoxoynucleotides (e.g., ddATP, ddCTP, ddGTP, ddTTP, and ddUTP), arabinoside triphosphates, may be used because they terminate the extension reaction. Therefore, enzymatic extension of the sequencing primer by one nucleotide depends on the correct base pairing of the added nucleotide to the nucleotide variation to be detected. In another embodiment, labeled deoxynucleotides may be used to extend the primer beyond one nucleotide. Therefore, enzymatic extension of the sequencing primer by more than one nucleotide depends on the correct base pairing of the sequencing primer to the nucleotide variation to be detected.

To obtain specific extension of the polynucleotide in the sequencing step, the excess of amplification reagents are removed before the sequencing reaction. A second separation step may also be used to separate the labeled extension products from the unincorporated labeled nucleotide before measurement. In addition, any size fractionating methods may be used to determine the sequence of primer extension products. These methods include gel electrophoresis, such as polyacrylamide or agarose gel electrophoresis, capillary electrophoresis, mass spectrometry, and HPLC.

In another example, the 5' nuclease activity of a variety of enzymes may also be employed to cleave and detect target-dependent cleavage structure (also known as the Invader® assay). Specific DNA and RNA sequences are detected by using structure-dependent enzymes to cleave a hybridization complex with overlapping polynucleotide probes. Details of detecting sequence variations using 5' nuclease assay have been described in WO 98/4287. Details of detecting sequence variations using structure-bridging polynucleotides have been described in WO 98/50403.

In addition, the sequence variants may be determined by using mass spectrometry, such as matrix-assisted laser desorption/ionisation time-of-flight mass spectrometry, tandem mass spectrometry, etc. Certain examples of sequence variation detection using mass spectrometry have been described in U.S. Pat. Nos. 6,074,823, 6,043,031 and 5,691,141. Sequence variations may be distinguished by marker, hybridization pattern, or discrimination of DNA modifying enzyme (e.g., exonuclease) followed by mass spectrometry.

FIG. 5 is an example of amplifying a target nucleic acid, capturing the amplified products, and sequencing by primer extension reactions using captured amplified products. FIG. 6 is an example of amplifying a target nucleic acid, capturing the amplified products, and sequencing by primer extension, in the absence of chain terminating nucleotides, using captured amplified products.

B. Coupling of polynucleotide amplification reactions and quantitations of polynucleotides The multiplexing method and apparatus disclosed in the instant invention may be used to quantitate nucleic acid molecules, for example measuring gene expression, gene copy number, viral load, etc.

One application is the monitoring of gene expression level and comparing of gene expression patterns following PCR amplification of target nucleic acid. Many gene-specific polynucleotide probes derived from the 3' end of RNA transcripts may be spotted on a solid support. This array is then probed with fluorescently labeled cDNA representations of RNA pools from test and reference cells. The relative amount of transcript present in the pool is determined by the fluorescent signals generated and the level of gene expression is compared between the test and the reference cell. See, e.g., Lockhart et al., *Nature* 405:827–836 (2000), Roberts et al., *Science* 287:873–880 (2000), Hughes et al., *Nature Genetics* 25:333–337 (2000), Hughes et al., *Cell* 102:109–126 (2000), Duggan, D., et al., *Nature Genetics Supplement* 21:10–14 (1999), DeRisi, J., et al., *Science* 278:680–686 (1997), and U.S. Pat. Nos. 5,800,992, 5,871,928, and 6,040,138, all incorporated herein by reference.

In the instant invention, gene expression monitoring or profiling may be performed on a solid support with in situ synthesized polynucleotides. The simultaneous monitoring of the expression levels of a multiplicity of genes permits comparison of relative expression levels and identification of biological conditions (e.g., disease detection, drug screening) characterized by alterations of relative expression levels of various genes. The simultaneous monitoring of the expression levels also includes the determination of the presence or absence of genes.

Polynucleotide probes for expression monitoring may include probes each having a sequence that is complementary to a subsequence of one of the genes (or the mnRNA or the corresponding antisense cRNA). The gene intron/exon structure and the relatedness of each probe to other expressed sequences may also be considered. Polynucleotide probe set may additionally include mismatch controls, normalization probes, and expression level control probes, among others. In particular, expression level control probes are those hybridize specifically with constituively expressed genes in the biological sample, such as β-actin, the transferrin receptor gene, the GAPDH gene, and the like. They are designed to control for the overall health and metabolic activity of a biological sample.

In some embodiments, a multiplicity of genes may be monitored in real time by using reverse transcriptase PCR. Quantitation of transcription levels of multiple genes can be absolute or relative. Absolute quantification may be accomplished by inclusion of known concentration of one or more target nucleic acids such as control nucleic acids or known amounts of the target nucleic acids to be detected. The relative quantification may be accomplished by comparison of hybridization signals between two or more genes, or between two or more treatments to quantify the changes in hybridization intensity.

In addition of quantitating polynucleotides based on hybridization, a polynucleotide modifying enzyme may also employed to quantitatively measure polynucleotides (see, e.g., Lie et al., *Curr. Opin. in Biotech.* 9:43–48 (1998), incorporated herein by reference). These methods include for example quantitative PCR, competitive PCR, and 5' nuclease assay.

In a 5' nuclease assay (also known as the TaqMan™ technology), a polynucleotide probe is annealed to a target sequence located between the forward (5') and reverse (3') primer binding sites. The probe may be labelled with a reporter dye (e.g. FAM, 6-carboxyfluorescein) at the 5' end and a quencher dye (e.g. TAMRA, 6-carboxytetramethylrhodamine) in the middle, or at the 3' end, which compensates the emission spectra of the reporter dye as long as both dyes are attached to the probe. Modification of the probe with a 3'-blocking phosphate may prevent extension of the annealed probe during amplification. Cleavage of the probe by 5'–3' exonuclease activity of a thermostable polymerase (e.g., a Taq polymerase) during strand elongation releases the reporter from the probe and thus its proximity to the 3' quencher, resulting in an increase in reporter emission intensity. Thus, the fluorescence signals are detectable and can be quantified. The cycle at which the emission intensity of the sample rises above baseline (threshold cycle) is inversely proportional to the target sequence concentration. The higher the target concentration, the lower the number of amplification cycles required to detect the rise in reporter emission above baseline. Typically, an ABI PRISM™ Sequence Detection System (PE Applied Biosystems) may be used to detect the fluorescent signals. Two probes labelled with different reporter dyes (e.g., FAM, tetrachloro-6-carboxy-fluorescein [TET], hexachloro-6-carboxyfluorescein [JOE]) may also be used in the 5' nuclease assay. This two-color detection may improve sample quantitation accuracy, reduce assay sample numbers and increase sample throughput.

The 5' nuclease assay may be improved by measuring the released fluorescent emission continuously during the PCR amplification instead of an endpoint measurement (Real Time PCR quantification, Heid et al., *Genome Res.* 6:986–994 (1996); Gibson et al. *Genome Res.* 6:995–1001 (1996); and Livak et al. *PCR Methods and Applications* 4:357–362 (1995), all incorporated herein by reference). Since the exponential accumulation of the fluorescent signal directly reflects the exponential accumulation of the PCR amplification product, this reaction is monitored in real time. Real time RT-PCR may also be performed by adding reagents for RT-PCR and incubating reaction mixture at a temperature optimal for reverse transcription.

There are also many endpoint methods to detect and quantitate PCR products. These methods typically employ an intercalator or major or minor groove binder. For example, Higuchi et al. (*Bio/Technology* 10:413–417 (1992) and 11:1026–1030 (1993)) describe a method for real-time PCR product quantitation by measuring the increase in ethidium bromide intensity during amplification with a charge-coupled device (CCD) camera. Ishiguro et al. (*Anal. Biochem.* 229:207–213 (1995)) describe the use of various intercalaters to quantitate PCR amplification products.

Quantitation of nucleic acids may also be achieved by diluting or dividing a solution containing the nucleic acid of interest. The polynucleotide amplification reactions may be performed on the diluted or divided reaction volumes until no subject nucleic acid molecules are amplifiable in the reaction volumes. The number of reaction volumes and the dilution factor can determine the number of the nucleic acid molecules in a solution.

If a solution (e.g. 100 ul) containing 1000 molecules of nucleic acid of interest is diluted to 10,000 ul and then divided into 1000 reaction volumes, each reaction volume (10 ul) contains about 0.1 ul of the original undiluted solution and theoretically 1 molecule of the nucleic acid of interest. If a polynucleotide amplification reaction is performed on each of the 1000 reaction volumes, the number of reaction volumes where amplification occurs is theoretically 1000. Of course, the number of reaction volumes where nucleic acid of interest is amplified is almost certainly less than 1000, because some reaction volumes may not get any molecule of nucleic acid of interest (i.e. some reaction volumes get two or more molecules by chance or clumping of molecules) and/or because the efficiency of amplification reaction is less than 100%. However, as the dilution factor increases, multiple seeding of nucleic acids in each reaction volume will decrease and more and more reaction volumes will receive no nucleic acid of interest because of low concentration. When the number of reaction volume where nucleic acid of interest is amplified is substantially lower than the number of reaction volumes, e.g. less than half, the concentration of nucleic acid of interest may be accurately determined by counting the number of the reaction volume where the nucleic acid of interest is amplified and correcting it with the dilution factor. In addition, by carrying out this process with known standard amounts of nucleic acids, the efficiency of amplification reaction may be measured and subsequently used as a correction factor. For example, a solution of 100 ul contains unknown amount of nucleic acid of interest. The solution may be diluted to 10,000 ul and then divided into 1000 reaction volumes with each reaction volume (10 ul) containing about 0.1 ul of the original undiluted solution. If polynucleotide amplification reactions are performed in 1000 reaction volumes and about 90 reaction volumes are determined to have nucleic acid of interest amplified, the number of molecules present in the original undiluted solution is about 90 (dilution factor =1) and concentration of the nucleic acid of interest may also be determined if the molecular weight of the nucleic acid is known.

C. Other reactions

The instant method and apparatus may be used to investigate large numbers of molecular binding interactions, for example, sequence-specific interactions between polynucleotides (or modifications thereof) and polypeptides (or modifications thereof). The array assembly may be utilized to screen large numbers of polypeptides with different sequences for binding to a particular polynucleotide sequence or a large number of polynucleotides with different sequences for binding to a particular polypeptide. Either polynucleotides or polypeptides may be immobilized on one array, although it is possible that none is immobilized. Other molecular binding interactions, such as nucleic acid hybridization, inhibitor-enzyme, receptor-antagonist, drug-DNA, antibody-antigen, toxin-carbohydrate, protein-carbohydrate, and glycoprotein-receptor reactions may also be screened on a large scale using similar methods (see, e.g., Schullek et al., *Anal. Biochem.* 246:20–29 (1997), Pandey et al., *Nature* 405:837–846 (2000), de Wildt et al., *Nature Biotechnol.* 18:989 (2000), Uetz et al., *Nature* 403:623 (2000), and White *Annu. Rev. Pharmacol. Toxicol.* 40:133–157 (2000), all incorporated herein by reference).

For example, a combinatorial peptide library of potential enzyme inhibitors may be synthesized via an o-nitrobenzyl linker to a first solid support. Enzymes with buffers may be confined to reaction wells on a second solid support. After array assembly, potential enzyme inhibitors may be released by photolysis. A labeled enzyme substrate may be added to each reaction well. Enzyme inhibition may be identified and quantified using an optical system.

Polypeptides may be immobilized on solid supports and assayed for their functions. In one method, recombinant proteins (e.g., GST-fusion proteins) may be immobilized on a first solid support. Cell lysates containing interaction partners may be confined on a second array (e.g., in reaction wells). After array assembly, the system may be washed to remove unbound material. The bound proteins may be identified by known spectroscopic methods in the art. In another method, the yeast two-hybrid system may also be applied to array-based analysis. Yeast cells may be transformed with individual open reading frame-activation domain fusions and grown on a first array surface. Such array may then probed in a mating assay with yeast cells containing ORF-DNA-binding domain fusions on a second array.

IV. Probe Designs for Sequence Variation Detection or Polynucleotide Quantitation In detecting sequence variations or quantitating polynucleotides, amplified nucleic acids are frequently determined by analyzing the extent of hybridization. The fundamental aspect of this method is the discrimination of hybridization stability between the match and the mismatch. A recurring problem to this discrimination is that a perfect match in A/T rich hybridization complexes would often have a lower stability than a mismatch in G/C rich hybridization complexes. This dependency of stability on base composition may lead to false positives or false negatives. Therefore, for successful and reliable detection, several factors in probe selection may be considered. See Cantor and Smith, *Genomics: the science and technology behind the human genome project*, John Wiley & Sons (1999).

A. Polynucleotide Sequence and Length

One of the factors influencing hybridization performance of a polynucleotide probe is base composition. It is well known that sequences rich in G/C are more stable than sequences with lower G/C content. The solution melting temperature (Tm) of a polynucleotide, at which 50% of the polynucleotide is hybridized and 50% is not hybridized, is often used as a practical indicator of the hybridization strength of a polynucleotide probe of a given base composition. Methods for measuring Tm of a polynucleotide are well known in the art. See, e.g., Cantor and Schimmel, *Biophycical Chemistry*, San Francisco, W. H. Freeman (1980), incorporated herein by reference. There are also many ways to calculate Tm using mathematical algorithm. A widely used rule of thumb is two degree of increase in Tm by adding an A/T base pair and four degree of increase in Tm by adding a G/C base pair. This simple formula may be further modified to take into account of the ionic strength and solvent effect. For example, Tm may be calculated using the formula:

$$Tm = 81.5 + 16.6 \ (\log \ Na^+) + 0.41 \times \% \ of \ G/C - 600/n - 0.65 \times \% \ of \ formamide$$

Where $Na^+$ is sodium concentration, n is length of polynucleotide.

A more reliable formula to calculate Tm is available based on the interactions between a particular base and its nearest neighbors, i.e., the nearest-neighbor model. An enthalpy and entropy for each nearest neighbor combination of two adjacent base pairs (AA, AC, AG, AT, CA, CC, CG, CT, GA, GC, GG, GT, TA, TC, TG, and TT) have been established based on the extensive melting experiments using various polynucleotide sequences. Thermodynamic coefficients of nearest-neighbor models are available for DNA/DNA, DNA/RNA, and RNA/RNA hybridizations. Therefore, free energy of hybridization of two sequences at any temperature in solution may be calculated. See, e.g., U.S. Pat. No. 5,556,749, Hyndman, D., et al., *BioTechniques* 20(6):1090–1097 (1996), Mitsuhashi, M., *J. Clinical Laboratory Analysis* 10:277–284 (1996), Wetmur, J., *Critical Reviews in Biochemistry and Molecular Biolog*, 26:227–259 (1991), Rychlik et al., *Nucleic Acids Res.* 17:8543–8551 (1989), and Rychlik et al., *Nucleic Acids Res.* 18:6409–6412 (1990), all incorporated herein by reference.

The hybridization behavior of immobilized polynucleotide probes on a solid support is different from that in solution. Therefore, a more empirical approach is necessary to predict and modulate hybridization behavior of array-immobilized polynucleotide probes. Additional melting temperature experiments on solid supports may be conducted to more accurately characterize the thermodynamics and kinetics of hybridization behaviors of polynucleotide probes on an array. See Cantor and Smith, supra. Despite the differences in solid phase and solution phase kinetic and thermodynamic hybridization profiles, many variables affecting melting temperatures for solution hybridization, such as the effects of length, temperature, ionic strength, and solvent, are applicable for hybridization on solid supports.

Tm or free energy of hybridization may be evaluated based on base compositions, polynucleotide length, ionic strength, and thermodynamic parameters. High G/C content polynucleotide probes with a few mismatches may exhibit more stable hybridization than AT-rich polynucleotides without mismatches. Mismatches in the middle of the probe sequence are more consequential for hybridization than those at the 5' or 3' end. Shorter probe lengths may provide the maximum mismatch destabilization and result in the greater match to mismatch ratios. However, this advantage is partially offset by the wide range of Tm values for short probes, depending on their specific sequence composition. For example, probes with 17 nucleotides long with a single base difference may differ by 5° C. in Tm. If an array with equal length polynucleotide probes is used, baseline hybridization may yield wide range of signal intensities due to wide range of Tm values.

One skilled in the art will appreciate that in order to increase or decrease the melting temperature of a probe, it may be desirable to add, delete or change one or more bases in the probes. In certain embodiments of the inventions, polynucleotide probes with similar solution melting temperatures may be selected. The length of a polynucleotide probe may be changed, for example, by less than about 10, 5, 4, 3, 2 or 1 nucleotides.

Consideration of secondary structure may also play a role in evaluating hybridization performance of polynucleotide probes, especially when high hybridization temperature to denature secondary structures may not be applied. If polynucleotides form secondary structure such as hairpins or triple helixes, intramolecular hybridization within polynucleotides may be energetically and kinetically favorable and they may not be available for hybridization to the target sequences. See Mitsuhashi, M., *J. Clinical Laboratory Analysis*, supra.

In some instances, the presence of frequently appearing short subsequences may also be a factor for designing optimal polynucleotide sequences. For example, if polynucleotides contain a poly T or poly A stretch, such polynucleotides may cross-hybridize to poly(A)-mRNA or cDNA. If polynucleotides contain TATA-like sequences, such polynucleotides may bind to the promoter region of various genes.

A wide range of probe length may be used. Longer probes do not necessarily improve their sensitivity, because long probes usually exhibit higher Tm than that of actual assay conditions, allowing more mismatches. Although shorter probes increase the chances of nonspecific appearance of such sequences in the target sequences, they may exhibit a much higher penalty on mismatches. Therefore, one may design optimal probes based on their hybridization performance, instead of the length of the probes. In preferred embodiments of the present invention, the length of polynucleotide probes ranges from about 10 to about 100 nucleotides, preferably from about 10 to about 50 nucleotides, more preferably from about 15 to about 35 nucleotides.

B. Polynucleotide analogs

An alternative approach to even out base composition effects comprises the modification of one or more natural deoxynucleosides (or polynucleotide analogs) which forms a base pair whose stability is very close to that of the other pair. Polynucleotide analogs include base and sugar phosphate backbone analogs.

Any base analogs that induce a decrease in stability of the three G/C hydrogen bonds or an increase in stability of the two A/T hydrogen bonds may be used. For example, one can substitute 2,6-diamino purine for A, which gives 2-$NH_2$A/T base pair having a stability similar to that of the G/C base pair. One may also select C derivatives, in which one hydrogen of the exocyclic amino group at position 4 is substituted by an alkyl group such as methyl, ethyl, n-propyl, allyl or propargyl groups. For example, a $G^{4Et}C$ base pair has stability similar to that of the A/T base pair. Typically, it may be easier to find a modified G/C base pair whose stability is similar to that of an A/T natural base pair than to design a modified A/T base pair whose stability is close to that of a G/C natural base pair. In addition, preparation of polynucleotides containing C analogs may be simpler than that of polynucleotides built with G analogs and modification of only one base pair rather than both may simplify the preparation of polynucleotides containing one or several modified nucleosides. Analogs that increase base stacking energy, such as pyrimidines with a halogen at the C5-position (e.g. 5-bromoU, or 5-ChloroU), may also be used. One may also use the non-discriminatory base analogue, or universal base, such as 1-(2-deoxy-D-ribfuranosyl)3-nitropyrrole. This class of analogue maximizes stacking while minimizing hydrogen-bonding interactions without sterically disrupting a hybridization complex. See Nguyen, H., et al., *Nucleic Acids Research* 25(15) 3059–3065 (1997) and Nguyen, H., et al., *Nucleic Acids Research* 26(18):4249–4258 (1998), both incorporated herein by reference.

The highly charged phosphodiesters in natural nucleic acid backbone may be replaced by neutral sugar phosphate backbone analogues. The polynucleotide probes with uncharged backbones may be more stable, as in these analogs, the electrostatic repulsion between nucleic acid strands is minimized. As an example, phosphotriesters in which the oxygen that is normally charged in natural nucleic acids is esterified with an alkyl group may be used.

Another class of backbone analogs is polypeptide nucleic acids (PNAs), in which a peptide backbone is used to replace the phosphodiester backbone. The stability of PNA-DNA duplex is essentially salt independent. Thus low salt may be used in hybridization procedures to suppress the interference caused by stable secondary structures in the target. PNAs are capable of forming sequence-specific duplexes that mimic the properties of double-strand DNA except that the complexes are completely uncharged. Furthermore, because the hybridization stability of PNA-DNA is higher than that of DNA-DNA, binding is more specific and single-base mismatches are more readily detectable. See, e.g., Giesen, U. et al., *Nucleic Acids Research* 26(21):5004–5006 (1998), Good, L., et al., *Nature Biotechnology* 16:355–358 (1998), and Nielsen, P., *Current Opinion in Biotechnology* 10:71–75 (1999), all incorporated herein by reference.

Another option to modulate the hybridization performance of polynucleotide probes is the replacement of naturally occurring nucleic acids have 3'–5' phosphodiester linkage. Polyribonucleotides with 2'5' linkage which give complexes with lower melting temperature than duplexes formed by 3'–5' polynucleotides with the same sequence may be employed. See Kierzek, R., et al., *Nucleic Acids Research* 20(7):1685–1690 (1992), incorporated herein by reference.

Another method for optimizing hybridization performance is using polynucleotides containing C-7 propyne analogs of 7-deaza-2'-deoxyguanosine and 7-deaza-2'-deoxyadenosine (Buhr et al., *Nucleic Acids Res.* 24:2974–2980 (1996), incorporated herein by reference) or C-5 propyne pyrimidines (Wagner et al., *Science* 260:1510–3 (1993), incorporated herein by reference). These analogs may be particular useful in gene expression analysis.

C. Hybridization environment

Hybridization performance of polynucleotide is also dependent on the hybridization environment, for example, the concentrations of ions and nonaquous solvents. The hybridization performance of polynucleotide probes may be modulated by changing the dielectric constant and ionic strength of the hybridization environment. Salt concentrations, such as Na, Li, and Mg, may have an important influence on hybridization performance of polynucleotide probes.

Reagents that reduce the base composition dependence of hybridization performance may be used to alter the hybridization environment of array-immobilized polynucleotide probes. For example, high concentrations of tetramethylammonium salts (TMAC), N,N,N,-trimethylglycine (Betain) may be added to target nucleic acid mixture. At suitable concentrations typically at multimolar concentrations, these reagents may equalize the Tm of polynucleotides that are pure A/T and those that are pure G/C and thus increase the discrimination between perfect matches and mismatches. See, Von Hipppel et al., *Biochemistry*, 3:137–144 (1993), incorporated herein by reference.

Denaturing reagents that lower the melting temperature of double stranded nucleic acids by interfering with hydrogen bonding between bases may also be used.

Denaturing agents, which may be used in hybridization buffers at suitable concentrations (e.g. at multimolar concentrations), include formamide, formaldehyde, DMSO ("dimethylsulfoxide"), tetraethyl acetate, urea, GuSCN, and glycerol, among others.

Chaotropic salts that disrupt van der Waal's attractions between atoms in nucleic acid molecules may also be used. Chaotropic salts, which may be used in hybridization buffers at suitable concentrations (e.g. at multimolar concentrations), include, for example, sodium trifluoroacetate, sodium tricholoroacetate, sodium perchlorate, guanidine thiocyanate, and potassium thiocyanate, among others. See, Van Ness, J., et al., *Nucleic Acids Research* 19(19):5143–5151 (1991), incorporated herein by reference.

Renaturation accelerants that increase the speed of renaturation of nucleic acids may also be used. They generally have relatively unstructured polymeric domains that weakly associate with nucleic acid molecules. Accelerants include cationic detergents such as, CTAB ("cetyltrimethylammonium bromide") and DTAB ("dodecyl trimethylammonium bromide"), and, heterogenous nuclear ribonucleoprotein ("hnRP") A1, polylysine, spermine, spermidine, single stranded binding protein ("SSB"), phage T4 gene 32 protein and a mixture of ammonium acetate and ethanol, among others. See, Pontius, B., et al., *Proc. Natl. Acad. Sci. USA* 88:82373–8241 (1991), incorporated herein by reference.

One of skill in the art would appreciate that there are many other ways to modulate the hybridization performance of polynucleotides by changing the hybridization environment of polynucleotide probes. One method is changing the length of spacer that tethers polynucleotide probe to the array surface. It has been demonstrated that steric factors are important in increasing the efficiency of hybridization between polynucleotide probes and target nucleic acids. See, Southern et al., *Nucleic Acids Research,* 20(7):1679–1684 (1992), incorporated herein by reference. Methods for reducing non-specific binding to an array by surface modifications and probe modifications are described in WO 99/54509, incorporated herein by reference.

An alternative approach for enhancing the discrimination between matched and mismatches is applying electric current to polynucleotide probes which destabilize mismatches relative to matches. See, e.g., U.S. Pat. No. 5,929,208.

In some instances, the local concentration of polynucleotide probes or the concentration of target nucleic acids may be varied to allow maximum discrimination between matches and mismatches. In some instances, local concentrations of polynucleotide probes may be higher than target nucleic acids. Such high local DNA probe concentrations may generate high local charge densities and promote the undesirable association of probes that may interfere with target binding. High local probe concentration may also permit the simultaneous binding of target molecules to multiple probes, and may sterically prohibit access of target to the probes. If polynucleotide probes are at lower concentrations compared with the target sequence, the kinetics and thermodynamics of the hybridization may also be affected. See, Cantor and Smith, supra.

The polynucleotide probe set may also include control probes. One class of control probes is the mismatch probes. A mismatched probe is a probe whose sequence is deliberately selected not to be perfectly complementary to a reference sequence. In other words, mismatch probes are probes identical to their corresponding perfectly complementary probes except the presence of one or more mismatched bases. Therefore, under suitable hybridization conditions, the perfectly matched would be expected to hybridize with its target sequence, but mismatch probes would not hybridize or would hybridize to a significantly lesser extent, thus providing a control for non-specific binding or cross-hybridization. Although one or more mismatches may be located anywhere in the mismatch probe, probes are often designed to have the mismatch locate at or near the center of the probe such that the mismatch is most likely to destabilize the hybridization complex with the target sequence. In addition, the mismatch site is typically not the location of the sequence variation to be determined, but is within several nucleotides (e.g., less than 5) on the 5' or 3' side of the sequence variation location. For example, a probe set for a known biallelic SNP may contain two groups of mismatch probes based on two reference sequences constituting the respective polymorphic forms. Each group of mismatch probes may include at least two sets of probes, which each set contains a series of probes with a mismatch at one nucleotide 5' and 3' to the polymorphic site.

Control probes may also include normalization probes. Normalization probes are those perfectly complementary to a known polynucleotide sequence that is added to the target nucleic acids. Normalization probes provide a control for variation in hybridization condition, signal intensity, and other factors that may cause the signal of a perfect hybridization to vary between arrays. Normalization probes may be located throughout the array to control for spatial variation in hybridization intensity. For example, they may be located at the corners, edges or middle of the array.

The number of polynucleotide probes for a sequence variation or a gene expression may vary depending on the nature of sequence variation, gene expression, and level of resolution desired. At least about 2, 5, 10, 20, or 50 polynucleotide probes may be employed for each sequence variation or each gene. Each probe in both sequence variation determination and gene profiling may be about 10 to 100 nucleotides long, e.g. shorter than about 20, 30, 40, 50, 60, 70, 80, or 90 nucleotides long. In the case of overlapping polynucleotides probes, the overlap may be about 1 to 50 bases, preferably below 30, 20, 10, or 5 bases.

V. Hybridization Conditions and Signal Processing

The hybridization can take place in the same reaction site or well as the amplification reactions. Generally, incubation may be at temperatures normally used for hybridization of nucleic acids, for example, between about 20° C. and about 75° C., e. g., above about 30° C. 40° C., 50° C., 60° C., or 70° C. The amplified nucleic acid may be incubated with the array for a time sufficient to allow the desired level of hybridization between the amplified product and any complementary probes in the array, usually in about 10 minutes to several hours. But it may be desirable to hybridize longer. After incubation with the hybridization mixture, the array is usually washed with the hybridization buffer, thus removing unhybridized molecules. This leaves only hybridized target molecules. Then the array may be examined to identify the polynucleotide probes to which the amplified product has hybridized.

Suitable hybridization conditions may be determined by optimization procedures or experimental studies. Such procedures and studies are routinely conducted by those skilled in the art. See e.g., Ausubel et al., *Current Protocols in Molecular Biology, Vol.* 1–2, John Wiley & Sons (1989) and Sambrook et al., Molecular Cloning A Laboratory Manual, 2nd Ed., Vols. 1–3, Cold Springs Harbor Press (1989). For example, hybridization and washing conditions may be selected to detect substantially perfect matches. They may also be selected to allow discrimination of perfect matches and one base pair mismatches. They may also be selected to permit the detection of large amounts of mismatches. As an example, the wash may be performed at the highest stringency that produces results and that provides a signal intensity greater than approximately 10% of the background intensity.

The hybridization intensities indicating the hybridization extent between the amplified nucleic acid and polynucleotide probes may be determined and compared. The differences in hybridization intensities are evaluated. One of skilled in the art will appreciate that methods for evaluating the hybridization results vary with the nature of probes, sequence variations, gene expressions, and labeling methods. For example, quantification of the fluorescence intensity is accomplished by measuring probe signal strength at locations where probes are present. Comparison of the absolute intensity of array-immobilized polynucleotide probes hybridized to amplified nucleic acids with intensities produced by control probes provides a measure of the sequence variations or the relative expression of the genes.

Quantification of the hybridization signal can be by any means known to one of skill in the art. For example, quantification may be achieved by the use of a confocal fluorescence microscope. The methods of measuring and analyzing hybridization intensities may be performed utilizing a computer. The computer program typically runs a software program that includes computer code for analyzing hybridization intensities measured. Signals may be evaluated by calculating the difference in hybridization signal intensity between each polynucleotide probe, its related probes, and control probes. The differences can be evaluated for each sequence variation or each gene.

Background signals typically contribute to the observed hybridization intensity. The background signal intensity refers to hybridization signals resulting from non-specific binding, or other interactions, e.g., between amplified nucleic acids and array surface. Background signals may also be produced by the array component itself. A single background signal may be calculated for an array or a different background signal may be calculated for each sequence variation or each gene expression analysis. For example, background may be calculated as the average hybridization signal intensity for the lowest 5% to 10% of the probes in the array, or where a different background signal is calculated for each sequence variation or gene, for the lowest 5% to 10% of the probes for each sequence variation or gene. Background signal may also be calculated as the average hybridization signal intensity produced by hybridization to probes that are not complementary to any sequence found in the sample (e.g. probes directed to nucleic acids of the opposite sense or to genes not found in the sample). Background may also be calculated as the average signal intensity produced by regions of the array that lack any probes at all. Preferably the difference in hybridization signal intensity between each probe and its control probes is detectable, e.g. greater than about 10%, 20%, or 50% of the background signal intensity. In some instances, only those probes where difference between the probe and its control probes exceeds a threshold hybridization intensity (e.g. preferably greater than 10%, 20%, or 50% of the background signal intensity) are selected. Thus, only probes that show a strong signal compared to their control probes are selected.

The identity of each sequence variation may be estimated using known methods in the art. If the target is present, the perfectly matched probes should have consistently higher hybridization intensity than the mismatched probes. Therefore, in sequence variation determinations, one of the four A, T, C, G substituted probes may have a significantly higher signal than the other three. A comparison of the intensities of four corresponding probes may reveal the identity of one sequence variation in the target sequence. For example, the highest intensity probe may be compared to the second highest intensity probe. The ratio of the intensities may be compared to a predetermined ratio cutoff, which is a number that specifies the ratio required to identify a sequence variation. For example, if the ratio cutoff is 1.2, a ratio of 1.4 is greater than the cutoff and the sequence variation may be determined. Of course, ratio cutoff may be adjusted to produce optimal results for a specific array and for a specific sequence variation.

In addition to comparing to mismatch probes, the hybridization intensity may be compared to other control probes, such as normalization probes. For example, probe intensity of amplified nucleic acid may be compared to that of a known sequence. Any significant changes may indicate the presence or absence of a sequence variation. Statistical method may also be used to analyze hybridization intensities in determining sequence variations or gene expression levels. For example, mismatch probe intensities may be averaged. Means and standard deviations may be calculated and used in determining sequence variations and profiling gene expressions. Complex data processing and comparative analysis may be found in EP 717 113 A2 and WO 97/10365, both incorporated herein by reference.

VI. Target Nucleic Acid Preparation and Reactant Labeling

It will be appreciated by one of skill in the art that the reactions using the instant invention may be monitored or quantitated by directly or indirectly labeling reactants, reaction intermediates, or reaction products with detectable labels, prior to, during, or after the initiation of reactions. Detectable labels suitable for use in the present invention include any composition detectable by spectroscopic, photochemical, biochemical, immunochemical, electrical, optical or chemical means. Useful polynucleotide labels in the present invention include biotin for staining with labeled streptavidin conjugate, magnetic beads (e.g., Dynabeads™), fluorescent molecules (e.g., fluorescein, texas red, rhodamine, green fluorescent protein, FAM, JOE, TAMRA, ROX, HEX, TET, Cy3, C3.5, Cy5, Cy5.5, IRD41, BODIPY and the like), radiolabels (e.g., $^{3}H$, $^{251}I$, $^{35}S$, $^{34}S$, $^{14}C$, $^{32}P$, or $^{33}P$), enzymes (e.g., horse radish peroxidase, alkaline phosphatase and others commonly used in an ELISA), calorimetric labels such as colloidal gold or colored glass or plastic (e.g., polystyrene, polypropylene, latex, etc.) beads, mono and polyfunctional intercalator compounds. Means of detecting such labels are well known to those of skill in the art. For example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

Any nucleic acid specimen, in purified or non-purified form, can be utilized as the target sequence nucleic acid. The amplification reaction may amplify, for example, DNA or RNA, including mRNA, wherein DNA or RNA may be single stranded or double stranded. In the event that RNA is to be used as a template, enzymes and conditions optimal for reverse transcribing RNA to DNA may be utilized. In addition, a DNA-RNA hybrid which contains one strand of each may be utilized. A mixture of nucleic acids may also be employed, or the nucleic acids produced in a previous amplification reactions.

The target nucleic acids may be prepared from human, animal, viral, bacterial, fungal, or plant sources using known methods in the art. For example, target sample may be obtained from an individual being analyzed. For assay of genomic DNA, virtually any biological sample is suitable. For example, convenient tissue samples include whole blood, semen, saliva, tears, urine, fecal material, sweat, buccal, skin and hair. For assay of cDNA or mRNA, the tissue sample must be obtained from an organ in which the target nucleic acid is expressed. For example, if the target nucleic acid is a cytochrome P450, the liver is a suitable source. The target nucleic acids may also be obtained from other appropriate source, such as nuclear RNA, rRNA, tRNA, M 13, plasmid or lambdavectors, and cosmid or YAC inserts. The target may be preferably fragmented before application to the array to reduce or eliminate the formation of secondary structures in the target. The fragmentation may be performed using a number of methods, including enzymatic, chemical, thermal cleavage or degradation. For example, fragmentation may be accomplished by heat/$Mg^{2+}$ treatment, endonuclease (e.g., DNAase 1) treatment, restriction enzyme digestion, shearing (e.g., by ultrasound) or NaOH treatment. Examples of target nucleic acid preparation are described in e.g., WO 97/10365, incorporated herein by reference.

Definitions

As used herein, the term "linker" refers to an anchoring group that serves to anchor or tether a molecule to a solid support during solid phase synthesis. The linker is sometimes the point of cleavage following synthesis.

As used herein, the terms "polynucleotide" and "nucleic acid" refer to naturally occurring polynucleotides, e.g. DNA or RNA. This term also refers to analogs of naturally occurring polynucleotides. The polynucleotide may be double stranded or single stranded. This term is used without referring to a specific length. The polynucleotides may be labeled with radiolabels, fluorescent labels, enzymatic labels, proteins, haptens, antibodies, sequence tags.

As used herein, the term "polynucleotide amplification reaction" refers to a broad range of techniques for increasing the number of copies of specific polynucleotide sequences. Typically, amplification of either or both strand of the target nucleic acid comprises the use of one or more nucleic acid-modifying enzymes, such as a DNA polymerase, a ligase, an RNA polymerase, or an RNA-dependent reverse transcriptase. Examples of polynucleotide amplification reaction include, but not limited to, polymerase chain reaction (PCR), nucleic acid sequence based amplification (NASB), self-sustained sequence replication (3SR), strand displacement activation (SDA), ligase chain reaction (LCR), Qβ replicase system, and the like.

As used herein, the term "polypeptide" refers to a polymer of amino acids without referring to a specific length. This term includes naturally occurring protein. The term also refers to modifications, analogues and functional mimetics thereof. For example, modifications of the polypeptide may include glycosylations, acetylations, phosphorylations, and the like. Analogues of polypeptide include unnatural amino acid, substituted linkage, etc. Polypeptides may be labeled with radiolabels, fluorescent labels, enzymatic labels, proteins, haptens, antibodies, sequence tags.

As used herein, the term "polynucleotide" refer to naturally occurring polynucleotide, e.g. DNA or RNA. This term does not refer to a specific length. Thus, this term includes oligonucleotide, primer, probe, gene, nucleic acid, etc. This term also refer to analogs of naturally occurring polynucleotides. Polynucleotides may be double stranded or single stranded. Polynucleotides may be labeled with radiolabels, fluorescent labels, enzymatic labels, proteins, haptens, antibodies, sequence tags, etc.

As used herein, the term "primer" refers to a polynucleotide, which is capable of annealing to a complementary template nucleic acid and serving as a point of initiation for template-directed nucleic acid synthesis, such as a polynucleotide amplification reaction. A primer need not reflect the exact sequence of the template but must be sufficiently complementary to hybridize with a template. Typically, a primer will include a free hydroxyl group at the 3' end. The appropriate length of a primer depends on the intended use of the primer but typically ranges from 12 to 40 nucleotides preferably from 15 to 40, most preferably from 20 to 40 nucleotides. The term primer pair (e.g., forward and reverse primers) usually means a set of primers including a 5' upstream primer that hybridizes with the 5' end of the target sequence to be amplified and a 3', downstream primer that hybridizes with the complement of the 3' end of the target sequence to be amplified.

As used herein, the term "probe" refers to a polynucleotide of any suitable length which allows specific hybridization to a polynucleotide. Probes may be attached to a label or reporter molecule. Typically, probes are at least about 10 nucleotides long.

As used herein, the term "reactant" refers to any component of a non-unimolecular reaction. A reactant may be a chemically or biologically reactive substance in a reaction.

As used herein, the term "sequence variation" of a polynucleotide encompasses all forms of polymorphism, mutations and haplotypes. A sequence variation may range from a single nucleotide variation to the insertion, modification, or deletion of more than one nucleotide. A sequence variation may be located at the exon, intron, or regulatory region of a gene.

Polymorphism refers to the occurrence of two or more genetically determined alternative sequences or alleles in a population. A biallelic polymorphism has two forms. A triallelic polymorphism has three forms. A polymorphic site is the locus at which sequence divergence occurs. Diploid organisms may be homozygous or heterozygous for allelic forms. Polymorphic sites have at least two alleles, each occurring at frequency of greater than 1% of a selected population. Polymorphic sites also include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements. The allelic form occurring most frequently in a selected population is sometimes referred to as the wild type form or the consensus sequence.

Mutations include deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues, such as liver, heart, etc and are not inherited in the germline. Germline mutations can be found in any cell of a body and are inherited.

A haplotype refers to the combination of sequence variations that co-exist on a chromosome.

The term "subsequence" refers to a polynucleotide sequence that comprises a part of a longer polynucleotide sequence.

Examples of the Preferred Embodiments

The following examples further illustrate the present invention. These examples are intended merely to be illustrative of the present invention and are not to be construed as being limiting.

EXAMPLE 1

Synthesis of DMT-protected o-nitrobenzyl Amidite

Figure 7:
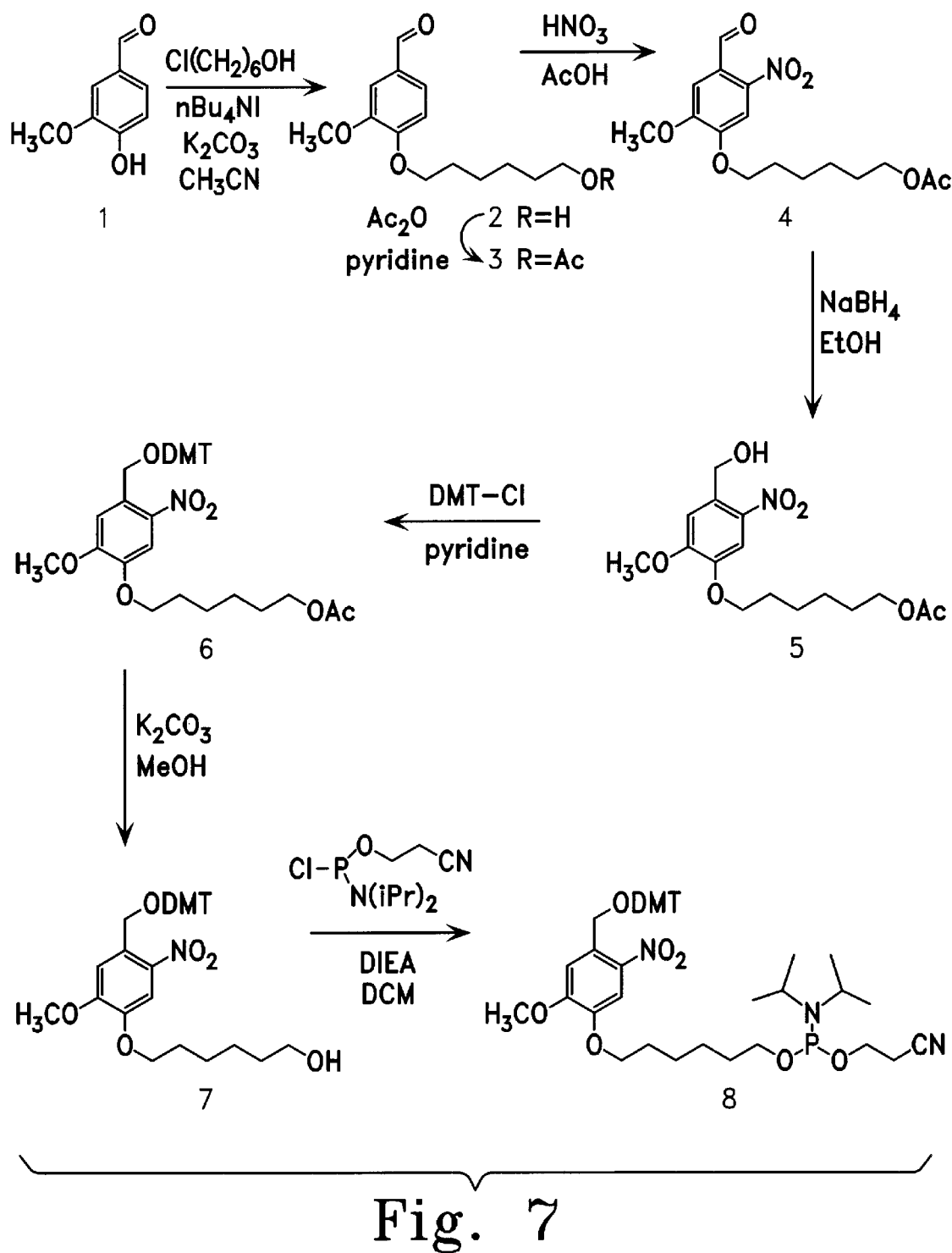
FIG. 7 illustrates a chemical synthesis of photocleavable DMT-protected o-nitrobenzyl amidite.

A schematic illustration of DMT-protected o-nitrobenzyl amidite synthesis is shown in FIG. 7.

6-(4-Formyl-2-methoxyphenoxy)hexan-1-ol (2)

A flame-dried, 100 mL round bottom flask equipped with a claisen arm and reflux condenser was charged, under argon, with vanillin (1, 1.0 g, 6.6 mmol), tetrabutylammonium iodide (369 mg, 1 mmol), and potassium carbonate (1.38 g, 10 mmol). These were suspended in 10 mL of anhydrous acetonitrile and then 6-chlorohexanol (1.05 ml, 7.9 mmol) was added dropwise. The reaction was protected from light and refluxed for 15 hours at which time TLC analysis showed complete consumption of the starting material. The solvent was evaporated in vacuo and the residue was then dissolved in 50 mL of ethyl acetate and extracted with water (2×100 mL), brine (1×100 mL), and water (1×100 mL). The organic layer was dried over magnesium sulfate, filtered, and the solvent was evaporated in vacuo to give 1.5 g (90%) of 2 as a white solid. $R_f$=0.29 (33% ethyl acetate/hexane). Mp 55.0–56.0° C. $^1$H NMR (400 MHz, DMSO-d6): δ9.83 (s, 1), 7.53 (dd, J=2.0 Hz, 8.0 Hz, 1), 7.39 (d, J=2.0 Hz, 1), 7.17 (d, J=8.4 Hz, 1), 4.36 (t, J=5.2 Hz, 1), 4.07 (pt, J=2.4 Hz, 2.8 Hz, 2), 3.83 (s, 3), 3.39 (dd, J=5.6 Hz, 11.6 Hz, 2), 1.75 (m, 2), 1.45–1.34 (m, 6) ppm.

6-(4-Formyl-2-methoxyphenoxy)hexyl acetate (3).

A flame-dried, 250 mL round bottom flask was charged, under argon, with 2 (10 g, 39.6 mmol) and this was dissolved in 50 mL of anhydrous pyridine and the flask was protected from light. To this solution was added acetic anhydride (9.3 mL, 98.8 mmol) dropwise at a rate of 0.5 mL/minute. The solution was stirred at room temperature for 30 minutes at which time all of the starting material had been consumed. The solvent was evaporated with reduced pressure and then toluene was added to remove excess pyridine. Evaporation of the solvent in vacuo gave 11.5 g (99%) of 3 as an off-white solid. $R_f$=0.74 (33% ethyl acetate/hexane). Mp 74.0–75.0° C. $^1$H NMR (400 MHz, DMSO-d6): δ9.83 (s, 1), 7.53 (dd, J=1.6 Hz, 8.4 Hz, 1), 7.39 (d, J=2.0 Hz, 1),), 7.17 (d, J=8.4 Hz, 1), 4.07 (t, J=6.4 Hz, 2), 4.00 (pt, J=6.4 Hz, 6.8 Hz, 2), 3.83 (s, 3), 2.00 (s, 3) 1.74 (m, 2), 1.58 (m, 2), 1.4–1.35 (m, 4) ppm.

6-(4-Formyl-2-methoxy-5-nitrophenoxy)hexyl acetate (4).

A 250 mL round bottom flask was charged with 3 (10 g, 34 mmol) and was then placed in an ice bath. To this was added a 20% v/v solution of fuming nitric acid in acetic acid (40 mL total volume) at a rate of 1.0 mL/minute with stirring. At the end of addition the bath was removed, the reaction was protected from light, and stirred at room temperature for 4 hours. At this time the solution was poured over crushed ice (200 mg). Water was added and the product was extracted with ethyl acetate (3×200 mL). The combined organics were washed with brine (1×200 mL), saturated sodium bicarbonate (1×200 mL), and water (1×200 mL), dried over magnesium sulfate, and filtered. The solvent was evaporated in vacuo to give 10.6 g of 4 (92%) as an orange-red solid. $R_f$=0.80 (33% ethyl acetate/hexane). Mp 79.8–81.5° C. $^1$H NMR (400 MHz, DMSO-d$_6$): δ7.69 (s, 1), 7.37 (s,1), 4.17 (pt, J=6.4, 6.8 Hz, 2), 4.0 (t, J=6.8 Hz, 2), 3.95 (s,3), 1.99 (s, 3), 1.77 (m, 2), 1.59 (m, 2), 1.45–1.37 (m, 4) ppm.

6-(4-Hydroxymethyl-2-methoxy-5-nitrophenoxy)hexyl acetate (5)

A flame-dried, 250 mL round bottom flask was charged, under argon, with 4 (8 g, 23.6 mmol) and this was suspended in 35 mL of anhydrous ethanol. The flask was protected from light and then placed in an ice bath. Sodium borohydride (2.06 g, 54.3 mmol) was added in small portions and the reaction was allowed to stir at 0° C. for 180 minutes. At this time, saturated ammonium chloride (30 mL) was added slowly to the reaction mixture over a period of 20 minutes to minimize the gas evolution. Ethanol was evaporated in vacuo and the mixture was diluted with water (100 ml) and extracted with dichloromethane (3×100 mL). The combined organic layers were dried with magnesium sulfate, filtered, and the solvent was evaporated in vacuo to give orange oil. This oil was subjected to column chromatography (SiO$_2$, 75×200 mm, 1% triethylamine in dichloromethane) to give, following solvent evaporation, 7.25 g (90%) of 5 as a yellow solid. $R_f$=0.30 (33% ethyl acetate/hexane). Mp >220° C. $^1$H NMR (400 MHz, DMSO-d$_6$): δ7.67 (s, 1), 7.38 (s, 1), 5.55 (t, J=6.4 Hz, 1), 4.81 (d, J=6.4 Hz, 2), 4.04 (t, J=7.2 Hz, 2), 4.00 (t, J=7.6 Hz, 2), 3.91 (s, 3), 1.99 (s, 3), 1.76–1.72 (m, 2), 1.61–1.57 (m, 2), 1.45–1.37 (m, 4) ppm.

6-[4-(4,4'-Dimethoxytrityloxymethyl)-2-methoxy-5-nitrophenoxy)hexan-1-ol (7).

A flame-dried, 250 mL round bottom flask was charged, under argon, with 5 (5 g, 14.7 mmol) and this was dissolved in 45 mL of anhydrous pyridine. The flask was protected from light and 4,4'-dimethoxytrityl chloride (7.4 g, 22 mmol) was added in one portion. The solution was stirred at room temperature for 18 hours. Toluene was then added to the reaction flask and the solvent was evaporated in vacuo to give an oil. This process of toluene addition/evaporation was repeated twice and then water was added to the flask to remove the last trace of organic solvents. The residue was dissolved in 400 mL of ethyl acetate and water extractions (3×150 mL) were performed. The organic layer was dried over magnesium sulfate, filtered, and the solvent was evaporated in vacuo to give 6 as a yellow oil. This was taken to the next step without further manipulation. $R_f$=0.68 (33% ethyl acetate/hexane). $^1$H NMR (400 MHz, DMSO-d$_6$): δ7.60 (s, 1), 7.45–7.24 (m, 10), 6.90 (d, J=8.4 Hz, 4), 4.50 (s, 2), 4.04 (t, J=7.2 Hz, 2), 4.00 (t, J=7.6 Hz, 2), 3.95 (s, 3), 3.73 (s, 6), 1.99 (s, 3), 1.76–1.72 (m, 2), 1.61–1.57 (m, 2), 1.45–1.37 (m, 4) ppm.

A flame-dried, 250 ml round bottom flask was charged with 6 and this was dissolved in 100 mL of anhydrous methanol. The flask was protected from light and then potassium carbonate (2.6 g, 18.6 mmol) was added in one portion. The reaction was continued at room temperature for 30 minutes at which time TLC analysis showed complete consumption of the starting material. The solvent was evaporated in vacuo and the residue was then dissolved in 600 mL of dichloromethane and extractions performed with water (3×400 mL). The organic layer was dried over magnesium sulfate, filtered, and the solvent evaporated in vacuo to give a yellow oil. This oil was subjected to column chromatography (SiO$_2$, 75×200 mm, 1% triethylamine in dichloromethane) to yield, following solvent evaporation, 6.6 g (75%, 2 steps) of 7 as a waxy yellow solid. $R_f$=0.40 (33% ethyl acetate/hexane). $^1$H NMR (400 MHz, DMSO-d$_6$): δ7.60 (s, 1), 7.45–7.24 (m, 10), 6.90 (d, J=8.4 Hz, 4), 4.35 (t, J=4.8, 5.2, 2), 4.03 (pt, J=6.4, 6.8 Hz, 2), 3.95 (s, 3), 3.73 (s, 6), 3.73–3.71 (m, 2), 1.95–1.98 (m, 2), 1.44–1.36 (m, 6) ppm. $^{13}$C NMR (100 MHz, DMSO-d$_6$): δ158.6, 153.9, 146.9, 145.1, 139.1, 135.8, 130.3–127.3 (m), 113.8, 113.2, 110.4, 109.3, 87.0, 69.1, 63.0, 61.0, 56.4, 55.5, 32.9, 28.9, 25.7, 25.6 ppm.

6-[4-(4,4'-Dimethoxytrityloxymethyl)-2-methoxy-5-nitrophenoxy) hexyloxy-1-O-[O-(2-cyanoethyl)-N,N-diisopropylphosphoramidite (8).

A flame-dried, 250 ml round bottom flask was charged with 7 (6 g, 11.6 mmol). The system was protected from light and evacuated under reduced pressure for at least six hours. The system was back-filled with argon and 7 was dissolved in 50 mL of anhydrous dichloromethane. The system was placed in an ice bath and then diisopropylethylamine (10 mL, 58 mmol) was added followed by slow addition of 2-cyanoethyl-N,N-diisopropylchlorophosphoramidite (3.8 mL, 17.4 mmol). The ice bath was then removed and the reaction stirred at room temperature for 60 minutes. At this time, the reaction was quenched via the addition of 30 mL of methanol. The solvents were evaporated in vacuo and the residue was dissolved in dichloromethane and extracted with saturated sodium bicarbonate (1×300 mL). The organic layer was dried over magnesium sulfate, filtered, and the solvent evaporated in vacuo to give an orange-yellow oil. This oil was subjected to column chromatography (SiO$_2$, 75×200 mm, 1% triethylamine in dichloromethane) to yield, following solvent evaporation, 3.2 g (40%) of 8 as a faint orange oil. $R_f$=0.70 (33% ethyl acetate/hexane). $^1$H NMR (400 MHz, DMSO-d$_6$): δ7.60 (s, 1), 7.42–7.46 (m, 3), 7.21–7.37 (m, 7), 6.9 (d, J=8.4 Hz, 4), 4.50 (s, 2), 4.03 (t, J =6.4 Hz, 2), 3.95 (s, 3), 3.73 (s, 6), 3.71–3.73 (m, 2), 3.52–3.6 (m, 6), 2.74 (t, J=6.0 Hz, 2), 2.44 (m, 2), 1.75–1.72 (m, 2), 1.58–1.55 (m, 2), 1.41–1.39 (m, 2), 1.18–1.10 (m, 12) ppm. $^{31}$P NMR (162 MHz, DMSO-d$_6$): δ148.9, 147.1 ppm. $^{13}$C NMR (100 MHz, DMSO-d$_6$): δ158.8, 154.1, 147.1, 145.2, 139.3, 137.9, 136.0, 130.4, 130.1, 129.4, 128.7, 128.6, 128.1, 127.4, 125.8, 119.5, 113.9, 113.3, 110.6, 109.5, 87.1, 69.2, 63.6, 63.4, 63.1, 58.9, 58.7, 58.6, 56.6, 55.6, 55.4, 50.9, 50.7, 43.1, 42.9, 31.2, 31.1, 29.0, 25.6, 25.5, 25.0, 24.9, 24.8, 21.6, 20.4 ppm.

EXAMPLE 2

Polynucleotide Synthesis off of a Photocleavable Linker

Aminoalkylated controlled-pore glass resin was treated with a 20% v/v solution of piperidine in anhydrous dimethylformamide (DMF) at room temperature for 30 minutes. Next, the resin was washed in anhydrous DMF and a 0.1 M solution of N-α-(9-fluorenylmethoxycarbonyl)-O-trityl-L-homoserine (Fmoc-HoSer(Trt)-OH) in anhydrous DMF containing 0.1 M N-[(dimethylamino)-1H-1,2,3-triazol[4,5-b]pyridin-1-ylmethylene]-N-methylmethanaminium hexafluorophosphate N-oxide (HATU) and 0.2 M anhydrous diisopropylethylamine (DIEA) was introduced and allowed to react for 30 minutes at room temperature. The resin was treated with a 20% v/v solution of piperidine in anhydrous DMF for 15 minutes to remove the Fmoc group. The resin was washed in anhydrous DMF and then treated with a 25% v/v solution of acetic anhydride in pyridine for 30 minutes. The resin was then treated with a 3% w/v solution of trichloroacetic acid (TCA) in dichloromethane (DCM) for 10 minutes to remove the trityl group and give a terminal hydroxyl group to couple to compound 8.

Figure 8:
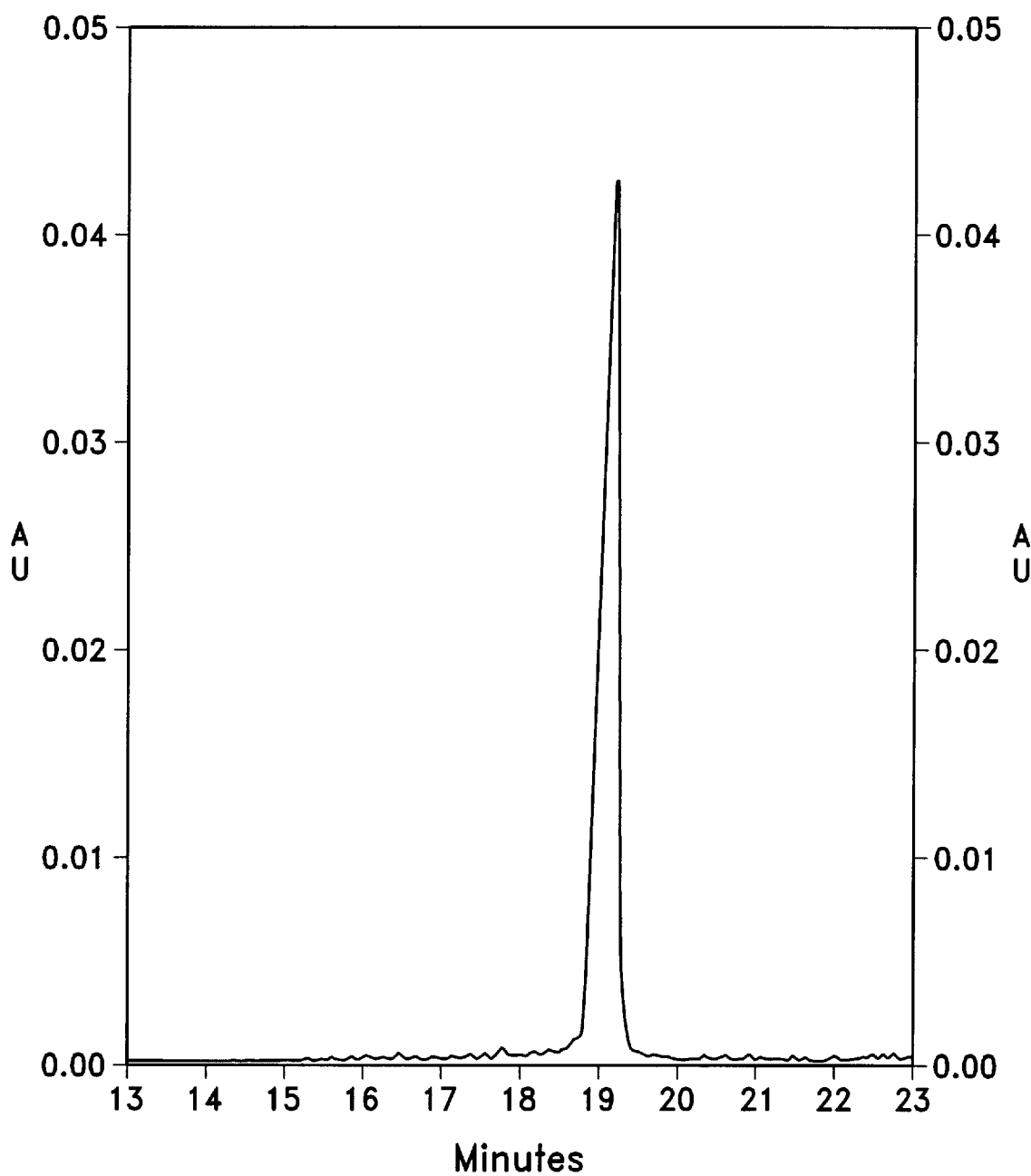
FIG. 8 illustrates capillary electrophoresis analysis of polynucleotides synthesized off of a photocleavable linker.
Figure 9:
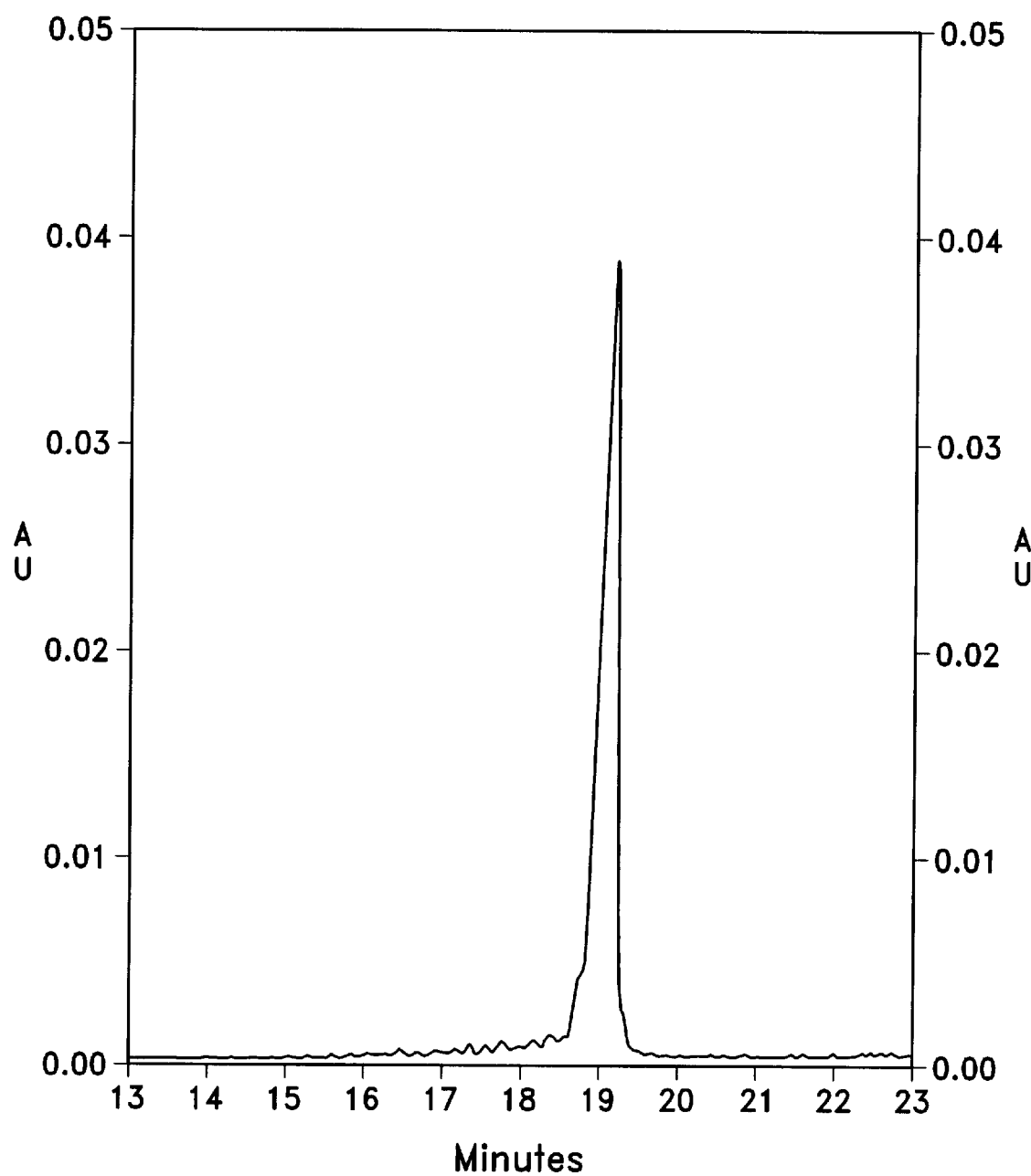
FIG. 9 illustrates capillary electrophoresis analysis of polynucleotides synthesized off of a photocleavable linker co-migrated with polynucleotides of the same sequence from a commercial source.

Coupling of 8 to the homoserine derivatized resin was accomplished through standard amidite chemistry (5-ethylthiotetrazole was used as the activator). Following benzylic DMT removal, a mixed sequence of 3'-CTC AAC CCG AAT CTC CG-5' (SEQ. ID. No. 1) was synthesized in the standard fashion on a 200 nmol scale. At the completion of the synthesis, the resin was treated with an aqueous solution of ammonia in order to deprotect the phosphate backbone and remove the heterocyclic protecting groups. No polynucleotide was detected in the eluent of these deprotection solutions. A portion of the resin was suspended in 18 MΩ water and subjected to photolysis. Using a converted lithography system, we delivered 16 mW/cm$^2$ (measured at 365 nm) of light for approximately 20 minutes. Cleavage of this polynucleotide from the resin gives a 3'-phosphate-terminated sample. It should be noted that no special purification was attempted (i.e. desalting column, HPLC, etc). An aliquot of the aqueous solution was then subjected to capillary electrophoresis. Capillary electrophoresis was carried out on a Beckman P/ACE 5000 system. Samples were injected electrokinetically onto a 37 cm×75 μm i.d. J&W Scientific 3% T 3% C μPAGE polyacrylamide gel filled column. Separation was done at 9 kV and the separation buffer used was Tris-borate pH 8.0 with 1M urea. The result is shown in FIG. 8. In addition, the sample was mixed with an authentic sample purchased from IDT, Inc (Coralville, IA, standard desalting purification) and subjected to CE analysis (FIG. 9). As can be seen in FIG. 9, the polynucleotides prepared from the resin terminated in 8 is as pure as that obtained commercially.

EXAMPLE 3

Preparation of Surface Derivatized Arrays

Glass slides were cleaned by sonication in a 2% solution of Micro 90 in Mill-Q water for 60 minutes at room temperature. The slides were then rinsed excessively with Milli-Q water and dried down with nitrogen. Next, the slides were exposed to an RF oxygen plasma (Plasmline421, Tegal, Novato, Calif.) for 60 minutes at 150 watts, 0.4 Torr, and 3.5 cc/min flow rate (Brzoska et al., Nature 360:719–721 (1992). The slides were further washed for 10' in a peroxysulfuric acid solution (70% $H_2SO_4$:15%$H_2O_2$, VWR, San Francisco, Calif.).

Immediately after oxygen plasma treatment, the slides were silanated with a 0.4% solution of 4-aminobutyldimethylmethoxysilane (ABS) (United Chemical Technologies, Bristol, Pa.) in anhydrous toluene (Aldrich, Milwaukee, Wis.) in a glove box under argon for 72 hours. The slides were then washed in anhydrous toluene with sonication for 15 minutes then rinsed in 95% ethanol (Aldrich) with sonication for 15 minutes. After drying each slide under nitrogen, the slides were cured for 30 minutes at 120° C. in an air oven.

Next, slides were coated with 3.5 micron layer of a positive photoresist (Microposit 1818; Shipley, Marlborough, Mass.) by spin coating photoresist (3.4 mls) at 1250 rpm for 30 seconds. After spin coating, the photoresist was soft baked for 30 minutes at 90° C. in an air oven. Next, the slides were photomasked by placing each slide onto a chromium mask (Image Technology, Palo Alto, Calif.) that had round features with each feature being 1 mm in diameter with center to center spacing of 2.0 mm with the photoresist side touching the mask. The chips were then exposed to near UV irradiation with a 365 nm 500 W columnated mercury lamp (45 mW/cm$^2$, AB-M, San Jose, Calif.) for 1.0 second. After exposure, the exposed photoresist was removed by placing the slides into a solution of Microposit 350 developer (1:1 in $H_2O$, Shipley, Marlborough, Mass.) for 30 seconds with agitation and then rinsed extensively with Milli-Q water and dried under argon.

The slides were then exposed to an RF plasma (Plasmline421) 150 watts, 0.4 Torr, and 3.5 cc/min flow rate, for 6.0 minutes to remove the ABS along with residual photoresist from the photolyzed regions. Next, the slides were silated with a 0.25% solution of (tridecafluoro-1,1,2,2-tetrahydrooctyl)-1-trichlorosilane (United Chemical Technologies, Bristol, Pa.) in anhydrous toluene (Aldrich) in an argon dry box for 10 minutes at room temperature and then washed in anhydrous toluene with sonication for 15 minutes. Finally, the photoresist covering the synthesis regions was stripped by sonication in acetone (Aldrich) then by washing in NMP (Aldrich) for 60 minutes at 70° C. and washed extensively in Milli-Q $H_2O$ to remove residual photoresist.

EXAMPLE 4

In situ Synthesis of Polynucleotides with a Cleavable Site

All derivatizations were performed in a chip reaction chamber. Briefly, two slides were placed with their patterned surfaces facing one another. The gasket and chips were secured by four steel binder clips. Reagents were introduced via syringe through a 27-gauge needle. The gas interior was displaced through an open 27-gauge needle while reagent was being injected with the syringe. At the end of the given reaction, the reagent was removed via syringe using an open 27-gauge needle for venting. For this process, all washings between steps were done by first disassembling the reaction chamber and then rinsing each slide individually with the given solvent. Excess solvent was removed from the surface by means of a nitrogen gas stream. A fresh gasket was used for each subsequent chamber assembly and derivatization process.

Derivatized glass surfaces were patterned as follows: DMT-hexa-ethyloxy-glycol-CED phosphoramidite (DMT-HEG-CEP) was coupled to surface bound amines using a 1:1 solution of 0.1M linker and 0.45 M 5-ethylthiotetrazole in acetonitrile for 15 minutes with mixing. After two acetonitrile washes the chips were treated with a 0.1 M solution of iodine in tetrahydrofuran (THF)/pyridine/water for 1 minute and then washed twice with acetonitrile. Any uncoupled amines were acylated by treatment with a 25% v/v solution of acetic anhydride in pyridine for 15 minutes. Following DMT removal via treatment of the surfaces with a 3% w/v solution of trichloroacetic acid (TCA) in dichloromethane (DCM), compound 8 was coupled in some of the derivatized sites to the surface-bound terminal hydroxyls using standard phosphoramidite chemistry. In other derivatized sites, dT-CE phosphoramidite was coupled to serve as non-photolyzable controls. In every hydrophilic site, the following polynucleotide was prepared using standard phosphoramidite chemistry: 3'-GCA TGC ATG CAT GCA-5' (SEQ. ID. No. 2). Then, Cy3-phosphoramidite (Glen Research, Sterling, Va.) was coupled to every other derivatized site to provide a detectable, fluorescent end-label. The substrate-bound polynucleotides were then deprotected using a 1:1 v/v solution of ethylenediamine in ethanol.

Figure 10:
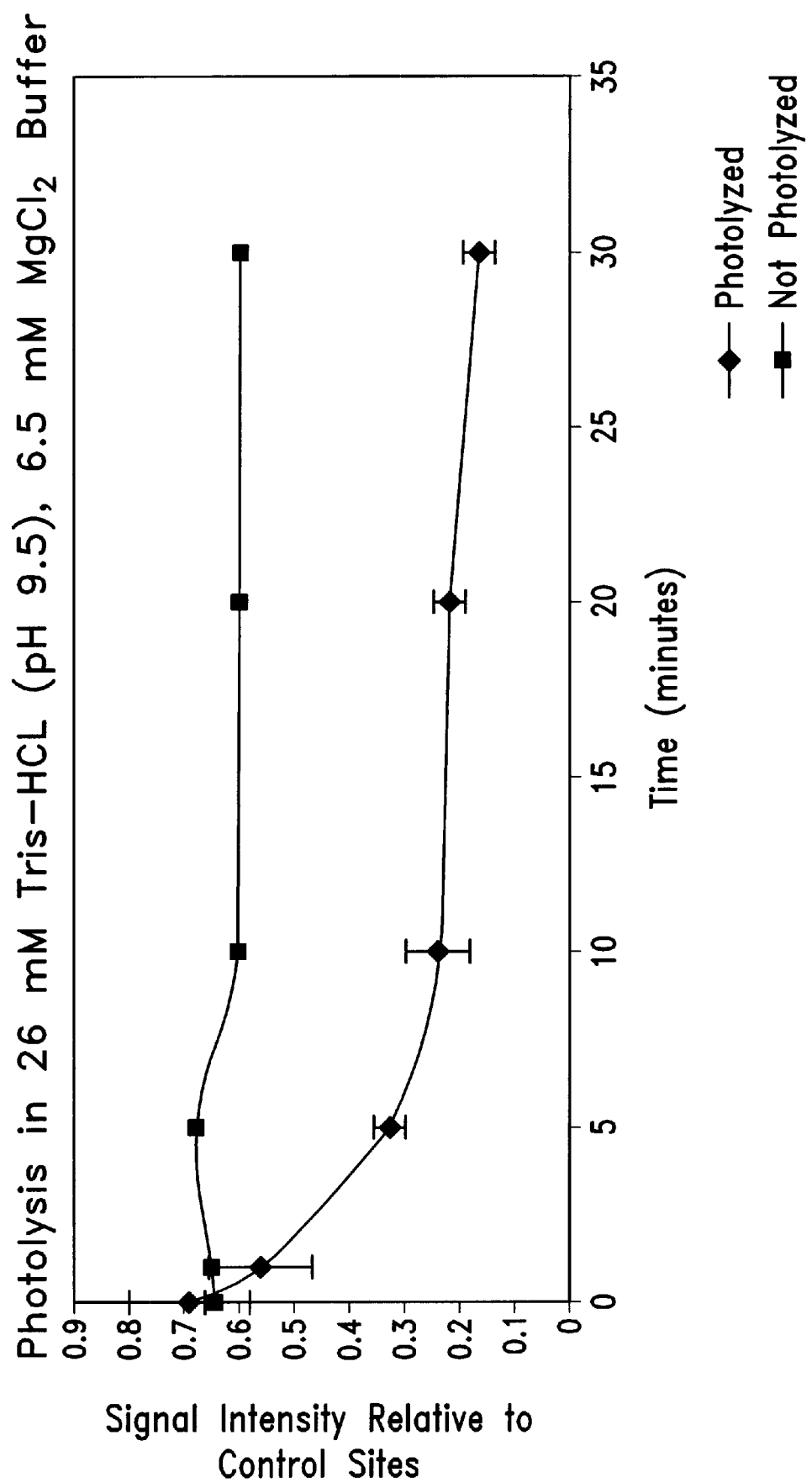
FIG. 10 illustrates photolysis of in situ synthesized photocleavable polynucleotides.

After dicing the substrate into 1"×2" chips, a chamber assembly was made for the photolysis studies. Briefly, two chips (one derivatized, one blank) were placed with the patterned surface facing inwards and separated by a silicone rubber gasket. The gasket and chips were secured by four steel binder clips. Buffer (26 mM Tris-HCl, pH 9.5, 6.5 mM $MgCl_2$) was introduced via syringe through a 27-gauge needle. The gas interior was displaced through an open needle while reagent was being injected with the syringe. Photolysis was performed using a high-pressure mercury lamp with a light intensity of 16.0 mW/cm$^2$ centered at 365 nm. At the end of the given process, the buffer was removed via syringe. The chamber was disassembled and the chip was washed with acetonitrile, ethanol, then water and the fluorescence detected using an Axon GenePix 4000 scanner. As shown in FIG. 10, the fluorescent signal in the photolabile sites decreases over time relative to the non-photolyzable sites. At or about 10 minutes, the signal decrease levels out and does not significantly lower over the next 120 minutes. This experiment shows that compound 8 couples to the surface through a linker and is a viable substrate for subsequent polynucleotide synthesis.

EXAMPLE 5

Photolytic Release of Polynucleotides from the Surface and Subsequent Hybridization of the Released Polynucleotides This experiment was designed to address the issue of photolytic release of in situ synthesized polynucleotides from the array surfaces and study their subsequent hybridization to complimentary, surface-bound polynucleotides. This study was designed to address the issue of photolysis and subsequent motility and hybridization of the released polynucleotides from a linker derivatized with amidite 8.

Figure 11:
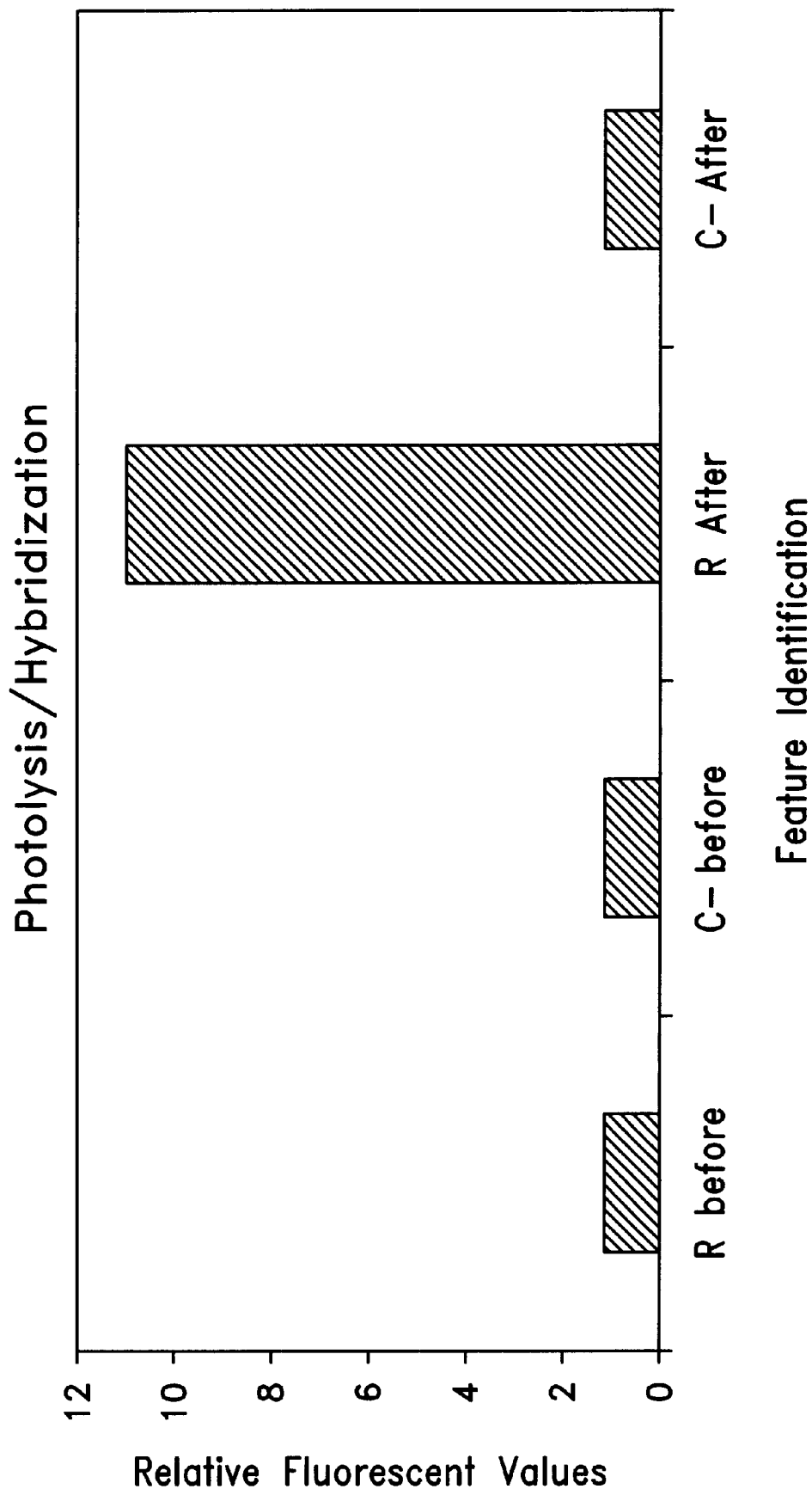
FIG. 11 illustrates photolytic release of polynucleotides from the surface and subsequent hybridization of the released polynucleotides.

A patterned, surface-tension array was prepared with 5×5 derivatized sites as depicted below (25 derivatized sites per unit cell, 10 total unit cells/chip). In the sites containing the "F" sequence, amidite 8 had been coupled. All other sites had a noncleavable amidite (dT-CEP, Glen Research, Sterling, Va.) coupled to the site. The synthesis was performed in a 3'-to-5' directions using commercially available reagents and house made robotics. The "F" polynucleotides were then end-labeled with Cy 3-Phosphoramidite (Glen Research, Sterling, Va.). Following deprotection of the polynucleotide backbone and heterocycles, the chip was scanned on an Axon GenePix4000. After the initial scan, the arrayed chips were assembled in a sandwich-like format with a microfabricated coverslip containing 10 wells (5×5×0.1 mm) that line up over the 10 unit cells of in situ synthesized polynucleotides. Each microfabricated well contained, nominally, 2.5 μL of 260 mM Tris-HCl, pH 9.5, 65 mM $MgCl_2$, 20 mM KCl, 0.1% Triton X-100. The coverslip and polynucleotide immobilized chip were conjoined by use of 100 μL of a synthetic polymer (2×Self-Seal, MJ Research, Watertown, Mass.) deposited on the perimeter of the assembly. At this time, the assembly was exposed to ~200 J of 365 nm light. Following chamber disassembly and washing, the chip was scanned again and the signal intensities recorded and charted in FIG. 11. As can be seen, polynucleotides were released from the intended sites and did form a duplex with its compliment in the designated sites ("R" polynucleotides). The signal in the noncleavable sites increased 10 fold over the pre-photolysis numbers. The "C-" blank control was not hybridized to, as expected. It should be noted that the absolute fluorescence values were normalized to give a comparative representation.

This experiment was also performed under the following conditions. Using the same substrates, the array surface was exposed to 365 nm light (measuring at 16.0 mW/cm$^2$) for 15 minutes. Then, 30 μL of SSC buffer, pH 8.2, 50 mM sodium bicarbonate, 0.8% Tween-20, was floated over the surface with the use of a microscope cover slip (Fisher Scientific). After 30 minutes, the coverslip was removed, the array washed with briefly with 150 mM aqueous sodium bicarbonate solution, dried under a stream of argon, and scanned on an Axon GenePix4000. The results mirrored those described above with the exception that the hybridization signal increased 30 fold over the pre-photolysis numbers.

| A 5 x 5 unit cell | | | | |
|---|---|---|---|---|
| F | F | F | F | F |
| F | R | F | R | F |
| F | F | C- | F | F |
| F | R | F | R | F |
| F | F | F | F | F |

| Abbreviations | |
|---|---|
| Probe | 3'-5' Sequence (SEQ. ID. Nos: 3–5) |
| F | TTTTATCGGAGATTCGGGTTGAG |
| R | ctcaacccgaatctccgataaaa |
| C- | GATGCTACCGTGACTGACTGACTGACTGA |

EXAMPLE 6
In situ Synthesis of Probes for Sequence Variation or Gene Expression Detections Drop-on-demand polynucleotide synthesis was performed on a DNA microarray synthesizer using the following -reagents (all reagents were purchased from Glen Research, Sterling, Va., unless noted): phosphoramidites: pac-dA-CE phosphoramidite, Ac-dC-CE phosphoramidite, iPr-pac-dG-CE phosphoramidite, dT CE phosphoramidite (0.1M); activator: 5-ethylthio tetrazole (0.45M). Amidites and activator solutions were premixed, 1:1 :v/v, in a 90% adiponitrile (Aldrich): 10% acetonitrile solution prior to synthesis. The following ancillary reagents were used: Oxidizer (0.1M iodine in THF/pyridine/water), Cap mix A (THF/2,6-lutidine/acetic anhydride), Cap mix B (10% 1-methylimidazole/THF), and 3% TCA in DCM. Parallel synthesis of individual polynucleotides was achieved by the addition of individual amidites to the hydrophillic regions of prepared surface tension arrays via custom designed piezo electric ink-jet devices (Microfab Technologies, Plano, Tex.). The jets were run at 6.67 kHz using a two step wave form which fired individual droplets of approximately 50 picoliters per drop.

For the 1 mm diameter features approximately 400 drops were added to each feature per nucleotide addition. After a suitable coupling time, the uncoupled amidites were washed off of the surface by flooding with acetonitrile then removed by spinning the chip at 2000 rpm for several seconds. All other reagents were added to the surface by flooding the substrate and removed after suitable reaction times. The synthesis was done in a closed nitrogen saturated environment with a unidirectional flow of protecting gas. The synthesis cycle is summarized in Table 1.

TABLE 1

Synthesis cycle for the production of a surface tension polynucleotide microarray.

| Step in Cycle | Volume (mls) | Time (seconds) |
|---|---|---|
| ACN Wash | 4.2 | 5 |
| $^1$Spin | | 5 |
| ACN Wash | 4.2 | 5 |
| Spin | | 5 |
| Deblock (3% TCA in DCM) | 3.5 | 15 |
| Spin | | 5 |
| Deblock (3% TCA in DCM) | 3.5 | 15 |
| Spin | | 5 |
| ACN Wash | 4.2 | 5 |
| Spin | | 5 |
| $^2$Dry down | | 10 |
| Couple Amidites | 2 × 10$^{-6}$ | 120 |
| ACN Wash | 4.2 | 5 |
| Spin | | 5 |
| Cap (CapA:CapB, 1:1) | 4.5 | 15 |
| Spin | | 5 |
| Oxidize | 5.5 | 15 |
| Spin | | 5 |
| Cap (CapA:CapB, 1:1) | 4.5 | 10 |
| Spin | | 5 |
| Repeat cycle until the desired probes are produced | | |

$^1$Spin speed between successive washing steps was 2000 rpm. Washing and coupling steps were done at different locations on the chip synthesizer where there was a continuous unidirectional flow of nitrogen that was directed from the synthesis location towards the washing position. This kept the ancillary reagent vapors from interacting with the amidites.
$^2$A dry down was a step that was included prior to coupling to evaporate any residual ACN that may have been left on the hydrophilic regions of the array. This consisted of a high pressure nitrogen purge over the surface of the substrate.

EXAMPLE 7
Microfabrication of Wells on Arrays (coverslips)

Figure 12:
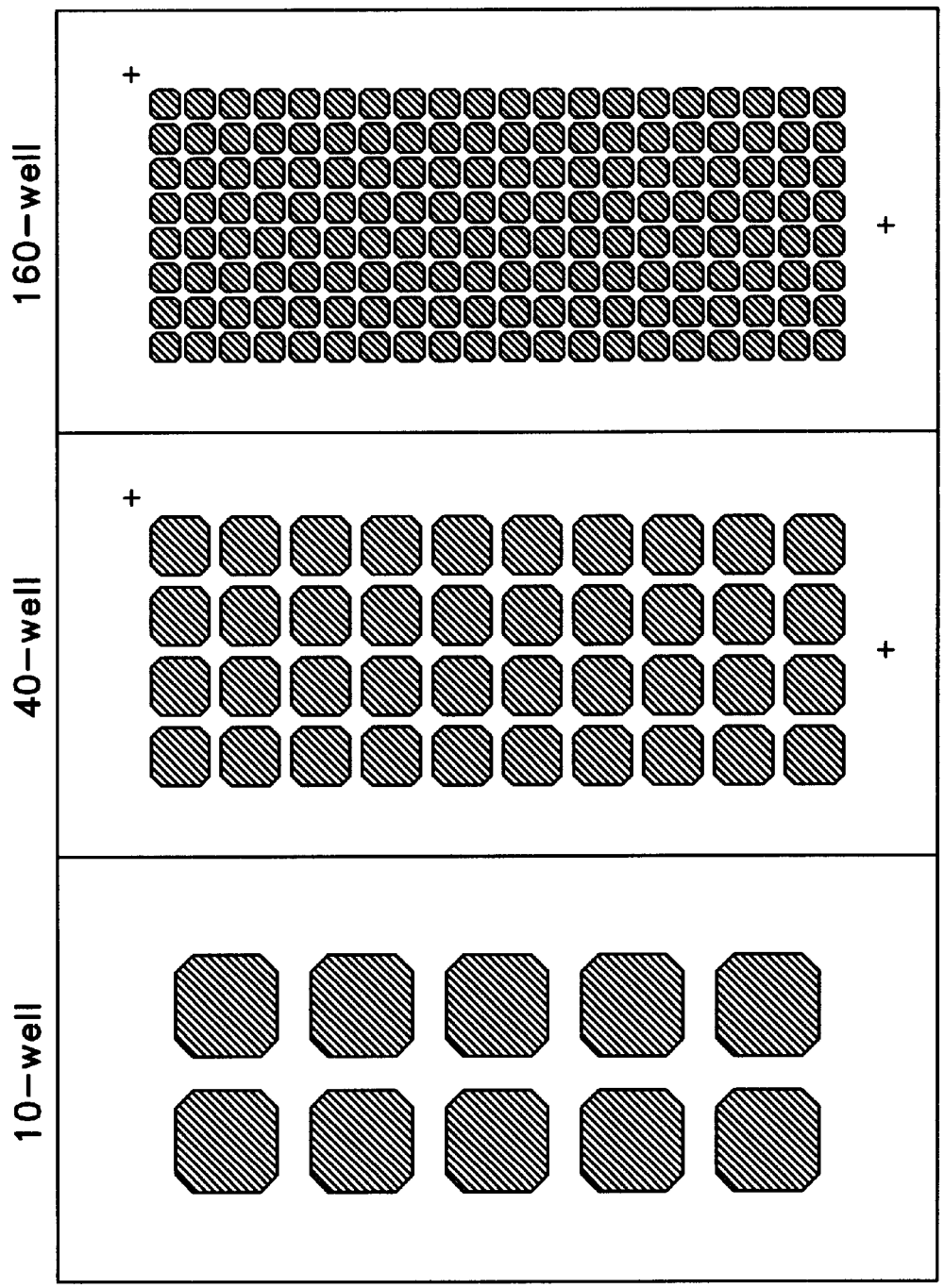
FIG. 12 illustrates several designs of an array micrfabricated with wells.

Borofloat glass rounds (100 mm diameter and 0.7 mm thick) were used to prepare the coverslips. Several coverslip designs were made according to FIG. 12 and according to the following procedure:

Glass Cleaning and Patterning

A pre-cleaning step was performed by soaking the wafers in peroxysulfuric acid followed by a rinse and drying. The wafers were dipped in 49% hydrofluoric acid for about 15 seconds to roughen and clean the surface followed by rinsing and drying. The wafers were coated with a thin layer of amorphous silicon by chemical vapor deposition in a Tylan type oven at 525° C. at a thickness of 1500Å. To remove any moisture, the wafers were singe baked in an oven for about 30 minutes at 150° C. The wafers were primed with a layer of HMDS (hexamethyldisilazane) at 6000 RPM for 20 seconds before photo resist application. A viscous photo resist (Shipley SPR220-7) was used to coat the wafers and are spun at 3500 RPM for 30 seconds to a thickness of 7 um. The photo resist layer was pre-baked for about 200 seconds on a hot plate at 90° C. The wafers were then allowed to stand for about 3 hours prior to exposure. A UV aligner with a wavelength set at 350 nm with an exposing time of about 12 seconds was used for each wafer.

Due to the thickness of the photo resist, the wafers were allowed to stand for about 3 hours before developing. This helps improve critical line resolution of the exposed areas. The wafers were then dipped in developer solution (Shipley LDD26W) at least 3 times for about two minutes each time with a deIonized water rinse after developing. A post-bake step wasperforned at 90° C. for one hour in an oven.

Glass Etching

The etching steps involve the pattern etching by removing the amorphous silicon layer and the actual glass etching. The pattern etching was accomplished by using a plasma etcher that uses sulfur hexafluoride and Freon 115 at a rate of 5.2 and 0.5 cm$^3$/s respectively. An etching time of 2 minutes was sufficient to remove the amorphous silicon. The wafers were etched in 49% hydrofluoric acid for an initial time of 8 minutes. A water rinse and spin dry step followed and the wafers were placed back into the 49% hydrofluoric acid solution for the remaining time required to reach a final depth of 100 microns. The wafers were rinsed and dried. The photo resist was removed using acetone and the remaining amorphous silicon was removed with heated potassium hydroxide at about 70° C. The wafers were then rinsed and dried. To remove the potassium on the glass surface, the wafers were treated with about a 20% solution of hydrochloric acid. A final peroxysulfuric acid treatment was performed to remove any residuals. The wafers were diced to a 1"×2" sized coverslips.

Chemical Derivatization of the Coverslips

A multiple cleaning process was performed prior to the aminosilation and acetylation of the coverslips. The coverslips were sonicated for about 10 minutes and water rinsed to remove any dust or glass particulates from the dicing process. To remove any dirt or oils on the glass surfaces, the coverslips were soaked with 10% weight to volume sodium hydroxide at 70° C. for 30 minutes. The coverslips were water rinsed and soaked in peroxysulfuric acid treatment for about an hour. To free the Si-O groups on the glass surface, the coverslips were placed in a plasma etcher with oxygen as the gas for 15 minutes at 70° C. The coverslips were placed in a reaction kettle and 1 ml of 3-aminopropyldimethylethoxy silane was added. The kettle was placed in an oven at 55° C. and left overnight to complete the gas phase reaction. The coverslips were removed from the kettle and were placed in an oven at 90° C. for an hour to cure the surface. The coverslips were sonicated in a 1:1 mixture of acetonitrile and ethanol for about 15 minutes to remove any un-reacted reagent.

To complete the acetylation, the coverslips were reacted with 25% (by volume) acetic anhydride with pyridine as the solvent. The coverslips were allowed to stand for at least two hours for the reaction to complete. The coverslips were sonicated with a 1:1 solution of acetonitrile and ethanol to remove any un-reacted acetic anhydride for about 15 minutes. The coverslips were dried with nitrogen and were ready for use in the array assembly.

EXAMPLE 8

Polymorohisms, Alleles, and Phenotypes of the NAT2 Gene

N-acetyltransferase 2 (NAT2) is a polymorphic N-acetylation enzyme that detoxifies hydrazine and arylamine drugs and is expressed in the liver. The NAT2 coding region spans 872 base pairs (Genbank Accession No. NM-000015). The PCR product is approximately 1276 base pairs.

Polymorphisms in the NAT2 gene cause the fast and slow N-acetylation phenotypes implicated in the action and toxicity of amine containing drugs. In addition, NAT2 acetylation phenotype is associated with susceptibility to colorectal and bladder cancers. Table 1 summarizes the seven common single nucleotide polymorphisms (SNPs) found in this gene (G191A, C282T, T341C, C481T, G590A, A803G, and G857A) and defines the nine most common alleles (*4 being the wild type allele) along with their associated phenotypes and population frequencies. See Grant et al., *Mutat. Res.* 376:61–70 (1997) and Spielberg et al., *J. Pharmacokint. Biopharm.* 24:509–519 (1996). Each of the seven polymorphisms is a marker for more than one NAT2 allele and each variant allele is defined by two or three SNP substitutions. NAT2 provides a clearly defined, low complexity model system for developing a hybridization based genotyping assay. Typically, homozygous or heterozygous genotypes are made at each polymorphic site before probable allele assignments can be made. In general, individuals who are homozygous for any combination of the slow acetylator alleles are slow acetylators, where rapid acetylators are homozygous or heterozygous for wild-type NAT2 allele. It has been suggested that slow acetylators may be at increased risk for developing bladder, larynx and hepatocellular carcinomas, whereas rapid acetylator may be at risk to develop colorectal cancer. The frequency of the slow acetylator phenotype varies among ethnic groups and is roughly 50%–60% in Caucasian populations. See Grant, D., et al, *Mutation Research* 376:61–70 (1997) and Lin, H., et al, *Pharmacogenetics* 4:125–134 (1994). Polynucleotide array can be used to determine whether a target nucleic acid sequence has one or more nucleotides identical to or different from a specific reference sequence.

TABLE 2

Polymorphisms, alleles, and phenotypes of the NAT2 gene

| allele | Polymor. | | | | | | | Phenotype | Frequency |
| --- | --- | --- | --- | --- | --- | --- | --- | --- | --- |
| | G191A | C282T | T341C | C481T | G590A | A803G | G857A | | |
| *4 | G | C | T | C | G | A | G | Rapid | 23.40 |
| *5A | G | C | C | T | G | A | G | Slow | 2.50 |
| *5B | G | C | C | T | G | G | G | Slow | 40.90 |
| *5C | G | C | C | C | G | G | G | Slow | 2.60 |
| *6A | G | T | T | C | A | A | G | Slow | 28.40 |
| *7B | G | T | T | C | G | A | A | Slow | 2.10 |
| *12A | G | C | T | C | G | G | G | Rapid | 0.10 |
| *14A | A | C | T | C | G | A | G | Slow | rare |
| *14B | A | T | T | C | G | A | G | Slow | 0.10 |
| Amino Acid Change | R → Q | None | I → T | None | R → Q | K → R | G → E | | |

EXAMPLE 9
Performing, Large Numbers of PCR Reactions Using Array-immobilized and Releaseable Primers and Detecting Amplified Product by Hybridization In the current Example, G 191A polymorphic site of the NAT2 gene was determined using array assembly. A first array with 535 individual derivatized areas (500 um diameter, 1000 um spacing) were prepared on a chip according to previous Examples. Primers and probes are designed and organized as described in FIG. 13 (SEQ. ID. Nos. 6–13). The complementary sequences to the primers are immobilized in the primer sites F and R, to capture respectively Reverse and Forward primers during a pre-hybridization step. Polynucleotide synthesis was carried out in the direction 3' to 5' (3' attached to the surface of the glass) according to known procedures.

A second array was microfabricated according to Example 7 (coverslip). A coverslip contains 10 unit cells (5 mm×5 mm ×100 um depth). Each cell was designed to face 25 derivatized sites on the first array upon juxtaposition of the two arrays.

Pre-hybridization of the Primers

The first array was hybridized in 30 ml of (2×SSC, 0.1% Tween20, and 50 mM $NaHCO_3$) with 2.5 nm of Cyanine 3 Labeled primers at RT for 30 minutes, then washed in 30 mls of 150 mM $NaHCO_3$ at RT for 15 minutes shaking slowly. The first array was then dipped briefly in 70% Ethanol/$H_2O$ and air dried for 10–15 minutes and scanned.

Figure 14A:
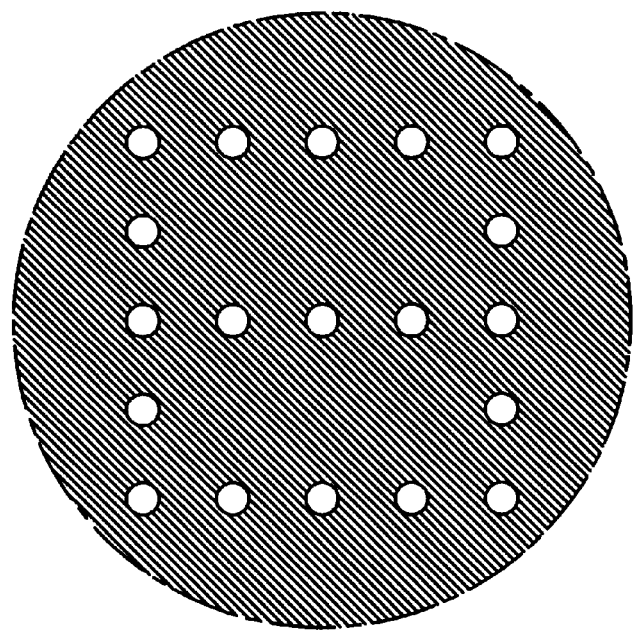
FIG. 14 illustrates a result of primer release from a hybridization complex.
Figure 14:
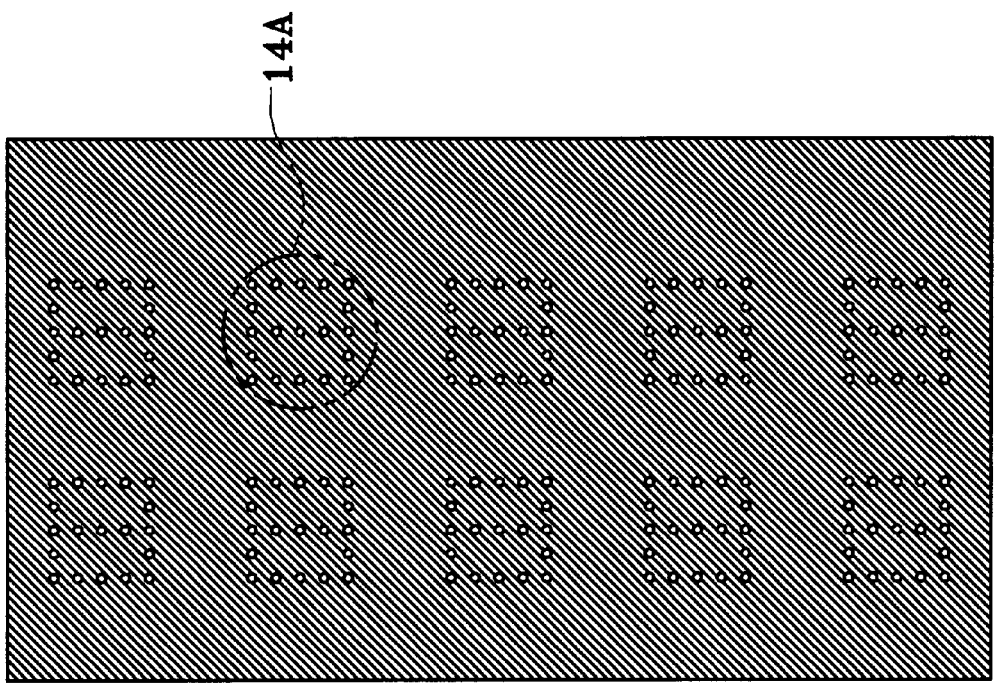

The scanner generated picture on FIG. 14 shows the locations where the labeled primers have accumulated (bright round spots). The high intensity areas correspond exactly to the sites on the surface of the array where the complementary sequences of the primers were synthesized (see FIG. 13). The maximum intensity obtained for this hybridization corresponds to approximatively 30 fmoles of primer hybridized per square millimeter. The level of fluorescence detectable for the other synthesis sites was negligible.

Preparation of Array Assembly

A liquid polymer (100 ul of 2× Self-Seal, MJR) was deposited on the perimeter of the first chip and allowed to dry. Upon assembly and rehydration the liquid polymer created an efficient leakproof gasket that prevented excessive evaporation during the temperature cycling Array Assembly The PCR mix (200 ul, 26mM Tris-HCl, pH 9.5, 6.5 mM $MgCl_2$, 0.1% TritonX-100, 20 mM KCl, 200 mM dNTP's, 0.5 U.ul Thermosequenas,) containing 0.1 ng/ul of DNA target (genomic DNA) was used.

The top edge of the first array was put in contact with the second array (coverslip) with a 45 to 60 degrees angle. The PCR mix was loaded in the space created between the first array and the coverslip. The first array was then gradually lowered against the coverslip in a motion that prevents air from being trapped inside the assembly (FIG. 15).

Temperature Cycling

The assembly was introduced into a commercially available in-situ PCR instrument (MJResearch) and the following temperature program was started: 2 min 86° C.; 0.5 min 86° C. ;1.0 min 56.5° C.: 30 times then 5 min 72° C., total cycle time is 1.3 H.

After the last cycle, the assembly is heated to 92° C. for 2 minutes followed by a 25° C. step for 30 min to allow denaturation and hybridization of the PCR product to the probes on the first array.

The assembly was then opened, and the first array was washed with 30 ml of Phosphate Buffer (100 mM NaCl, 3 mM KCl, 4 mM $Na_2HPO_4$, 1.5 mM $NaH_2PO_4$, 0.5% Tween20, pH=7.2) for 15 minutes at RT. The first array was then dipped briefly in 70% Ethanol/$H_2O$ and air dried for 10–15 minutes and scanned (FIG. 16).

Figure 16:
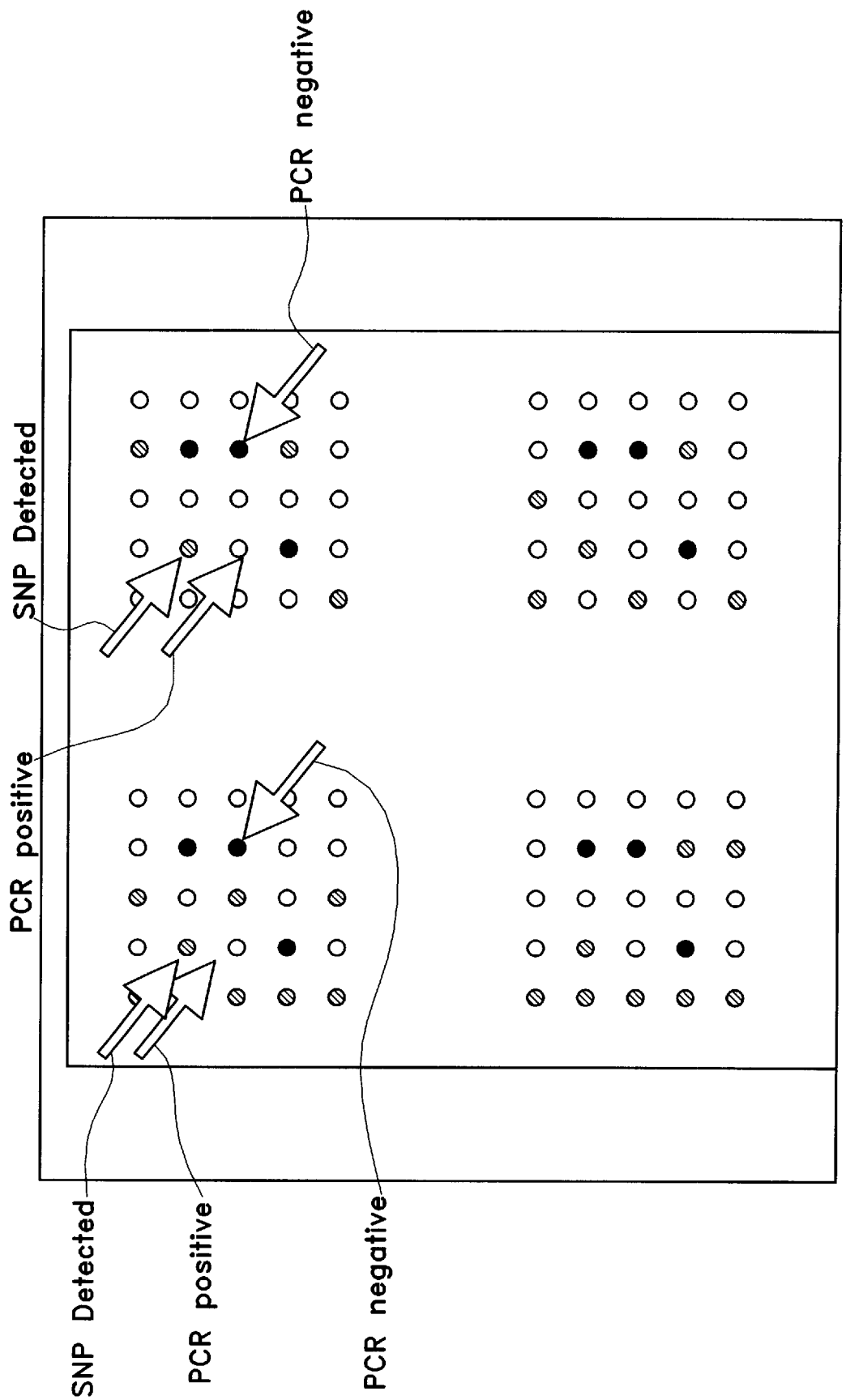
FIG. 16 illustrates the result of coupling polynucleotide amplification reactions with detections by hybridization using array assembly.

FIG. 16 is an image of the top four PCR wells of the first array after PCR cycling, hybridization and wash. As before, the primers sites showed very high (gray) or saturating intensities (white). The positive control probe for PCR (PCR positive arrow) showed very high or saturating intensities while the negative control probes (PCR negative arrow) remained close to noise intensity (black). This result demonstrates that a PCR product was specifically generated inside the array assembly.

The Coding Probe 1-A (SNP Detected arrow) had higher intensity than the Coding Probe 2-G (refer to FIG. 13 for exact location). This result agrees with the DNA type (homozygote type 1-A) as determined by dideoxysequencing of the NAT2 PCR product.

EXAMPLE 10
Comparison of Primers Introduced by Hybridization Versus Introduction of the Primers in Solution Four array assemblies were created as described in Example 9 except for two assemblies where a 200 nM final concentration of the Cyanine 3 labeled primers was added to the PCR mix. The PCR cycle, washes and scans were performed as previously described and the results are summarized in the FIG. 17.

Figure 17:
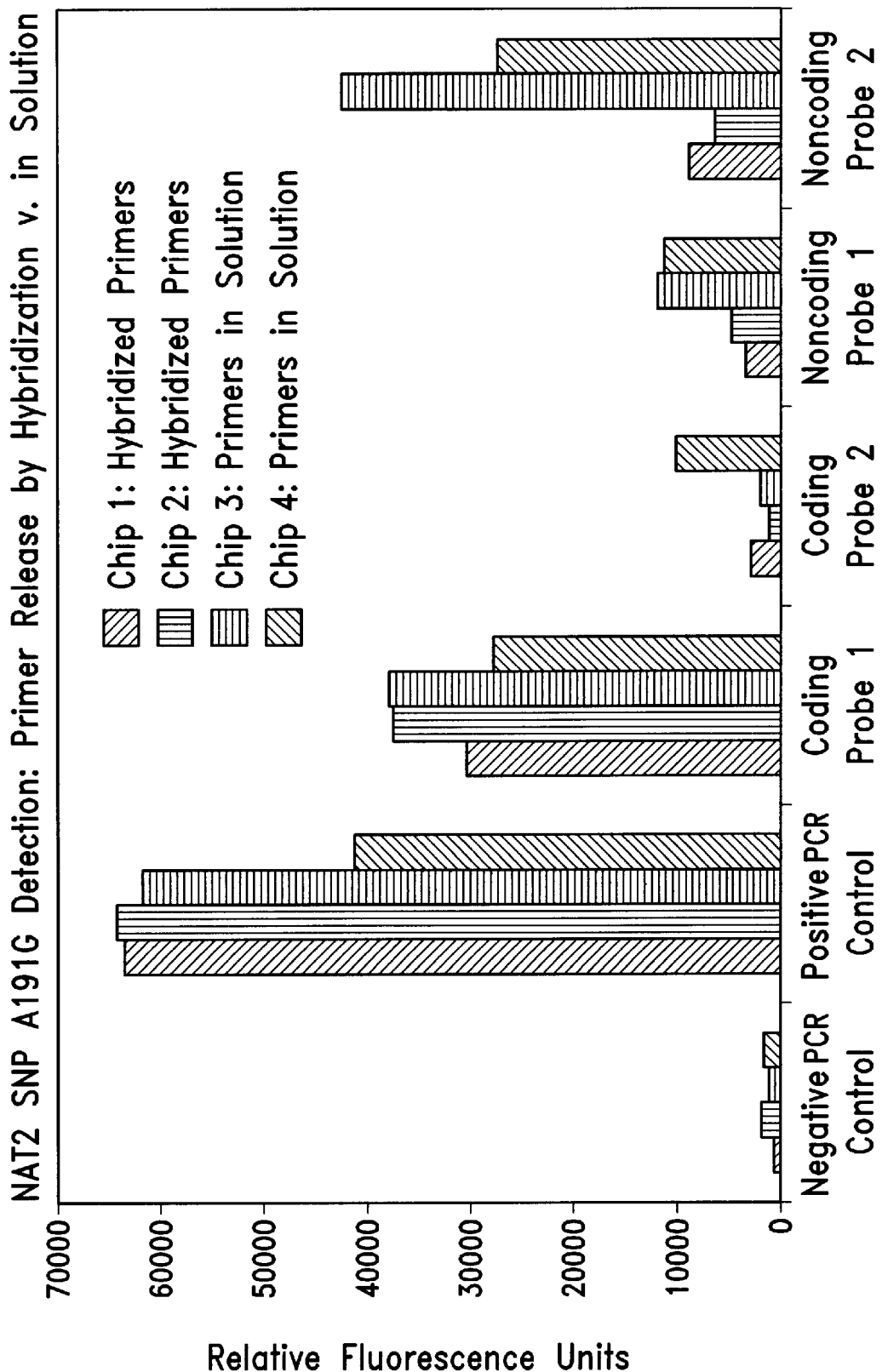
FIG. 17 illustrates a comparison between primer releases from hybridization complexes vs. primers in solution.

The bars in FIG. 17 represent the average intensities (expressed in Relative Fluorescence Units) collected from the scan for each feature of the polynucleotide-immobilized array.

The introduction of the primers by hybridization gives comparable results to the PCRs with primers added in solution suggesting that the efficiency of the formation of PCR product is similar.

EXAMPLE 11
Performing Large Numbers of PCR Reactions Using Array-immobilized and Releaseable Primers and Detecting Amplified Product by Allele Specific Extension A DNA microarray with 535 individual derivatized areas (500 um diameter, 1000 um spacing) were prepared according previous Examples. In situ polynucleotide synthesis was carried out in the direction 5' to 3' (5' attached to the surface of the glass) according to known procedures. In this manner the 3' end of the probe is free to be elongated by the DNA polymerase upon hybridization of the amplified products.

Figure 18:
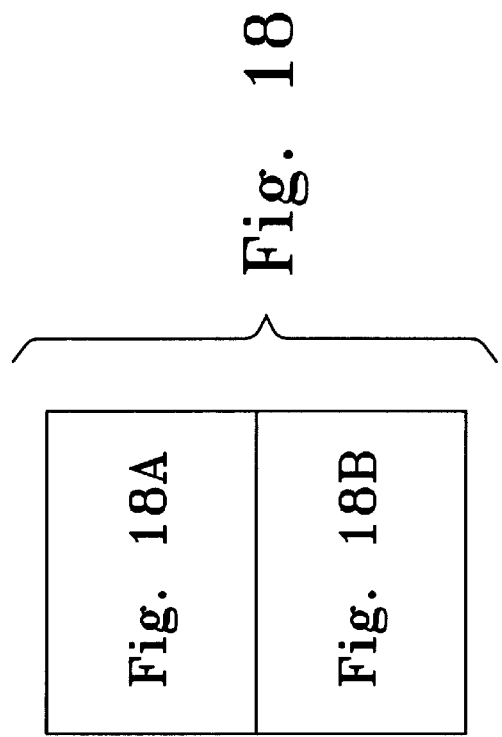
FIG. 18 illustrate a layout of two unit cells on a derivatized array for detection by a DNA modifying enzyme.
Figure 18A:
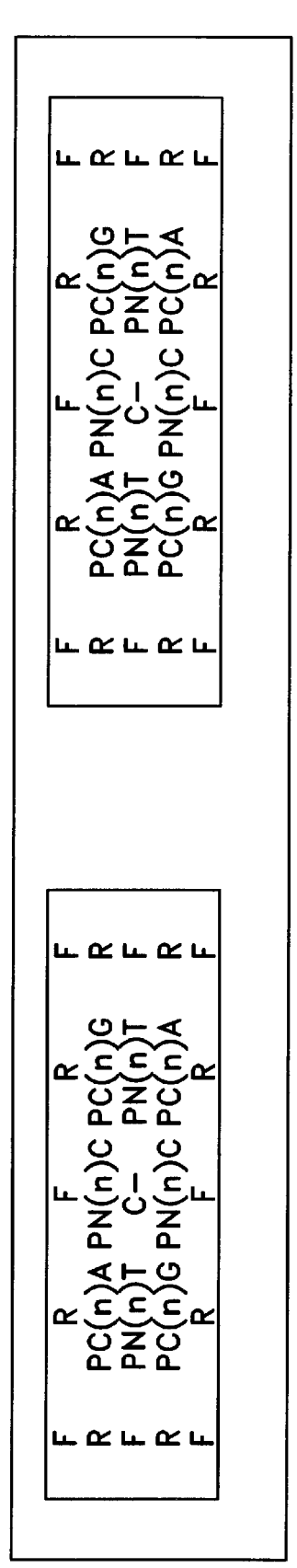

A second microfabricated array was prepared according to Example 7 that contains 10 unit cells (5 mm×5 mm×100 um depth). Each cell was designed to face 25 derivatized sites on the DNA microarray upon juxtaposition of the two arrays. Primers and probes were designed and organized as described in FIG. 18 (SEQ. ID. Nos. 14–32).

The preparation of the DNA microarray and application of the liquid polymer is done as described in Example 9.

Reaction Assembly

The PCR mix (200 ul, 26 mM Tris-HCl, pH 9.5, 6.5 mM $MgCl_2$, 0.1%TritonX-100, 20 mM KCl,200 mM dATP, 200 mM dGTP, 175 mM dCTP, 25 mM Cy3-dCTP, 175 mM dTTP, 25 mM Cy3-dUTP, 0.5 U.ul Thermosequenase, 200 nM of each primer) containing 0.1 ng/ul of DNA target (genomic DNA A191G type A homozygote) is used.

Temperature Cycling

The assembly is introduced into a commercially available in-situ PCR instrument (MJR) and the following temperature program is started: 2min 86° C.; 0.5 min 86° C. ;1.0 min 56.5° C.: 30 times then 5 min 72° C., total cycle time is 1.3 H After completion of the temperature program, the assembly was opened, and the DNA microarray was washed with a solution of triethylamine:ethanol 1:1 for 15 minutes at room temperature, rinsed 3 times with water, dried with nitrogen and scanned. The results are summarized in FIG. 19.

Figure 19:
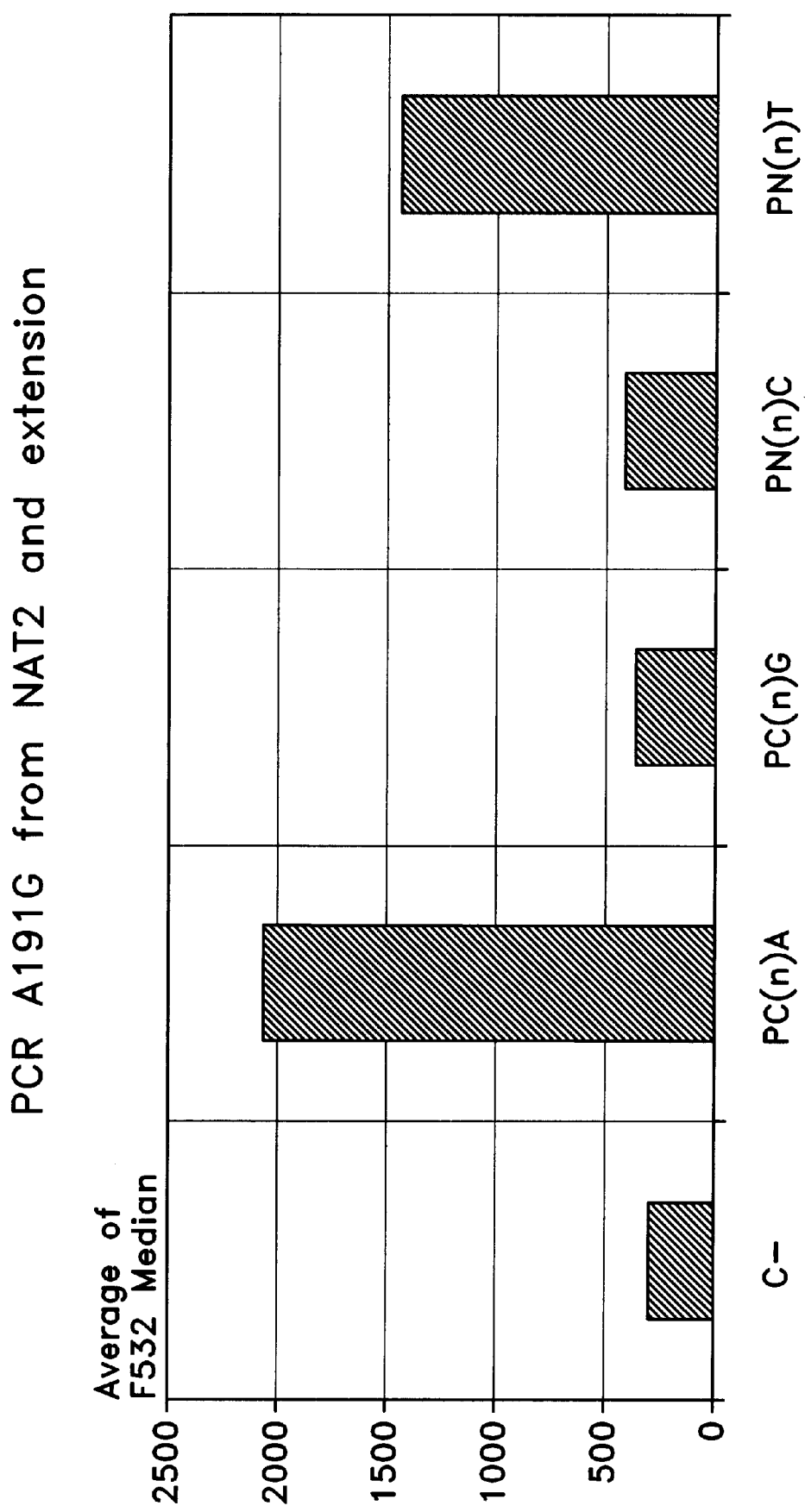
FIG. 19 illustrates the result of coupling polynucleotide amplification reactions with detections by allele specific extension using array assembly.

The bars in FIG. 19 represent the average intensities (expressed in Relative Fluorescence Units) collected from the scan for each feature of the DNA microarray.

The Negative Control (C-) intensity corresponds to the background level for this experiment and can be appropriately subtracted for more accurate results. The Probe Coding A (PC(n A) and Probe Non-Coding T (PN(n)T) have higher intensities than respectively the Probe Coding G (PC(n G) and Probe Non-Coding C (PN(n C) in accordance with the DNA type(homozygote type 1-A) as determined by dideoxy-sequencing of the NAT-2 PCR product.

This result shows that the PCR product can be efficiently detected and genotyped using simultaneous PCR, labeling and allele specific extension of the probes at the surface of an array.

EXAMPLE 12
Real-Time Quantitation of Amplification Product

The fluorescent dye SYBR Green I binds to the minor groove of the DNA double helix. In solution, the unbound dye exhibits very little fluorescence, however, fluorescence is greatly enhanced upon DNA-binding. Since SYBR Green I dye is very stable (only 6% of the activity is lost during 30 amplification cycles), it may be used to measure total DNA.

At the beginning of amplification, the reaction mixture contains the denatured DNA, the primers, and the dye. The unbound dye molecules weakly fluoresce, producing a minimal background fluorescence signal which is subtracted during computer analysis. After annealing of the primers, a few dye molecules can bind to the double strand. DNA binding results in a dramatic increase of the SYBR Green I molecules to emit light upon excitation.

During elongation, more and more dye molecules bind to the newly synthesized DNA. If the reaction is monitored continuously, an increase in fluorescence is viewed in real-time. Upon denaturation of the DNA for the next heating cycle, the dye molecules are released and the fluorescence signal falls.

Fluorescence measurement at the end of the elongation step of every PCR cycle is performed to monitor the increasing amount of amplified DNA. Together with a melting curve analysis performed subsequently to the PCR, the SYBR Green I format provides an excellent tool for specific product identification and quantification.

EXEMPLE 13
End-point Quantitation of PCR Product Using Array Assembly

A 10 well coverslip (5 mm×5 mm×100 um) was microfabricated as previously described. A "blank" DNA microarray (surface derivatized, but no DNA synthesis) was used as an inert counterpart for the array assembly.

Reaction Assembly

The PCR mix (200 ul, 26 mM Tris-HCl, pH 9.5, 6.5 mM $MgCl_2$, 0.1% TritonX-100, 20 mM KCl, 200 mM dATP, 200 mM dGTP, 200 mM dCTP, 200 mM dTTP, 0.5 U.ul Thermosequenase, 200 nM of each primer) containing 0.1 ng/ul of DNA target (or no DNA) and 1x Sybr Green was used to prepare the array assembly as described in Example 9.

Figure 20:
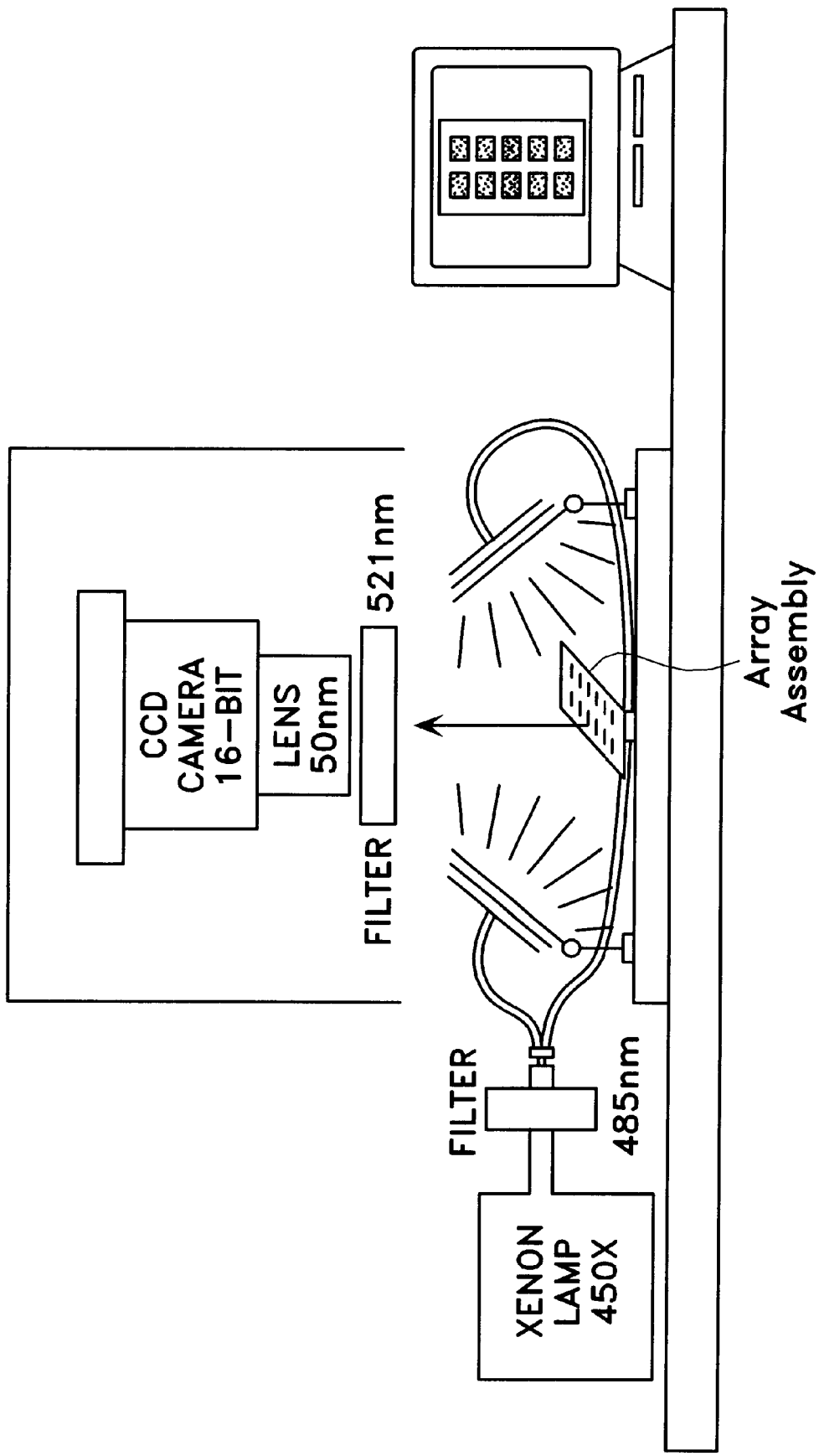
FIG. 20 illustrate end-point quantitation of PCR product using array assembly.

A picture was taken immediately following the assembly using an apparatus described in FIG. 20. The array assembly seats on the stage under the CCD Camera. The excitation was generated by a 450W Xenon lamp and filtered using a 485 nm +/−20 nm interference filter. The light was directed towards the surface of the assembly using two optical fibers with a linear shaped oulet to create an homogeneous epi-illumination of the array assembly. The intensity was approxymatively 1.5 uW/$cm^2$. The fluorescence was collected using a 16-bit, 1024×1024 pixels, back-illuminated CCD camera through a 521 nm +/−20 nm interference filter and a 50 mm×2.8 f lens. Acquisition time was set to 5 secondes, the image generated was displayed on a computer screen for further analysis.

Areas of interest were selected that matched the locations of the PCR wells and the intensities of the pixels comprising the area were averaged.

Temperature Cycling

Figure 21:
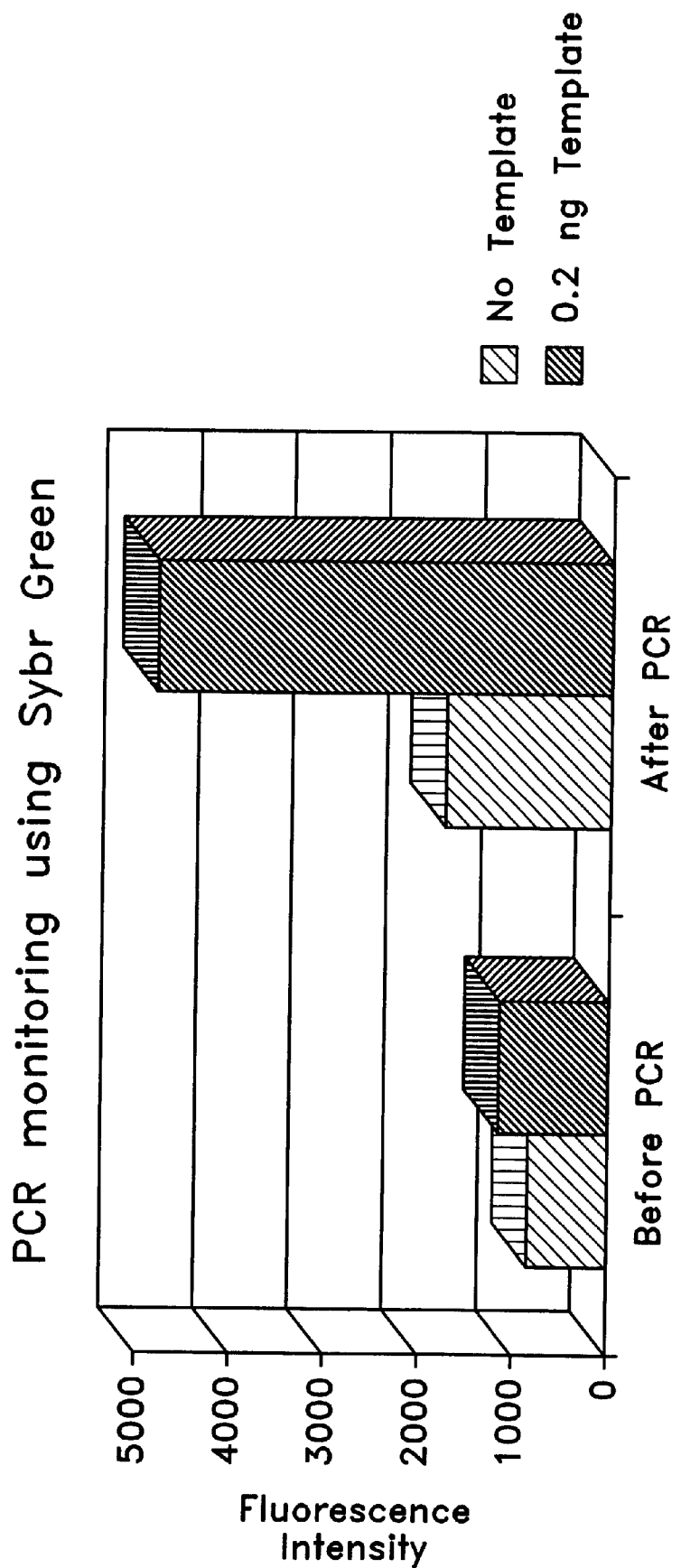
FIG. 21 illustrates polynucleotide quantitation using a fluorescent label.

The assembly is introduced into a commercially available in-situ PCR instrument (MJ Research) and the following temperature program was started: 2 min 86° C.; 0.5 min 86° C. ;1.0 min 56.5° C.: 30 times then 5 min 72° C., total cycle time is 1.3 H After the completion of the temperature program, the array assembly was imaged as described earlier. The images were analyzed and the results are summarized in FIG. 21.

The intensity of the fluorescence in the wells containing the template DNA after PCR was higher than before PCR and surpassed the intensity of the wells containing no template before or after PCR. This result shows that the formation of the double stranded PCR product can be monitored and quantitated during the PCR, simultaneously in all of the PCR wells. Accurate monitoring of the increasing amount of amplified DNA provides an excellent tool for gene expression analysis.

EXAMPLE 14
Allele Discrimination Using the 5' Nuclease Assay Using Array Assembly The 5' nuclease allele discrimination assay exploits the 5'–3' nuclease activity of DNA polymerases to allow direct detection of the PCR product by the release of a fluorescent reporter as a result of PCR. Two probes are used, one probe for each allele in a two-allele system. Each probe consists of a polynucleotide with a 5'-reporter dye and a 3'-quencher dye. TET (6-carboxy-4,7,2',7'-tetrachlorofluorescein) is attached to the 5' end of the probe for the detection of Allele 1. FAM (6-carboxyfluorescein) is attached to the 5' end of the probe for the detection of Allele 2. Each of the reporters is quenched by TAMRA (6-carboxy-N,N,N',N'-tetramethylrhodamine) attached via a linker arm located at the 3' end of each probe.

When the probe is intact, the proximity of the reporter dye to the quencher dye results in suppression of the reporter fluorescence. The probes hybridize to a target sequence within the PCR product. The DNA polymerase cleaves the probe with its 5'–3' nuclease activity. The reporter dye and quencher dye are separated upon cleavage, resulting in increased fluorescence of the reporter. Both primer and probe must hybridize to their targets for amplification and cleavage to occur.

The rate of cleavage of each of the allele specific probes depends directly on the rate of hybridization of the probes.

Detection of the alleles is done by measuring the increase of reporter fluorescence following PCR for each of the probes. The ratio of the intensities of fluorescence is used do determine the polymorphic type of the sample.

2400 individual hydrophilic areas (250 um diameter, 500 um spacing) are prepared on a first array and the solid phase synthesis of the DNA polynucleotides is carried out in the direction 5' to 3' (3' attached to the surface of the glass).

All the synthesis sites are first derivatized with the photocleavable linker to provide a mechanism for all primers and probes to be released into their PCR well A second microfabricated array is prepared according to previous Examples that contains 600 unit cells (1 mm×1 mm×100 um depth), each cell is designed to face four hydrophilic sites on the first array upon juxtaposition of the two arrays.

Primers and probes are designed and organized as described in Table 3.

TABLE 3

| Primer | Probe |
|---|---|
| Forward | Type 1 |
| Probe | Primer |
| Type 2 | Reverse |

While the primers are unmodified DNA sequences amplifying the DNA region comprising the SNP site, allele detection using 5' nuclease assays for real time quantitative PCR requires the two probes to be labeled with distinctly different reporter dyes at the 5' end and a quencher dye at the 3' end of the sequence. The reporter dyes are TET and 6-FAM and the quencher is TAMRA for the 5' and 3' labeling of the sequence. The TET, 6-FAM and TAMRA dyes are commercially available in their phosphoramidite form and are therefore conveniently directly coupled to the growing polynucleotides during in situ synthesis.

Preparation of the DNA Microarray for Assembly

After deprotection of the microarray 100 ul of liquid polymer (2× Self-Seal, MJR) is deposited on the perimeter of the DNA chip and allowed to dry. Upon assembly and rehydratation the liquid polymer will create an efficient leakproof gasket that prevents excessive evaporation during the temperature cycling Reaction Assembly 200 ul of the PCR mix (26 mM Tris-HCl, pH 9.5, 6.5 mM $MgCl_2$, 0.1%TritonX-100, 20 mM KCl, 200 mM dNTP's, 0.5 U Thermosequenase) containing 0.1 ng/ul of DNA target (genomic DNA) is used to prepare the array PCR assembly. The top edge of the microarray is put in contact with the coverslip with a 45 to 60 degrees angle. The PCR mix is loaded in the space created between the DNA microarray and the coverslip. The DNA chip is then gradually lowered against the coverslip in a motion that prevent air from being trapped inside the assembly.

Cleavage of the Primers and Probes

The assembly is exposed to 365 nm light, measured at 16 mW/cm2, for 15 minutes.

Temperature Cycling

The assembly is introduced into a commercially available in-situ PCR instrument (MJR) and the following temperature program is started: 2 min 86 C.; 0.5 min 86 C. ; 1.0 min 56.5 C.: 30 times then 5 min 72 C., total cycle time is 1.3 H.

After the last cycle, the assembly is heated to 92 C. for 2 minutes followed by a 45 C. step for 30 min to allow denaturation and hybridization of the PCR product to the probes on the DNA microarray.

After the completion of the temperature program, the assembly is imaged with the apparatus described in previous examples. Two images are taken and analyzed for each assembly using sets of filters compatible with TET and FAM spectral properties. The pictures are analyzed and the intensity ratios of the light emitted by each of the dyes are used to determine the allele of the sample for each of the studied SNPs.

The above description is illustrative and not restrictive. Many variations of the invention will become apparent to those of skill in the art upon review of this disclosure. These variations may be applied without departing from the scope of the invention. The scope of the invention should, therefore, be determined not with reference to the above description, but instead should be determined with reference to the appended claims along with their full scope of equivalents.

All publications, patents or web sites are herein incorporated by reference in their entirety to the same extent as if each individual publication patent or web site was specifically and individually indicated to be incorporated by reference in its entirety

We claim:

1. A method for performing a plurality of enzymatic amplification reactions, comprising the steps of:
   (a) obtaining a first solid support wherein at least two releasable primers of each reaction are confined to areas on the surface of said first solid support;
   (b) obtaining a second solid support with a plurality of wells providing separation of said plurality of reactions;
   (c) assembling said first and second solid support;
   (d) filling said wells with reactants of said reactions;
   (e) releasing said releasable polynucleotides into solution in each well; and
   (f) performing said plurality of amplification reactions in parallel.

2. The method according to claim 1 wherein said reactants in step (d) comprise a DNA polymerase, a target nucleic acid, and deoxynucleotides.

3. A method for performing a plurality of polynucleotide amplification reactions, comprising the steps of:
   (a) obtaining first solid support wherein a plurality of immobilized moieties are confined to a plurality of areas on the surface of said first solid support and each said immobilized moiety contains a releasable site and a primer;
   (b) obtaining a second solid support wherein the surface of said second solid support contains a plurality of areas and reactants of said polynucleotide amplification reactions are confined on each area of said second solid support;

(c) assembling said first and second solid supports, wherein said reactants of said polynucleotide amplification reactions on said second solid support are in contact with said immobilized moieties on said first solid support; and (d) releasing said primers;

(e) performing said plurality of polynucleotide amplification reactions.

4. A method for performing a plurality of polynucleotide amplification reactions and capturing amplification products, comprising the steps of:

(a) obtaining a first solid support wherein a plurality of immobilized moieties are confined to a plurality of areas on the surface of said first solid support and each said immobilized moiety contains a releasable site and a primer;

(b) obtaining a second solid support wherein the surface of said second solid support contains a plurality of areas and reactants of said polynucleotide amplification reactions are confined on each area of said second solid support;

(c) assembling said first and second solid supports, wherein said reactants of said polynucleotide amplification reactions on said second solid support are in contact with said immobilized moieties on said first solid support;

(d) releasing said primers;

(e) generating amplification products of said polynucleotide amplification reactions; and (f) capturing said amplified products by a plurality of immobilized polynucleotide probes on either said first or second solid support through hybridization.

5. A method for detecting a plurality of polynucleotide sequence variations, comprising the steps of:

(a) obtaining a first solid support wherein a plurality of immobilized moieties are confined to a plurality of areas on the surface of said first solid support and each said immobilized moiety contains a releasable site and a primer;

(b) obtaining a second solid support wherein the surface of said second solid support contains a plurality of areas and reactants of said polynucleotide amplification reactions are confined on each area of said second solid support;

(c) assembling said first and second solid support, wherein said reactants of said polynucleotide amplification reactions on said second solid support are in contact with said immobilized moieties on said first solid support;

(d) releasing said primers;

(e) generating amplification products of said polynucleotide amplification reactions;

(f) capturing said amplified products by a plurality of immobilized polynucleotide probes on either said first or second array through hybridization; and (g) detecting polynucleotide sequence variations by hybridization complexes in step (f).

6. A method for quantitating polynucleotides in a target nucleic acid, comprising the steps of:

(a) obtaining a first solid support wherein a plurality of immobilized moieties are confined to a plurality of finite areas on the surface of said first solid support and each said immobilized moiety contains a releasable site and a primer;

(b) obtaining a second solid support wherein the surface of said second solid support contains a plurality of areas and reactants of said polynucleotide amplification reactions are confined on each area of said second solid support;

(c) assembling said first and second solid support, wherein said reactants of said polynucleotide amplification reactions on said second solid support are in contact with said immobilized moieties on said first solid support;

(d) releasing said primers;

(e) generating amplification products of said polynucleotide amplification reactions; and (f) quantitating amplified products.

7. A method for detecting polynucleotide sequence variations in a target nucleic acid, comprising the steps of:

(a) obtaining a first solid support wherein a plurality of immobilized moieties are confined to a plurality of areas on the surface of said first solid support and each said immobilized moiety contains a releasable site and a primer;

(b) obtaining a second solid support wherein the surface of said second solid support contains a plurality of areas and reactants of said polynucleotide amplification reactions are confined on each areas of said second solid support;

(c) assembling said first and second solid supports, wherein said reactants of said polynucleotide amplification reactions on said second solid support are in contact with said immobilized moieties on said first solid support;

(d) releasing said primers;

(e) generating amplification products of said polynucleotide amplification reactions; and (f) capturing said amplified products by a plurality of immobilized polynucleotide probes on either first or second array though hybridization; and (g) detecting polynucleotide sequence variations by a polynucleotide modifying enzyme.

8. A method for amplifying a target nucleic acid, capturing the amplified product, and detecting a polynucleotide sequence variation in the amplified product, comprising the steps of:

(a) obtaining a first solid support wherein:

(1) the surface of said first solid support comprises a first, second, third, and fourth areas;

(2) a first chemical moiety, comprising a releasable forward primer for said target nucleic acid, is immobilized on said first area;

(3) a second chemical moiety, comprising a releasable reverse primer for said target nucleic acid, is immobilized on said second area;

(4) a first polynucleotide probe, comprising a subsequence complementary to one variant of said polynucleotide variation, is immobilized on said third area said subsequence containing at least one interrogation position complementary to a corresponding nucleotide in said variant; and (5) a second polynucleotide probe is immobilized to said fourth area, said second polynucleotide probe differing from said first polynucleotide probe by at least one nucleotide;

(b) obtaining a second solid support wherein the surface of said solid support comprises a reaction well and a mixture of reacts comprising a DNA polymerase, said target nucleic acid, and deoxynucleotides are placed within said reaction well;

(c) assembling said first and second solid support, wherein said mixture of reactants are in contact with said first, second, third, and fourth areas on said first solid support;

(d) releasing said releasable forward and reverse primers;

(e) generating the amplified product for said target nucleic acid;

(f) capturing the amplified product by said first or second polynucleotide probe through hybridization;

(g) washing said first solid support;

(h) comparing the relative binding of two probes on said first solid support; and (i) identifying said polynucleotide variation in the amplified product.

9. A method for amplifying a target nucleic acid, capturing the amplified product, and detecting a polynucleotide sequence variation in the amplified product, comprising the steps of:

(a) obtaining a first solid support wherein:
  (1) the surface of said first array comprises a first, second, third, and fourth areas;
  (2) a first chemical moiety, comprising a releasable forward primer specific for said region of said target nucleic acid, is immobilized on said first area;
  (3) a second chemical moiety, comprising a releasable reverse primer specific for said region of said target nucleic acid, is immobilized on said second area;
  (4) a first polynucleotide probe, comprising a subsequence complementary to one variant of said polynucleotide variation, is immobilized on said third area, said subsequence containing at least one interrogation position complementary to a corresponding nucleotide in said variant; and
  (5) a second polynucleotide probe is immobilized to said fourth area, said second probe differing from said first probe by at least one nucleotide;

(b) obtaining a second solid support wherein the surface of said solid support comprises a reaction well and a mixture of reactants comprising a DNA polymerase, said target nucleic acid, and deoxynucleotides are placed within said reaction well;

(c) assembling said first and second solid support, wherein said mixture of reactants are in contact with said first, second, third, and fourth areas on said first solid support;

(d) releasing said releasable forward and reverse primers;

(e) generating the amplified product for said target nucleic acid;

(f) capturing the amplified product by said first or second polynucleotide probes through hybridization;

(g) extending said one or more hybridization complexes in step (f);

(h) washing said first solid support; and (i) identifying said polynucleotide variation using said one or more extended products in step (g).

10. The method according to any one of the claims 1–2 and 3–9 wherein said areas on the surface of said first solid support are hydrophilic areas.

11. The method according to any one of the claims 1–2 and 3–9 wherein the density of areas on said first solid support is between about 10 to 10,000 per $cm^2$.

12. The method according to any one of the claims 1–2 and 3–9 wherein the size of each said area on said first solid support is between about $10^{-3}$ to 5 $mm^2$.

13. The method according to any one of the claims 1–2 and 3–9 wherein the number of areas on said first solid support is between about 10 to 500,000.

14. The method according to any one of the claims 3–9 wherein said immobilized moieties are prepared by in situ synthesis.

15. The method according to any one of the claims 3–9 wherein said immobilized moieties are prepared by spotting.

16. The method according to any one of the claims 3–9 wherein said immobilized moieties are prepared using an ink-jet printing like device.

17. The method according to any one of the claims 3–9 wherein each of said plurality of areas on said second solid support is a reaction well.

18. The method according to any one of the claims 3–9 wherein said immobilized moiety on each area of said first solid support in step (a) is a hybridization complex between an immobilized polynucleotide hybridized with a releasable primer for said polynucleotide amplification reactions.

19. The method according to any one of the claims 3–9 wherein said immobilized moiety on each area of said first solid support in step (a) comprises a cleavable site and a releasable primer.

20. The method according to any one of the claims 3–9 wherein said immobilized moiety on each area of said first solid support in step (a) comprises a cleavable site and a releasable primer for said polynucleotide amplification reactions and said cleavable site is cleavable by photolysis.

21. The method according to any one of the claims 3–9 wherein said immobilized moiety on each area of said first solid support comprises a cleavable site and a releasable primer for said polynucleotide amplification reactions and said cleavable site comprises an o-nitrobenzyl linker.

22. The method according to any one of the claims 1–2 and 3–9 wherein said first or second solid support is glass.

23. The method according to claim 1 wherein said releasable primers are released by photolysis in step (e).

24. The method according to claim 1 wherein said releasable primers are released by strand separation in step (e).

25. The method according to claim 1 wherein said releasable primers are released by enzymatic reaction in step (e).

* * * * *

SEQUENCE LISTING

<160> NUMBER OF SEQ ID NOS: 32

<210> SEQ ID NO 1
<211> LENGTH: 17
<212> TYPE: DNA
<213> ORGANISM: Homo sapiens

<400> SEQUENCE: 1
ctcaacccga atctccg         17

<210> SEQ ID NO 2
<211> LENGTH: 15
<212> TYPE: DNA
<213> ORGANISM: Homo sapiens

<400> SEQUENCE: 2
gcatgcatgc atgca           15

<210> SEQ ID NO 3
<211> LENGTH: 23
<212> TYPE: DNA

```
<213> ORGANISM: Homo sapiens

<400> SEQUENCE: 3
ttttatcgga gattcgggtt gag                                              23

<210> SEQ ID NO 4
<211> LENGTH: 23
<212> TYPE: DNA
<213> ORGANISM: Homo sapiens

<400> SEQUENCE: 4
ctcaacccga atctccgata aaa                                              23

<210> SEQ ID NO 5
<211> LENGTH: 29
<212> TYPE: DNA
<213> ORGANISM: Homo sapiens

<400> SEQUENCE: 5
gatgctaccg tgactgactg actgactga                                        29

<210> SEQ ID NO 6
<211> LENGTH: 23
<212> TYPE: DNA
<213> ORGANISM: Homo sapiens

<400> SEQUENCE: 6
ctcaacccga atctccgata aaa                                              23

<210> SEQ ID NO 7
<211> LENGTH: 23
<212> TYPE: DNA
<213> ORGANISM: Homo sapiens

<400> SEQUENCE: 7
cgggtcatgt cttcaactaa ctg                                              23

<210> SEQ ID NO 8
<211> LENGTH: 15
<212> TYPE: DNA
<213> ORGANISM: Homo sapiens

<400> SEQUENCE: 8
ctttggaccc accca                                                       15

<210> SEQ ID NO 9
<211> LENGTH: 13
<212> TYPE: DNA
<213> ORGANISM: Homo sapiens

<400> SEQUENCE: 9
ctttgggccc acc                                                         13

<210> SEQ ID NO 10
<211> LENGTH: 17
<212> TYPE: DNA
<213> ORGANISM: Homo sapiens

<400> SEQUENCE: 10
tgggtgggtc caaagaa                                                     17

<210> SEQ ID NO 11
<211> LENGTH: 17
```

-continued

```
<212> TYPE: DNA
<213> ORGANISM: Homo sapiens

<400> SEQUENCE: 11
tgggtgggcc caaagaa                                                    17

<210> SEQ ID NO 12
<211> LENGTH: 23
<212> TYPE: DNA
<213> ORGANISM: Homo sapiens

<400> SEQUENCE: 12
ttttatcgga gattcgggtt gag                                             23

<210> SEQ ID NO 13
<211> LENGTH: 23
<212> TYPE: DNA
<213> ORGANISM: Homo sapiens

<400> SEQUENCE: 13
ggagagagaa gacagttcgt ctt                                             23

<210> SEQ ID NO 14
<211> LENGTH: 23
<212> TYPE: DNA
<213> ORGANISM: Homo sapiens

<400> SEQUENCE: 14
aaaatagcct ctaagcccaa ctc                                             23

<210> SEQ ID NO 15
<211> LENGTH: 23
<212> TYPE: DNA
<213> ORGANISM: Homo sapiens

<400> SEQUENCE: 15
gtcaatcaac ttctgtactg ggc                                             23

<210> SEQ ID NO 16
<211> LENGTH: 21
<212> TYPE: DNA
<213> ORGANISM: Homo sapiens

<400> SEQUENCE: 16
tcacattgta agaagaaacc a                                               21

<210> SEQ ID NO 17
<211> LENGTH: 21
<212> TYPE: DNA
<213> ORGANISM: Homo sapiens

<400> SEQUENCE: 17
tcacattgta agaagaaacc c                                               21

<210> SEQ ID NO 18
<211> LENGTH: 21
<212> TYPE: DNA
<213> ORGANISM: Homo sapiens

<400> SEQUENCE: 18
tcacattgta agaagaaacc g                                               21

<210> SEQ ID NO 19
```

-continued

```
<211> LENGTH: 21
<212> TYPE: DNA
<213> ORGANISM: Homo sapiens

<400> SEQUENCE: 19
tcacattgta agaagaaacc t                                              21

<210> SEQ ID NO 20
<211> LENGTH: 17
<212> TYPE: DNA
<213> ORGANISM: Homo sapiens

<400> SEQUENCE: 20
gagacaccac ccaccca                                                   17

<210> SEQ ID NO 21
<211> LENGTH: 17
<212> TYPE: DNA
<213> ORGANISM: Homo sapiens

<400> SEQUENCE: 21
gagacaccac ccacccc                                                   17

<210> SEQ ID NO 22
<211> LENGTH: 17
<212> TYPE: DNA
<213> ORGANISM: Homo sapiens

<400> SEQUENCE: 22
gagacaccac ccacccg                                                   17

<210> SEQ ID NO 23
<211> LENGTH: 17
<212> TYPE: DNA
<213> ORGANISM: Homo sapiens

<400> SEQUENCE: 23
gagacaccac ccaccct                                                   17

<210> SEQ ID NO 24
<211> LENGTH: 23
<212> TYPE: DNA
<213> ORGANISM: Homo sapiens

<400> SEQUENCE: 24
tgatcacatt gtaagaagaa aca                                            23

<210> SEQ ID NO 25
<211> LENGTH: 23
<212> TYPE: DNA
<213> ORGANISM: Homo sapiens

<400> SEQUENCE: 25
tgatcacatt gtaagaagaa acc                                            23

<210> SEQ ID NO 26
<211> LENGTH: 23
<212> TYPE: DNA
<213> ORGANISM: Homo sapiens

<400> SEQUENCE: 26
tgatcacatt gtaagaagaa acg                                            23
```

-continued

```
<210> SEQ ID NO 27
<211> LENGTH: 23
<212> TYPE: DNA
<213> ORGANISM: Homo sapiens

<400> SEQUENCE: 27
tgatcacatt gtaagaagaa act                                              23

<210> SEQ ID NO 28
<211> LENGTH: 17
<212> TYPE: DNA
<213> ORGANISM: Homo sapiens

<400> SEQUENCE: 28
ggagacacca cccacca                                                     17

<210> SEQ ID NO 29
<211> LENGTH: 17
<212> TYPE: DNA
<213> ORGANISM: Homo sapiens

<400> SEQUENCE: 29
ggagacacca cccaccc                                                     17

<210> SEQ ID NO 30
<211> LENGTH: 17
<212> TYPE: DNA
<213> ORGANISM: Homo sapiens

<400> SEQUENCE: 30
ggagacacca cccaccg                                                     17

<210> SEQ ID NO 31
<211> LENGTH: 17
<212> TYPE: DNA
<213> ORGANISM: Homo sapiens

<400> SEQUENCE: 31
ggagacacca cccacct                                                     17

<210> SEQ ID NO 32
<211> LENGTH: 20
<212> TYPE: DNA
<213> ORGANISM: Homo sapiens

<400> SEQUENCE: 32
actgactgac tgactgactg                                                  20
```